US012275757B2

(12) United States Patent
King et al.

(10) Patent No.: US 12,275,757 B2
(45) **Date of Patent: *Apr. 15, 2025**

(54) SELF-ASSEMBLING PROTEIN NANOSTRUCTURES DISPLAYING PARAMYXOVIRUS AND/OR PNEUMOVIRUS F PROTEINS AND THEIR USE

(71) Applicants: University of Washington, Seattle, WA (US); INSTITUTE FOR RESEARCH IN BIOMEDICINE, Bellinzona (CH)

(72) Inventors: Neil P. King, Seattle, WA (US); David Baker, Seattle, WA (US); Brooke Fiala, Seattle, WA (US); Lance Joseph Stewart, Seattle, WA (US); Laurent Perez, Bellinzona (CH); Antonio Lanzavecchia, Bellinzona (CH); Jessica Marcandalli, Bellinzona (CH); Jorge Fallas, Seattle, WA (US); Yang Hsia, Seattle, WA (US)

(73) Assignees: UNIVERSITY OF WASHINGTON, Seattle, WA (US); INSTITUTE FOR RESEARCH IN BIOMEDICINE, Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/337,881

(22) Filed: Jun. 20, 2023

(65) Prior Publication Data

US 2024/0150411 A1 May 9, 2024

Related U.S. Application Data

(60) Continuation of application No. 17/523,174, filed on Nov. 10, 2021, now Pat. No. 11,732,011, which is a division of application No. 16/500,331, filed as application No. PCT/US2018/025880 on Apr. 3, 2018, now Pat. No. 11,192,926.

(60) Provisional application No. 62/481,331, filed on Apr. 4, 2017.

(51) Int. Cl.

| | |
|---|---|
| *A61K 39/12* | (2006.01) |
| *A61K 39/00* | (2006.01) |
| *A61K 39/155* | (2006.01) |
| *A61K 39/385* | (2006.01) |
| *A61P 31/14* | (2006.01) |
| *B82Y 5/00* | (2011.01) |
| *C07K 14/005* | (2006.01) |
| *C12N 7/00* | (2006.01) |

(52) U.S. Cl.

CPC ............ *C07K 14/005* (2013.01); *A61K 39/12* (2013.01); *A61P 31/14* (2018.01); *B82Y 5/00* (2013.01); *C12N 7/00* (2013.01); *A61K 2039/575* (2013.01); *C07K 2319/735* (2013.01); *C12N 2760/18022* (2013.01); *C12N 2760/18322* (2013.01); *C12N 2760/18522* (2013.01)

(58) Field of Classification Search

CPC .............. A61K 39/12; A61K 2039/575; A61K 39/155; A61K 2039/55555; B82Y 5/00

See application file for complete search history.

(56) References Cited

U.S. PATENT DOCUMENTS

| | | | |
|---|---|---|---|
| 6,262,202 | B1 | 7/2001 | Walzer et al. |
| 6,303,767 | B1 | 10/2001 | Betlach et al. |
| 6,929,933 | B1 | 8/2005 | Revuelta Doval et al. |
| 8,563,002 | B2 | 10/2013 | Baudoux et al. |
| 8,969,521 | B2 | 3/2015 | Baker et al. |
| 9,441,019 | B2 | 9/2016 | Nabel et al. |
| 9,487,593 | B2 | 11/2016 | Powell et al. |
| 9,630,994 | B2 | 4/2017 | Baker et al. |
| 9,738,689 | B2 | 8/2017 | Kwong et al. |
| 9,856,313 | B2 | 1/2018 | Zheng et al. |
| 9,913,894 | B2 | 3/2018 | Tous et al. |
| 9,950,058 | B2 | 4/2018 | Che et al. |
| 10,017,543 | B2 | 7/2018 | Kwong et al. |
| 10,022,437 | B2 | 7/2018 | Pushko et al. |
| 10,040,828 | B2 | 8/2018 | Weiner et al. |
| 10,351,603 | B2 | 7/2019 | Baker et al. |

(Continued)

FOREIGN PATENT DOCUMENTS

| | | |
|---|---|---|
| CN | 104436202 | 7/2017 |
| CN | 107157933 | 9/2017 |

(Continued)

OTHER PUBLICATIONS

Georgiev et al., "Two-Component Ferritin Nanoparticles for Multimerization of Diverse Trimeric Antigens." ACS Infect Dis. May 11, 2018;4(5):788-796. doi: 10.1021/acsinfecdis.7b00192. Epub Mar. 6, 2018. PMID: 29451984—Abstract provided.

(Continued)

*Primary Examiner* — Barry A Chestnut
(74) *Attorney, Agent, or Firm* — MCDONNELL BOEHNEN HULBERT & BERGHOFF LLP

(57) ABSTRACT

Disclosed herein are nanostructures and their use, where the nanostructures include (a) a plurality of first assemblies, each first assembly comprising a plurality of identical first polypeptides;
(b) a plurality of second assemblies, each second assembly comprising a plurality of identical second polypeptides, wherein the second polypeptide differs from the first polypeptide;

wherein the plurality of first assemblies non-covalently interact with the plurality of second assemblies to form a nanostructure; and wherein the nanostructure displays multiple copies of one or more paramyxovirus and/or pneumovirus F proteins or antigenic fragments thereof, on an exterior of the nanostructure.

50 Claims, 16 Drawing Sheets

Specification includes a Sequence Listing.

(56) References Cited

U.S. PATENT DOCUMENTS

| | | |
|---|---|---|
| 11,485,759 B2 | 11/2022 | Baker et al. |
| 11,732,011 B2 | 8/2023 | King et al. |
| 11,771,755 B2 | 10/2023 | King et al. |
| 2004/0005672 A1 | 1/2004 | Santi et al. |
| 2004/0214276 A1 | 10/2004 | Khosla et al. |
| 2011/0085939 A1 | 4/2011 | Salemme et al. |
| 2011/0200560 A1 | 8/2011 | Zhang |
| 2012/0213817 A1 | 8/2012 | Haynes |
| 2013/0122032 A1 | 5/2013 | Smith et al. |
| 2014/0248314 A1 | 9/2014 | Swanson et al. |
| 2014/0302079 A1 | 10/2014 | Nabel et al. |
| 2015/0110825 A1 | 4/2015 | Sasisekharan et al. |
| 2015/0356240 A1 | 12/2015 | Baker et al. |
| 2016/0046675 A1 | 2/2016 | Kwong et al. |
| 2016/0122392 A1 | 5/2016 | Baker et al. |
| 2016/0159864 A1 | 6/2016 | Carfi et al. |
| 2016/0324958 A1 | 11/2016 | Burkhard et al. |
| 2017/0182151 A1 | 6/2017 | Che et al. |
| 2017/0189519 A1 | 7/2017 | Impagliazzo et al. |
| 2017/0202948 A1 | 7/2017 | Smith et al. |
| 2017/0298101 A1 | 10/2017 | Kwong et al. |
| 2017/0326228 A1 | 11/2017 | Cheminay et al. |
| 2018/0021258 A1 | 1/2018 | Graham et al. |
| 2018/0194808 A1 | 7/2018 | Langedijk et al. |
| 2018/0200360 A1 | 7/2018 | Langedijk et al. |
| 2018/0237476 A1 | 8/2018 | Swanson et al. |
| 2018/0256704 A1 | 9/2018 | Nicosia et al. |
| 2019/0330279 A1 | 10/2019 | Kwong et al. |
| 2020/0392187 A1 | 12/2020 | King |

FOREIGN PATENT DOCUMENTS

| | | |
|---|---|---|
| EP | 1 010 760 | 6/2000 |
| WO | WO 2006/033679 | 3/2006 |
| WO | WO 2010/019725 | 2/2010 |
| WO | WO 2010/035009 | 4/2010 |
| WO | WO 2011/019585 | 2/2011 |
| WO | WO 2013/044203 | 3/2013 |
| WO | WO 2013/056122 | 4/2013 |
| WO | 2014/124301 A1 | 8/2014 |
| WO | 2015/048149 A9 | 4/2015 |
| WO | 2015/177312 A1 | 11/2015 |
| WO | WO 2016/138525 | 9/2016 |
| WO | WO 2016/160166 | 10/2016 |
| WO | WO 2017/005844 | 1/2017 |
| WO | 2017/040387 A2 | 3/2017 |
| WO | 2017066484 A2 | 4/2017 |
| WO | 2017070626 A2 | 4/2017 |
| WO | WO 2017/075125 | 5/2017 |
| WO | WO 2017/172890 | 10/2017 |
| WO | WO 2017/174568 | 10/2017 |
| WO | WO 2017/207477 | 12/2017 |
| WO | WO 2017/207480 | 12/2017 |
| WO | WO 2018/005558 | 1/2018 |
| WO | WO 2018/109220 | 6/2018 |

OTHER PUBLICATIONS

Kanekiyo et al., "Self-assembling influenza nanoparticle vaccines elicit broadly neutralizing H1N1 antibodies." Nature. Jul. 4, 2013;499(7456):102-6. doi: 10.1038/nature12202. Epub May 22, 2013. PMID: 23698367.

Olsen, "Gene transfer vectors derived from equine infectious anemia virus," Gene Therapy, vol. 5, No. 11, pp. 1481-1487, 1998.

Otwinowski, et al., "[20] Processing of X-ray diffraction data collected in oscillation mode," Methods in Enzymology, vol. 276, pp. 307-326, 1997.

Oubridge, et al., "Crystal structure at 1.92 A resolution of the RNA-binding domain of the U1A spliceosomal protein complexed with an RNA hairpin," Nature, vol. 372, No. 6505, pp. 432-438, 1994.

Pancera, et al., "Structure and immune recognition of trimeric pre-fusion HIV-1 Env.," Nature, vol. 514, No. 7523, pp. 455-461, 2014.

Parent, et al., "Positionally independent and exchangeable late budding functions of the Rous Sarcoma Virus and Human Immunodeficiency Virus Gag proteins," Journal of Virology, vol. 69, No. 9, pp. 5455-5460, 1995.

Patterson, et al., "Characterization of a highly flexible self-assembling protein system designed to form nanocages," Protein Science, vol. 23, No. 2, pp. 190-199, 2014.

Pesarrodona, et al., "Intracellular targeting of CD44+ cells with self-assembling, protein only nanoparticles," International Journal of Pharmaceutics, vol. 473, No. 1-2, pp. 286-295, 2014.

Puglisi, et al., "Solution structure of a bovine immunodeficiency virus Tat-TAR peptide-RNA complex," Science, vol. 270, No. 5239, pp. 1200-1203, 1995.

Resh, "Covalent lipid modifications of proteins," Current Biology, vol. 23, No. 10, pp. R431-R435, 2013.

Resh, "Fatty acylation of proteins: new insights into membrane targeting of myristoylated and palmitoylated proteins," Biochimica et Biophysica Acta, vol. 1451, No. 1, pp. 1-16, 1999.

Rosa, et al., "HIV-1 Nef promotes infection by excluding SERINC5 from virion incorporation," Nature, vol. 526, No. 1572, pp. 212-217, 2015.

Salgado, et al., "Controlling protein-protein interactions through metal coordination: assembly of a 16-helix bundle protein," Journal of the American Chemical Society, vol. 129, No. 44, p. 13374-13375, 2007.

Schneidman-Duhovny et al., "Accurate SAXS Profile Computation and its Assessment by Contrast Variation Experiements," Biophysical Journal, Aug. 2013, pp. 962-974, vol. 105.

Schneidman-Duhovny et al., "FoXS: a web server for rapid computation and fitting of SAXS profiles," Nucleic Acids Research, 2010, pp. W540-W544, vol. 38.

Schrodinger, LLC, "The PyMOL Molecular Graphics System, Version 1.4," available online at: http://www.pymol.org, 2011.

Schuck, "Size-distribution analysis of macromolecules by sedimentation velocity ultracentrifugation and lamm equation modeling," Biophysical Journal, vol. 78, No. 3, pp. 1606-1619, 2000.

Stahelin, "Lipid binding domains: more than simple lipid effectors," Journal of Lipid Research, vol. 50, Suppl S299-S304, 2009.

Sun, et al., "Cyclic GMP-AMP synthase is a cytosolic DNA sensor that activates the type I interferon pathway," Science, vol. 339, No. 6121, pp. 786-791, 2013.

Thery, et al., "Isolation and Characterization of Exosomes from Cell and Culture Supernatants and Biological Fluids," Current Protocols in Cell Biology, Chapter 3, Unit 3.22, pp. 3.22.1-3.22.19, 2006.

Tobiume, et al., "Nef does not affect the efficiency of human immunodeficiency virus type 1 fusion with target cells," Journal of Virology, vol. 77, No. 19, pp. 10645-10650, 2003.

Tsai, et al., "Analysis of lattice-translocation disorder in the layered hexagonal structure of carboxysome shell protein CsoS1C," Acta Crystallographica, Section D: Biological Crystallography, vol. 65, Pt 9, pp. 980-988, 2009.

Tsvetkova, et al., "Cutting edge: an NK cell-independent role for Slamf4 in controlling humoral autoimmunity," Protein Cages, Methods in Molecular Biology, 1252:1-15, 2014.

Usami, et al., "SERINC3 and SERINC5 restrict HIV-1 infectivity and are counteracted by Nef," Nature, vol. 526, No. 1572, pp. 218-223, 2015.

Votteler, et al., "Virus budding the ESCRT pathway," Cell Host & Microbe, vol. 14, No. 3, pp. 232-241, 2013.

Wang, et al., "Expanding the genetic code of *Escherichia coli*," Science, vol. 292, No. 5516, pp. 498-500, 2001.

Whitehead, et al., "Optimization of Affinity, Specificity and Function of Designed Influenza Inhibitors Using Deep Sequencing," Nature Biotechnology, vol. 30, No. 6, pp. 543-548, 2012.

Winn, et al., "Macromolecular TLS refinement in REFMAC at moderate resolutions," Methods in Enzymology, vol. 374, pp. 300-321, 2003.

Wu, et al., "Cyclic GMP-AMP is an endogenous second messenger in innate immune signaling by cytosolic DNA," Science, vol. 339, No. 6121, pp. 826-830, 2013.

(56) References Cited

OTHER PUBLICATIONS

Yeates et al., "Bacterial microcompartment organelles: protein shell structure and evolution," Annual Review of Biophysics, vol. 39, pp. 185-205, 2010.
Yee et al., "Generation of high-titer pseudotyped retroviral vectors with very broad host range," Methods in Cell Biology, vol. 43, Pt A, pp. 99-112, 1994.
Zaccai, et al., "A de novo peptide hexamer with a mutable channel," Nature Chemical Biology, vol. 7, No. 12, pp. 935-941, 2011.
Zacharias, et al., "Partitioning of lipid-modified GFPs into membrane microdomains in live cells," Science, vol. 296, No. 5569, pp. 913-916, 2002.
Zhang, "Fabrication of novel biomaterials through molecular self-assembly," Nature Biotechnology, vol. 21, No. 10, pp. 1171-1178, 2003.
Zhao, et al., "A simple guide to biochemical approaches for analyzing lipid-protein interactions," Molecular Biology of the Cell, vol. 23, No. 15, pp. 2823-2830, 2012.
Zheng, et al., "From molecular to macroscopic via the rational design of a self-assembled 3D DNA crystal," Nature, vol. 461, No. 7260, pp. 74-77, 2009.
PCT/US2014/015371 International Search Report and Written Opinion, 2014.
PCT/US2016/020090, International Search Report and Written Opinion, 10 pages, 2016.
Lanci et al. Computational design of a protein crystal. Proc. Natl Acad. Sci. USA 109, 7304-7309 (2012).
Lawrence & Colman, Shape complementarity at protein/protein interfaces. J. Mol. Biol. 234, 946-950 (1993).
Lawrence et al., Supercharging Proteins Can Impart Unusual Resilience, J. Am. Chem. Soc. 129, 10110-10112 (2007).
Leaver-Fay et al., ROSETTA3: an object-oriented software suite for the simulation and design of macromolecules. Methods Enzymol. 487, 545-574 (2011).
Leaver-Fay et al. Scientific benchmarks for guiding macromolecular energy function improvement. Methods Enzymol. 523, 109-143 (2013).
Lin et al., Structural Fingerprinting: Subgrouping of Comoviruses by Structural Studies of Red Clover Mottle Virus to 2.4-Å Resolution and Comparisons with Other Comoviruses J. Virol. 74, 493-504 (2000).
Lin et al., The Refined Crystal Structure of Cowpea Mosaic Virus at 2.8 Å Resolution, Virology 265, 20-34 (1999).
Ludtke et al., EMAN: semiautomated software for high-resolution single-particle reconstructions. J. Struct. Biol. 128, 82-97 (1999).
Lüthy et al., Assessment of protein models with three-dimensional profiles. Nature 356, 83-85 (1992).
McCoy et al. Phaser crystallographic software. J. Appl. Crystallogr. 40, 658-674 (2007).
Nannenga et al., Overview of electron crystallography of membrane proteins: crystallization and screening strategies using negative stain electron microscopy. Curr. Protoc. Protein Sci. Chapter 17, Unit17.15 (2013).
Nivon et al., Automating human intuition for protein design. Proteins (2013). doi: 10.1002/prot.24463.
Padilla et al., Nanohedra: using symmetry to design self assembling protein cages, layers, crystals, and filaments. Proc. Natl Acad. Sci. USA 98, 2217-2221 (2001).
Painter & Merritt, Optimal description of a protein structure in terms of multiple groups undergoing TLS motion. Acta Crystallogr. D Biol. Crystallogr. 62, 439-450 (2006).
Painter, J. & Merritt, TLSMD web server for the generation of multi-group TLS models. Journal of Applied Crystallography 39, 109-111 (2006).
Pettersen et al. UCSF Chimera—a visualization system for exploratory research and analysis. J. Comput. Chem. 25, 1605-1612 (2004).
Prodromou & Pearl,Recursive PCR: a novel technique for total gene synthesis. Protein Eng. 5, 827-829 (1992).
Raman et al., Design of Peptide Nanoparticles Using Simple Protein Oligomerization Domains, The Open Nanomedicine Journal, 2:15-26 (2009).
Raman et al., Materials Science: Structure-based design of peptides that self-assemble into regular polyhedral nanoparticles, Nanomedicine: Nanotechnology, Biology, and Medicine 2:95-102 (2006).
Ringler & Schulz, Self-Assembly of Proteins into Designed Networks, Science 302:106-09 (2003).
Rothemund, Folding DNA to create nanoscale shapes and patterns. Nature 440, 297-302 (2006).
Salgado et al., Metal-directed protein self-assembly. Acc. Chem. Res. 43, 661-672 (2010).
Schindelin et al. Fiji: an open-source platform for biological-image analysis. Nat. Methods 9, 676-682 (2012).
Seeman, Nanomaterials based on DNA. Annu. Rev. Biochem. 79, 65-87 (2010).
Sheffler & Baker, RosettaHoles2: a volumetric packing measure for protein structure refinement and validation. Protein Sci 19, 1991-1995 (2010).
Sinclair et al., Generation of protein lattices by fusing proteins with matching rotational symmetry. Nature Nanotechnol. 6, 558-562 (2011).
Sinclair, Constructing arrays of proteins. Curr. Opin. Chem. Biol. 17, 946-951 (2013).
Smith, Ximdisp—A visualization tool to aid structure determination from electron microscope images. J. Struct. Biol. 125, 223-228 (1999).
Stranges et al., Computational design of a symmetric homodimer using beta-strand assembly. Proc. Natl Acad. Sci. USA 108, 20562-20567 (2011).
Tinberg et al. Computational design of ligand-binding proteins with high affinity and selectivity. Nature 501, 212-216 (2013).
Usui et al. Nanoscale elongating control of the self-assembled protein filament with the cysteine-introduced building blocks. Protein Sci. 18, 960-969 (2009).
Van Heel et al., A new generation of the IMAGIC image processing system. J. Struct. Biol. 116, 17-24 (1996).
Van Kooten & Banchereau, CD40-CD40 Ligand, J. Leukoc. Biol. 67:2-17 (Jan. 2000).
Voet et al., Computational design of a self-assembling symmetrical β-propeller protein, Proc. Natl. Acad. Sci. U.S.A. 111:15102-107 (2014).
Worsdorfer et al., Directed evolution of a protein container. Science 331, 589-592 (2011).
Worsdorfer et al., Efficient in vitro encapsulation of protein cargo by an engineered protein container. J.Am.Chem. Soc.134,909-911(2012).
Zakeri et al., Peptide tag forming a rapid covalent bond to a protein, through engineering a bacterial adhesin, Proc. Natl. Acad. Sci. U.S.A. 109(12):E690-E697 (Mar. 2012).
Zandi et al., Origin of icosahedral symmetry in viruses, Proc. Natl. Acad. Sci. U.S.A. 101(44): 15556-560 (Nov. 2004).
Zhou et al., Genetically encoded short peptide tags for orthogonal protein labeling by Sfp and AcpS phosphopantetheinyl transferases. ACS Chem. Biol. 2, 337-346 (2007).
Zlotnick et al., A Theoretical Model Successfully Identifies Features of Hepatitis B Virus Capsid Assembly, Biochemistry 38:14644-652 (1999).
Zlotnick et al., Mechanism of Capsid Assembly for an Icosahedral Plant Virus, Virology 277:450-56 (2000).
Zschoche & Hilvert, Diffusion-Limited Cargo Loading of an Engineered Protein Container, Am. Chem. Soc. 137:16121-132 (2015).
The International Search Report (ISR) with Written Opinion for PCT/US2018025880 dated Jun. 29, 2018, pp. 1-19.
Bale, Jacob B. et al. "Accurate design of megadalton-scale two-component icosahedral protein complexes" Science (2016) vol. 353(6297), pp. 389-394.
McLellan, Jason S. et al. "Structure-Based Design of a Fusion Glycoprotein Vaccine for Respiratory Syncytial Virus" Science (2013) vol. 342(6158), pp. 592-598.
Website: http://www.genisphere.com/, 1 page retrieved on Sep. 12, 2016.

(56) References Cited

OTHER PUBLICATIONS

AfosrApan, "Computational design of self- and co-assembling protein nanomaterials with atomic level accuracy" available online at: https://community.apan.org/afosr/w/researchareas/7659.human-performance-and-biosystems.aspx, 2014.

Andersen, et al., "Self-assembly of a nanoscale DNA box with a controllable lid," Nature, vol. 459, No. 7243, pp. 73-76, 2009.

Apolonia, et al., "Promiscuous RNA binding ensures effective encapsidation of APOBEC3 proteins by HIV-1," PLoS Pathogens, vol. 11, No. 1, e1004609, 2015.

Bagby, et al., "[2]—Optimization of Protein Solubility and Stability for Protein Nuclear Magnetic Resonance," Methods in Enzymology, vol. 339, pp. 20-41, 2001.

Ballister, et al., "In vitro self-assembly of tailorable nanotubes from a simple protein building block," Proceedings of the National Academy of Sciences USA, vol. 105, No. 10, pp. 3733-3738, 2008.

Bieniasz, "Late budding domains and host proteins in enveloped virus release," Virology, vol. 344, No. 1, pp. 55-63, 2006.

Biswas, et al., "The human immunodeficiency virus type 1 ribosomal frameshifting site is an invariant sequence determinant and an important target for antiviral therapy," Journal of Virology, vol. 78, No. 4, pp. 2082-2087, 2004.

Blanc, et al., "Refinement of severely incomplete structures with maximum likelihood in BUSTER-TNT," Acta Carystallographica, Section D: Biological Crystallography, vol. 60, Pt 12, Pt 1, pp. 2210-2221, 2004.

Bondos, et al., "Detection and Prevention of Protein Aggregation Before, During, and After Purification," Analytical Biochemistry, vol. 316, No. 2, pp. 223-231, 2003.

Bridgeman, et al., "Viruses transfer the antiviral second messenger cGAMP between cells," Science, vol. 349, No. 6253, pp. 1228-1232, 2015.

Cavrois, et al., "A sensitive and specific enzyme-based-assay detecting HIV-1 virion fusion in primary T lymphocytes," Nature Biotechology, vol. 20, No. 11, pp. 1151-1154, 2002.

Chao, et al., "Isolating and Engineering Human Antibodies Using Yeast Surface Display," Nature Protocols, vol. 1, No. 2, pp. 755-768, 2016.

Chao, et al., "Structural basis for the coevolution of a viral RNA-protein complex," Nature Structural & Molecular Biology, vol. 15, No. 1, pp. 103-105, 2008.

Cooper, et al., "Predicting protein structures with a multiplayer online game," Nature, vol. 466, No. 7307, pp. 756-760, 2010.

Crowley, et al., "Structural insight into the mechanisms of transport across the *Salmonella enterica* Pdu microcompartment shell," Journal of Biological Chemistry, vol. 285, No. 48, pp. 37838-37846, 2010.

Das, et al., "Simultaneous prediction of protein folding and docking at high resolution," Proceedings of the National Academy of Sciences USA, vol. 106, No. 45, pp. 18978-18983, 2009.

De Guzman, et al., "Structure of the HIV-1 nucleocapsid protein bound to the SL3 psi-RNA recognition element," Science, vol. 279, No. 5349, pp. 384-388, 1998.

Fleishman, et al., "Hotspot-centric de novo design of protein binders," Journal of Molecular Biology, vol. 413, No. 5, pp. 1047-1062, 2011.

Freed, et al., "Single amino acid changes in the human immunodeficiency virus type 1 matrix block virus particle production," Journal of Virology, vol. 68, No. 8, pp. 5311-5320, 1994.

Gentili, et al., "Transmission of innate immune signaling by packaging of cGAMP in viral particles," Science, vol. 349, No. 6253, pp. 1232-1236, 2015.

Golovanov, et al., "A Simple Method for Improving Protein Solubility and Long-Term Stability," Journal of the American Chemical Society, vol. 126, No. 29, pp. 8933-8939, 2004.

Gosser, et al., "Peptide-triggered conformational switch in HIV-1 RRE RNA complexes," Nature Structural Biology, vol. 8, No. 2, pp. 146-150, 2001.

Gray et al., "Cutting Edge: cGAS is Required for Lethal Autoimmune Disease in the Trex1-Deficient Mouse Model of Aicardi-Goutieres Syndrome," Journal of Immunology, vol. 195, No. 5, pp. 1939-1943, 2015.

Gribbon, et al., "MagicWand: a single, designed peptide that assembles to stable, ordered alpha-helical fibers," Biochemistry, vol. 47, No. 39, pp. 10365-10371, 2008.

Griffiths, et al., "Cloning, isolation and characterization of the Thermotoga maritima KDPG aldolase," Bioorganic & Medicinal Chemistry, vol. 10, No. 3, pp. 545-550, 2002.

Grigorieff, "FREALIGN: high-resolution refinement of single particle structures," Journal of Structural Biology, vol. 157, No. 1, pp. 117-125, 2007.

Harbury, et al., "High-resolution protein design with backbone freedom," Science, vol. 282, No. 5393, pp. 1462-1467, 1998.

Hurley, et al., "Membrane Budding and Scission by the ESCRT Machinery: It's All in the Neck," Nature Reviews Molecular Cell Biology, vol. 11, No. 8, pp. 556-566, 2010.

Ishikawa, et al., "STING is an endoplasmic reticulum adaptor that facilitates innate immune signalling," Nature, vol. 455, No. 7213, pp. 674-678, 2008.

Jacak, et al., "Computational Protein Design with Explicit Consideration of Surface Hydrophobic Patches," Proteins: Structure, Function, and Bioinformatics, vol. 80, No. 3, pp. 825-838, 2012.

Jackel, et al., "Consensus Protein Design Without Phylogenetic Bias," Journal of Molecular Biology, vol. 399, No. 4, pp. 541-546, 2010.

Julien, et al., "Crystal structure of a soluble cleaved HIV-1 envelope trimer," Science, vol. 342, No. 6165, pp. 1477-1483, 2013.

Koder, et al., "Design and engineering of an O(2) transport protein," Nature, vol. 458, No. 7236, pp. 305-309, 2009.

Kortemme, et al., "Computational redesign of protein-protein interaction specificity," Nature Structural & Molecular Biology, vol. 11, No. 4, pp. 371-379, 2004.

Kremer, et al., "Computer visualization of three-dimensional image data using IMOD," Journal of Structural Biology, vol. 116, No. 1, pp. 71-76, 1996.

Kumar, et al., "Crystal structure analysis of icosahedral lumazine synthase from *Salmonella typhimurium*, an antibacterial drug target," Acta Crystallographica, Section D: Biological Crystallography, vol. 67, Pt 2, pp. 131-139, 2011.

Laskowski, et al., "Procheck: a program to check the stereochemical quality of protein structures," Journal of Applied Crystallography, 26:283-291, 1993.

Lemmon, "Membrane recognition by phospholipid-binding domains." Nature Reviews Molecular Cell Biology, vol. 9, No. 2, pp. 99-111, 2008.

Levy, et al., "3D complex: a structural classification of protein complexes," PLoS Computational Biology, vol. 2, No. 11, e155, pp. 1395-1406, 2006.

Lovejoy, et al., "Crystal structure of a synthetic triple-stranded alpha-helical bundle," Science, vol. 259, No. 5099, pp. 1288-1293, 1993.

Lyumkis, et al., "Cryo-EM structure of a fully glycosylated soluble cleaved HIV-1 envelope timer," Science, vol. 342, No. 6165, pp. 1484-1490, 2013.

Mangeot, et al., "Protein transfer into human cells by VSV-G-induced nanovesicles," Molecular Therapy, vol. 19, No. 9, pp. 1656-1666, 2011.

McCullough, et al., "Membrane Fission Reactions of the Mammalian ESCRT Pathway," Annual Review of Biochemistry, vol. 82, pp. 663-692, 2013.

McDonald, et al., "No strings attached: the ESCRT machinery in viral budding and cytokinesis," Journal of Cell Science, vol. 122, Pt 13, pp. 2167-2177, 2009.

Mindell, et al., "Accurate determination of local defocus and specimen tilt in electron microscopy," Journal of Structural Biology, vol. 142, No. 3, pp. 334-347, 2003.

Murshudov, et al., "Refinement of macromolecular structures by the maximum-likelihood method," Acta Crystallographica, Section D: Biological Crystallography, vol. 53, Pt 3, pp. 240-255, 1997.

Nam, et al., "Molecular basis for interaction of let-7 microRNAs with Lin28," Cell, vol. 147, No. 5, pp. 1080-1091, 2011.

(56) References Cited

OTHER PUBLICATIONS

Ni, et al., "Crystal structure of the MS2 coat protein dimer: implication for RNA binding and virus assembly," Structure, vol. 3, No. 3, pp. 255-263, 1995.
Ohi, et al., "Negative staining and image classification—powerful tools in modern electron microscopy," Biological Procedures Online, vol. 6, pp. 23-34, 2004.
Adams et al., PHENIX: a comprehensive Python-based system for macromolecular structure solution. Acta Crystallogr. D Biol. Crystallogr. 66, 213-221 (2010).
Arnold & Volkov, Directed evolution of biocatalysts. Curr. Opin. Chem. Biol. 3, 54-59 (1999).
Bale et al., Structure of a designed tetrahedral protein assembly variant engineered to have improved soluble expression, Protein Sci. 24:1695-1701 (2015).
Boyle et al., Squaring the circle in peptide assembly: from fibers to discrete nanostructures by de novo design. J. Am. Chem. Soc. 134, 15457-15467 (2012).
Bradley & Baker, Improved beta-protein structure prediction by multilevel optimization of nonlocal strand pairings and local backbone conformation. Proteins 65, 922-929 (2006).
Brodin et al., et al. Metal-directed, chemically tunable assembly of one-, two- and three-dimensional crystalline protein arrays. Nature Chem. 4, 375-382 (2012).
Burkhard et al., Malaria vaccine based on Self-Assembling Protein Nanoparticles, Expert Rev. Vaccines 14(12):1525-27 (2015).
Caspar & Klug, The Principles in the Contstruction of Regular Viruses, Cold Spring Harb. Symp. Quant. Biol. 27, 1-24 (1962).
Chan et al. Structure and function of P19, a high-affinity iron transporter of the human pathogen *Campylobacter jejuni*. J. Mol. Biol. 401, 590-604 (2010).
Colovos & Yeates, Verification of protein structures: patterns of nonbonded atomic interactions. Protein Sci. 2, 1511-1519 (1993).
Correia et al., Proof of principle for epitope-focused vaccine design, Nature 507(7491):201-06 (2014).
Davis et al. MolProbity: all-atom contacts and structure validation for proteins and nucleic acids. Nucleic Acids Res. 35, W375-383 (2007).
Dempsey et al., C3d of Complement as a Molecular Adjuvant: Bridging Innate and Acquired Immunity, Science, 271:348-50 (Jan. 1996).
Der et al., Metal-mediated affinity and orientation specificity in a computationally designed protein homodimer. J. Am. Chem. Soc. 134, 375-385 (2012).
DiMaio et al., Modeling symmetric macromolecular structures in Rosetta3. PLoS ONE 6, e20450 (2011).
Douglas & Young, Viruses: making friends with old foes. Science 312, 873-875 (2006).
Dyer et al., High-Throughput SAXS for the Characterization of Biomolecules in Solution: A Practical Approach, Methods Mol. Biol. 1091:245-58 (2014).
Emsley et al., Features and development of Coot. Acta Crystallogr. D Biol. Crystallogr. 66, 486-501 (2010).
Fallas et al., Computational Design of Self-Assembling Cyclic Protein Homo-oligomers, Nat. Chem. 9(4):353-60 (Apr. 2017).
Fleishman et al., Computational design of proteins targeting the conserved stem region of influenza hemagglutinin. Science 332, 816-821 (2011).
Fleishman et al. Community-wide assessment of protein-interface modeling suggests improvements to design methodology. J. Mol. Biol. 414, 289-302 (2011).
Fleishman et al. RosettaScripts: a scripting language interface to the Rosetta macromolecular modeling suite. PLoS One 6, e20161 (2011).
Fleishman et al., Restricted sidechain plasticity in the structures of native proteins and complexes. Protein Sci. 20, 753-757 (2011).
Fletcher et al. Self-assembling cages from coiled-coil peptide modules. Science 340, 595-599 (2013).
Frank et al. SPIDER and WEB: processing and visualization of images in 3D electron microscopy and related fields. J. Struct. Biol. 116, 190-199 (1996).
Gibson et al. Enzymatic assembly of DNA molecules up to several hundred kilobases. Nat. Methods 6, 343-345 (2009).
Glen et al., A Randomized, Blinded, Controlled, Dose-Ranging Study of a Respiratory Syncytial Virus Recombinant Fusion, J. Infect. Dis. 213(3):411-22 (2016).
Gonen et al., Design of ordered two-dimensional arrays mediated by noncovalent protein-protein interfaces, Science 348:1365-68 (2015).
Goodsell & Olson, Structural symmetry and protein function. Annu. Rev. Biophys. Biomol. Struct. 29, 105-153 (2000).
Grigoryan et al. Computational design of virus-like protein assemblies on carbon nanotube surfaces. Science 332, 1071-1076 (2011).
Grueninger et al. Designed protein-protein association. Science 319, 206-209 (2008).
Han et al. DNA gridiron nanostructures based on four-arm junctions. Science 339, 1412-1415 (2013).
Howorka, Rationally engineering natural protein assemblies in nanobiotechnology. Curr. Opin. Biotechnol. 22, 485-491 (2011).
Hsia et al., Design of a hyperstable 60-subunit protein icosahedron, Nature 535:136-39 (2016).
Huang et al., A de novo designed protein protein interface. Protein Sci. 16, 2770-2774 (2007).
Jackel et al., Protein design by directed evolution. Annu. Rev. Biophys. 37, 153-173 (2008).
Janin et al., Protein-protein interaction and quaternary structure. Q. Rev. Biophys. 41, 133-180 (2008).
Jha et al., Computational design of a PAK1 binding protein. J. Mol. Biol. 400, 257-270 (2010).
Kabsch, Xds. Acta Crystallogr. D Biol. Crystallogr. 66, 125-132 (2010).
Karanicolas et al., A de novo protein binding pair by computational design and directed evolution. Mol. Cell 42, 250-260 (2011).
Ke, Three-dimensional structures self-assembled from DNA bricks. Science 338, 1177-1183 (2012).
Khare & Fleishman, Emerging themes in the computational design of novel enzymes and protein-protein interfaces. FEBSLett. 587, 1147-1154(2013).
King & Lai, Practical approaches to designing novel protein assemblies. Curr. Opin. Struct. Biol. 23, 632-638 (2013).
King et al. Computational design of self-assembling protein nanomaterials with atomic level accuracy. Science 336, 1171-1174 (2012).
King et al., "Accurate design of coassembling multi-component protein nanomaterials" Nature 510(7503):103-108 (Jun. 2014). With supplementary data.
Krissinel & Henrick, Inference of macromolecular assemblies from crystalline state. J. Mol. Biol. 372, 774-797 (2007).
Kuhlman & Baker, Native protein sequences are close to optimal for their structures. Proc. Natl Acad. Sci. USA 97, 10383-10388 (2000).
Lai et al., Structure of a Designed Protein Cage that Self-Assembles into a Highly Porous Cube, Nat. Chem. 6:1065-71 (2014).
Lai et al., Principles for designing ordered protein assemblies. Trends Cell Biol. 22, 653-661 (2012).
Lai et al., Structure of a 16-nm cage designed by using protein oligomers. Science 336:1129-30 (Jun. 2012).
U.S. Appl. No. 16/427,493, filed May 31, 2019, Baker et al.
A0A4P2AVB8_STRVZ, the sequence of the SAM-dependent methyltransferase of Streptomyces venezuelae, Strain=ATCC 15068, one page, last updated 2020 (Year: 2020).
Q8KRX6_9ACTN, the sequence of the SAM-dependent methyltransferase of Streptomyces narbonesis, NCBI_TaxID= 67333, last updated 2019 as version 41 (Year: 2019).
Seo et al., "A Three Dimensional Nanostructured Array of Protein Nanoparticle," Adv. Funct. Mater. 20, 4055-4061 (2010).
UNIPROT Q8KRX6, "The desosamine biosynthetic cluster of Streptomyces narbonensi, producer of narbomycin," Bate and Cundliff, 2002, one page, version 1, obtained from the Internet Oct. 9, 2020 from www.uniprot.org website (Year: 2002).
Boyington et al., "Structure-Based Design of Head-Only Fusion Glycoprotein Immunogens for Respiratory Synctial Virus." PLoS One 11(7): e0159709 (2016).

(56) References Cited

OTHER PUBLICATIONS

Deng et al., "Double-layered protein nanoparticles induce broad protection against divergenet influenza A viruses" Nat Commun 359(9): 1-12 (2018).

Jones et. al., "A Method for Producing Protein Nanoparticles with Applications in Vaccines," PLoS One 11(3): e0138761 (2016).

Kaba et al., "Self-assembling protein nanoparticles with built-in flagellin domains increases protective efficacy of a Plasmodium falciparum based vaccine" Vaccine 36(6): 906-914 (2018).

Lopez-Sagaseta et al., "Self-assembling protein nanoparticles in the design of vaccines" Comp Struct Biotechnot J. 14:58-68 (2015).

Phippen et al., "Multivalent Display of Antifreeze Proteins by Fusion to Self-Assembling Protein Cages Enhances Ice-Binding Activiteis," Biochemistry 55:490 6811-6820 (2016).

Remot et al., "Nucleoprotein nanostructures combined with adjuvants adapted to the neonatal immune context: a candidate mucosal RSV vaccine." PLoS One 7(5): e37722 (2012).

Shu et al., Hemagglutinin partial [Influenza A virus (A/California/07/2009 (H 1 N 1))]. Gen Bank: ACP41953.1, Dep. Jun. 1, 2009 (2009).

Tramuto et al., Hemagglutinin, partial [Influenza B Virus (B/Palermo/4/2013)]. Gen Bank AM B72169.1, Dep. May 11, 2016 (2016).

Vottler et al., "Designed proteins induce the formation of nanocage-containing extracellular vesicles," Nature 640 (6732): 292-295 (2016).

SEQUENCE LISTING

```
Sequence total quantity: 101
SEQ ID NO: 1              moltype = AA  length = 207
FEATURE                   Location/Qualifiers
REGION                    1..207
                          note = I53-34A
VARIANT                   1
                          note = optionally absent
source                    1..207
                          mol_type = protein
                          organism = synthetic construct
SEQUENCE: 1
MEGMDPLAVL AESRLLPLLT VRGGEDLAGL ATVLELMGVG ALEITLRTEK GLEALKALRK   60
SGLLLGAGTV RSPKEAEAAL EAGAAFLVSP GLLEEVAALA QARGVPYLPG VLTPTEVERA  120
LALGLSALKF FPAEPFQGVR VLRAYAEVFP EVRFLPTGGI KEEHLPHYAA LPNLLAVGGS  180
WLLQGDLAAV MKKVKAAKAL LSPQAPG                                     207

SEQ ID NO: 2              moltype = AA  length = 156
FEATURE                   Location/Qualifiers
REGION                    1..156
                          note = I53-34B
VARIANT                   1
                          note = optionally absent
source                    1..156
                          mol_type = protein
                          organism = synthetic construct
SEQUENCE: 2
MTKKVGIVDT TFARVDMAEA AIRTLKALSP NIKIIRKTVP GIKDLPVACK KLLEEEGCDI   60
VMALGMPGKA EKDKVCAHEA SLGLMLAQLM TNKHIIEVFV HEDEAKDDDE LDILALVRAI  120
EHAANVYYLL FKPEYLTRMA GKGLRQGRED AGPARE                           156

SEQ ID NO: 3              moltype = AA  length = 156
FEATURE                   Location/Qualifiers
REGION                    1..156
                          note = I53-40A
VARIANT                   1
                          note = optionally absent
```

```
                              source           1..156
                                               mol_type = protein
                                               organism = synthetic construct
SEQUENCE: 3
MTKKVGIVDT  TFARVDMASA  AILTLKMESP  NIKIIRKTVP  GIKDLPVACK  KLLEEEGCDI   60
VMALGMPGKA  EKDKVCAHEA  SLGLMLAQLM  TNKHIIEVFV  HEDEAKDDAE  LKILAARRAI  120
EHALNVYYLL  FKPEYLTRMA  GKGLRQGFED  AGPARE                              156

SEQ ID NO: 4      moltype = AA  length = 209
FEATURE           Location/Qualifiers
REGION            1..209
                  note = I53-40B
VARIANT           1
                  note = optionally absent
source            1..209
                  mol_type = protein
                  organism = synthetic construct
SEQUENCE: 4
MSTINNQLKA  LKVIPVIAID  NAEDIIPLGK  VLAENGLPAA  EITFRSSAAV  KAIMLLRSAQ   60
PEMLIGAGTI  LNGVQALAAK  EAGATFVVSP  GFNPNTVRAC  QIIGIDIVPG  VNNPSTVEAA  120
LEMGLTTLKF  FPAEASGGIS  MVKSLVGPYG  DIRLMPTGGI  TPSNIDNYLA  IPQVLACGGT  180
WMVDKKLVTN  GEWDEIARLT  REIVEQVNP                                      209

SEQ ID NO: 5      moltype = AA  length = 114
FEATURE           Location/Qualifiers
REGION            1..114
                  note = I53-47A
VARIANT           1
                  note = optionally absent
source            1..114
                  mol_type = protein
                  organism = synthetic construct
SEQUENCE: 5
MPIFTLNTNI  KATDVPSDFL  SLTSRLVGLI  LSKPGSYVAV  HINTDQQLSF  GGSTNPAAFG   60
TLMSIGGIEP  SKNRDHSAVL  FDHLNAMLGI  PKNRMYIHFV  NLNGDDVGWN  GTTF        114

SEQ ID NO: 6      moltype = AA  length = 157
FEATURE           Location/Qualifiers
REGION            1..157
                  note = I53-47B
VARIANT           1
                  note = optionally absent
source            1..157
                  mol_type = protein
                  organism = synthetic construct
SEQUENCE: 6
MNQHSHKDYE  TVRIAVVRAR  WHADIVDACV  EAFEIAMAAI  GGDRFAVDVF  DVPGAYEIPL   60
HARTLAETGR  YGAVLGTAFV  VNGGIYRHEF  VASAVIDGMM  NVQLSTGVPV  LSAVLTPHRY  120
RDSAEHHRFF  AAHFAVKGVE  AARACIEILA  AREKIAA                            157

SEQ ID NO: 7      moltype = AA  length = 205
FEATURE           Location/Qualifiers
REGION            1..205
                  note = I53-50A
VARIANT           1
                  note = optionally absent
source            1..205
                  mol_type = protein
                  organism = synthetic construct
SEQUENCE: 7
MKMEELFKKH  KIVAVLRANS  VEEAIEKAVA  VFAGGVHLIE  ITFTVPDADT  VIKALSVLKE   60
KGAIIGAGTV  TSVEQCRKAV  ESGAEFIVSP  HLDEEISQFC  KEKGVFYMPG  VMTPTELVKA  120
MKLGHTILKL  FPGEVVGPQF  VKAMKGPFPN  VKFVPTGGVN  LDNVCEWFKA  GVLAVGVGSA  180
LVKGTPDEVR  EKAKAFVEKI  RGCTE                                          205

SEQ ID NO: 8      moltype = AA  length = 157
FEATURE           Location/Qualifiers
REGION            1..157
                  note = I53-50B
VARIANT           1
                  note = optionally absent
source            1..157
                  mol_type = protein
                  organism = synthetic construct
SEQUENCE: 8
MNQHSHKDYE  TVRIAVVRAR  WHAEIVDACV  SAFEAAMADI  GGDRFAVDVF  DVPGAYEIPL   60
HARTLAETGR  YGAVLGTAFV  VNGGIYRHEF  VASAVIDGMM  NVQLSTGVPV  LSAVLTPHRY  120
RDSDAHTLLF  LALFAVKGME  AARACVEILA  AREKIAA                            157
```

```
SEQ ID NO: 9              moltype = AA   length = 177
FEATURE                   Location/Qualifiers
REGION                    1..177
                          note = I53-51A
VARIANT                   1
                          note = optionally absent
source                    1..177
                          mol_type = protein
                          organism = synthetic construct
SEQUENCE: 9
MFTKSGDDGN TNVINKRVGK DSPLVNFLGD LDELNSFIGF AISKIPWEDM KKDLERVQVE    60
LFEIGEDLST QSSKKKIDES YVLWLLAATA IYRIESGPVK LFVIPGGSEE ASVLHVTRSV   120
ARRVERNAVK YTKELPEINR MIIVYLNRLS SLLFAMALVA NKRRNQSEKI YEIGKSW     177

SEQ ID NO: 10             moltype = AA   length = 157
FEATURE                   Location/Qualifiers
REGION                    1..157
                          note = I53-51B
VARIANT                   1
                          note = optionally absent
source                    1..157
                          mol_type = protein
                          organism = synthetic construct
SEQUENCE: 10
MNQHSHKDYE TVRIAVVRAR WHADIVDQCV RAFEEAMADA GGDRFAVDVF DVPGAYEIPL    60
HARTLAETGR YGAVLGTAFV VNGGIYRHEF VASAVIDGMM NVQLSTGVPV LSAVLTPHRY   120
RSSREHHEFF REHFMVKGVE AAAACITILA AREKIAA                             157

SEQ ID NO: 11             moltype = AA   length = 201
FEATURE                   Location/Qualifiers
REGION                    1..201
                          note = I52-03A
VARIANT                   1
                          note = optionally absent
source                    1..201
                          mol_type = protein
                          organism = synthetic construct
SEQUENCE: 11
MGHTKGPTPQ QHDGSALRIG IVHARWNKTI IMPLLIGTIA KLLECGVKAS NIVVQSVPGS    60
WELPIAVQRL YSASQLQTPS SGPSLSAGDL LGSSTTDLTA LPTTTASSTG PPDALIAIGV   120
LIKGETMHFE YIADSVSHGL MRVQLDTGVP VIFGVLTVLT DDQAKARAGV IEGSHNHGED   180
WGLAAVEMGV RRRDWAAGKT E                                              201

SEQ ID NO: 12             moltype = AA   length = 237
FEATURE                   Location/Qualifiers
REGION                    1..237
                          note = I52-03B
VARIANT                   1
                          note = optionally absent
source                    1..237
                          mol_type = protein
                          organism = synthetic construct
SEQUENCE: 12
MYEVDHADVY DLFYLGRGKD YAAEASDIAD LVRSRTPEAS SLLDVACGTG THLEHFTKEF    60
GDTAGLELSE DMLTHARKRL PDATLHQGDM RDFQLGRKFS AVVSMFSSVG YLKTVAELGA   120
AVASFAEHLE PGGVVVVEPW WFPETFADGW VSADVVRRDG RTVARVSHSV REGNATRMEV   180
HFTVADPGKG VRHFSDVHLI TLFHQREYEA AFMAAGLRVE YLEGGPSGRG LFVGVPA      237

SEQ ID NO: 13             moltype = AA   length = 138
FEATURE                   Location/Qualifiers
REGION                    1..138
                          note = I52-32A
VARIANT                   1
                          note = optionally absent
source                    1..138
                          mol_type = protein
                          organism = synthetic construct
SEQUENCE: 13
MGMKEKFVLI ITHGDFGKGL LSGAEVIIGK QENVHTVGLN LGDNIEKVAK EVMRIIIAKL    60
AEDKEIIIVV DLFGGSPFNI ALEMMKTFDV KVITGINMPM LVELLTSINV YDTTELLENI   120
SKIGKDGIKV IEKSSLKM                                                  138

SEQ ID NO: 14             moltype = AA   length = 154
FEATURE                   Location/Qualifiers
REGION                    1..154
                          note = I52-32B
VARIANT                   1
                          note = optionally absent
source                    1..154
```

```
                              mol_type = protein
                              organism = synthetic construct
SEQUENCE: 14
MKYDGSKLRI GILHARWNLE IIAALVAGAI KRLQEFGVKA ENIIIETVPG SFELPYGSKL     60
FVEKQKRLGK PLDAIIPIGV LIKGSTMHFE YICDSTTHQL MKLNFELGIP VIFGVLTCLT    120
DEQAEARAGL IEGKMHNHGE DWGAAAVEMA TKFN                                154

SEQ ID NO: 15                 moltype = AA  length = 164
FEATURE                       Location/Qualifiers
REGION                        1..164
                              note = I52-33A
VARIANT                       1
                              note = optionally absent
source                        1..164
                              mol_type = protein
                              organism = synthetic construct
SEQUENCE: 15
MAVKGLGEVD QKYDGSKLRI GILHARWNRK IILALVAGAV LRLLEFGVKA ENIIIETVPG     60
SFELPYGSKL FVEKQKRLGK PLDAIIPIGV LIKGSTMHFE YICDSTTHQL MKLNFELGIP    120
VIFGVLTCLT DEQAEARAGL IEGKMHNHGE DWGAAAVEMA TKFN                     164

SEQ ID NO: 16                 moltype = AA  length = 175
FEATURE                       Location/Qualifiers
REGION                        1..175
                              note = I52-33B
VARIANT                       1
                              note = optionally absent
source                        1..175
                              mol_type = protein
                              organism = synthetic construct
SEQUENCE: 16
MGANWYLDNE SSRLSFTSTK NADIAEVHRF LVLHGKVDPK GLAEVEVETE SISTGIPLRD     60
MLLRVLVFQV SKFPVAQINA QLDMRPINNL APGAQLELRL PLTVSLRGKS HSYNAELLAT    120
RLDERRFQVV TLEPLVIHAQ DFDMVRAFNA LRLVAGLSAV SLSVPVGAVL IFTAR         175

SEQ ID NO: 17                 moltype = AA  length = 208
FEATURE                       Location/Qualifiers
REGION                        1..208
                              note = I32-06A
VARIANT                       1
                              note = optionally absent
source                        1..208
                              mol_type = protein
                              organism = synthetic construct
SEQUENCE: 17
MTDYIRDGSA IKALSFAIIL AEADLRHIPQ DLQRLAVRVI HACGMVDVAN DLAFSEGAGK     60
AGRNALLAGA PILCDARMVA EGITRSRLPA DNRVIYTLSD PSVPELAKKI GNTRSAAALD    120
LWLPHIEGSI VAIGNAPTAL FRLFELLDAG APKPALIIGM PVGFVGAAES KDELAANSRG    180
VPYVIVRGRR GGSAMTAAAV NALASERE                                       208

SEQ ID NO: 18                 moltype = AA  length = 128
FEATURE                       Location/Qualifiers
REGION                        1..128
                              note = I32-06B
VARIANT                       1
                              note = optionally absent
source                        1..128
                              mol_type = protein
                              organism = synthetic construct
SEQUENCE: 18
MITVFGLKSK LAPRREKLAE VIYSSLHLGL DIPKGKHAIR FLCLEKEDFY YPFDRSDDYT     60
VIEINLMAGR SEETKMLLIF LLFIALERKL GIRAHDVEIT IKEQPAHCWG FRGRTGDSAR    120
DLDYDIYV                                                             128

SEQ ID NO: 19                 moltype = AA  length = 235
FEATURE                       Location/Qualifiers
REGION                        1..235
                              note = I32-19A
VARIANT                       1
                              note = optionally absent
source                        1..235
                              mol_type = protein
                              organism = synthetic construct
SEQUENCE: 19
MGSDLQKLQR FSTCDISDGL LNVYNIPTGG YFPNLTAISP PQNSSIVGTA YTVLFAPIDD     60
PRPAVNYIDS VPPNSILVLA LEPHLQSQFH PFIKITQAMY GGLMSTRAQY LKSNGTVVFG    120
RIRDVDEHRT LNHPVFAYGV GSCAPKAVVK AVGTNVQLKI LTSDGVTQTI CPGDYIAGDN    180
NGIVRIPVQE TDISKLVTYI EKSIEVDRLV SEAIKNGLPA KAAQTARRMV LKDYI         235
```

-continued

```
SEQ ID NO: 20              moltype = AA  length = 162
FEATURE                    Location/Qualifiers
REGION                     1..162
                           note = I32-19B
VARIANT                    1
                           note = optionally absent
source                     1..162
                           mol_type = protein
                           organism = synthetic construct
SEQUENCE: 20
MSGMRVYLGA DHAGYELKQA IIAFLKMTGH EPIDCGALRY DADDDYPAFC IAAATRTVAD    60
PGSLGIVLGG SGNGEQIAAN KVPGARCALA WSVQTAALAR EHNNAQLIGI GGRMHTLEEA   120
LRIVKAFVTT PWSKAQRHQR RIDILAEYER THEAPPVPGA PA                     162

SEQ ID NO: 21              moltype = AA  length = 157
FEATURE                    Location/Qualifiers
REGION                     1..157
                           note = I32-28A
VARIANT                    1
                           note = optionally absent
source                     1..157
                           mol_type = protein
                           organism = synthetic construct
SEQUENCE: 21
MGDDARIAAI GDVDELNSQI GVLLAEPLPD DVRAALSAIQ HDLFDLGGEL CIPGHAAITE    60
DHLLRLALWL VHYNGQLPPL EEFILPGGAR GAALAHVCRT VCRRAERSIK ALGASEPLNI   120
APAAYVNLLS DLLFVLARVL NRAAGGADVL WDRTRAH                            157

SEQ ID NO: 22              moltype = AA  length = 157
FEATURE                    Location/Qualifiers
REGION                     1..157
                           note = I32-28B
VARIANT                    1
                           note = optionally absent
source                     1..157
                           mol_type = protein
                           organism = synthetic construct
SEQUENCE: 22
MILSAEQSFT LRHPHGQAAA LAFVREPAAA LAGVQRLRGL DSDGEQVWGE LLVRVPLLGE    60
VDLPFRSEIV RTPQGAELRP LTLTGERAWV AVSGQATAAE GGEMAFAFQF QAHLATPEAE   120
GEGGAAFEVM VQAAAGVTLL LVAMALPQGL AAGLPPA                            157

SEQ ID NO: 23              moltype = AA  length = 156
FEATURE                    Location/Qualifiers
REGION                     1..156
                           note = I53-40A.1
VARIANT                    1
                           note = optionally absent
source                     1..156
                           mol_type = protein
                           organism = synthetic construct
SEQUENCE: 23
MTKKVGIVDT TFARVDMASA AILTLKMESP NIKIIRKTVP GIKDLPVACK KLLEEEGCDI    60
VMALGMPGKK EKDKVCAHEA SLGLMLAQLM TNKHIIEVFV HEDEAKDDAE LKILAARRAI   120
EHALNVYYLL FKPEYLTRMA GKGLRQGFED AGPARE                             156

SEQ ID NO: 24              moltype = AA  length = 209
FEATURE                    Location/Qualifiers
REGION                     1..209
                           note = I53-40B.1
VARIANT                    1
                           note = optionally absent
source                     1..209
                           mol_type = protein
                           organism = synthetic construct
SEQUENCE: 24
MDDINNQLKR LKVIPVIAID NAEDIIPLGK VLAENGLPAA EITFRSSAAV KAIMLLRSAQ    60
PEMLIGAGTI LNGVQALAAK EAGADFVVSP GFNPNTVRAC QIIGIDIVPG VNNPSTVEQA   120
LEMGLTTLKF FPAEASGGIS MVKSLVGPYG DIRLMPTGGI TPDNIDNYLA IPQVLACGGT   180
WMVDKKLVRN GEWDEIARLT REIVEQVNP                                     209

SEQ ID NO: 25              moltype = AA  length = 114
FEATURE                    Location/Qualifiers
REGION                     1..114
                           note = I53-47A.1
VARIANT                    1
                           note = optionally absent
source                     1..114
                           mol_type = protein
```

```
                                    -continued
                        organism    = synthetic construct
SEQUENCE: 25
MPIFTLNTNI KADDVPSDFL SLTSRLVGLI LSKPGSYVAV HINTDQQLSF GGSTNPAAFG      60
TLMSIGGIEP DKNRDHSAVL FDHLNAMLGI PKNRMYIHFV NLNGDDVGWN GTTF           114

SEQ ID NO: 26           moltype = AA   length = 114
FEATURE                 Location/Qualifiers
REGION                  1..114
                        note = I53-47A.1NegT2
VARIANT                 1
                        note = optionally absent
source                  1..114
                        mol_type = protein
                        organism = synthetic construct
SEQUENCE: 26
MPIFTLNTNI KADDVPSDFL SLTSRLVGLI LSEPGSYVAV HINTDQQLSF GGSTNPAAFG      60
TLMSIGGIEP DKNEDHSAVL FDHLNAMLGI PKNRMYIHFV DLDGDDVGWN GTTF           114

SEQ ID NO: 27           moltype = AA   length = 157
FEATURE                 Location/Qualifiers
REGION                  1..157
                        note = I53-47B.1
VARIANT                 1
                        note = optionally absent
source                  1..157
                        mol_type = protein
                        organism = synthetic construct
SEQUENCE: 27
MNQHSHKDHE TVRIAVVRAR WHADIVDACV EAFEIAMAAI GGDRFAVDVF DVPGAYEIPL      60
HARTLAETGR YGAVLGTAFV NGGIYRHEF VASAVIDGMM NVQLDTGVPV LSAVLTPHRY      120
RDSDEHHRFF AAHFAVKGVE AARACIEILN AREKIAA                             157

SEQ ID NO: 28           moltype = AA   length = 157
FEATURE                 Location/Qualifiers
REGION                  1..157
                        note = I53-47B.1NegT2
VARIANT                 1
                        note = optionally absent
source                  1..157
                        mol_type = protein
                        organism = synthetic construct
SEQUENCE: 28
MNQHSHKDHE TVRIAVVRAR WHADIVDACV EAFEIAMAAI GGDRFAVDVF DVPGAYEIPL      60
HARTLAETGR YGAVLGTAFV VDGGIYDHEF VASAVIDGMM NVQLDTGVPV LSAVLTPHEY      120
EDSDEDHEFF AAHFAVKGVE AARACIEILN AREKIAA                             157

SEQ ID NO: 29           moltype = AA   length = 205
FEATURE                 Location/Qualifiers
REGION                  1..205
                        note = I53-50A.1
VARIANT                 1
                        note = optionally absent
source                  1..205
                        mol_type = protein
                        organism = synthetic construct
SEQUENCE: 29
MKMEELFKKH KIVAVLRANS VEEAIEKAVA VFAGGVHLIE ITFTVPDADT VIKALSVLKE      60
KGAIIGAGTV TSVEQCRKAV ESGAEFIVSP HLDEEISQFC KEKGVFYMPG VMTPTELVKA    120
MKLGHDILKL FPGEVVGPQF VKAMKGPFPN VKFVPTGGVN LDNVCEWFKA GVLAVGVGDA    180
LVKGDPDEVR EKAKKFVEKI RGCTE                                          205

SEQ ID NO: 30           moltype = AA   length = 205
FEATURE                 Location/Qualifiers
REGION                  1..205
                        note = I53-50A.1NegT2
VARIANT                 1
                        note = optionally absent
source                  1..205
                        mol_type = protein
                        organism = synthetic construct
SEQUENCE: 30
MKMEELFKKH KIVAVLRANS VEEAIEKAVA VFAGGVHLIE ITFTVPDADT VIKALSVLKE      60
KGAIIGAGTV TSVEQCRKAV ESGAEFIVSP HLDEEISQFC KEKGVFYMPG VMTPTELVKA    120
MKLGHDILKL FPGEVVGPEF VEAMKGPFPN VKFVPTGGVD LDDVCEWFDA GVLAVGVGDA    180
LVEGDPDEVR EDAKEFVEEI RGCTE                                          205

SEQ ID NO: 31           moltype = AA   length = 205
FEATURE                 Location/Qualifiers
REGION                  1..205
```

```
                              note = I53-50A.1PosT1
VARIANT                       1
                              note = optionally absent
source                        1..205
                              mol_type = protein
                              organism = synthetic construct
SEQUENCE: 31
MKMEELFKKH KIVAVLRANS VEEAIEKAVA VFAGGVHLIE ITFTVPDADT VIKALSVLKE    60
KGAIIGAGTV TSVEQCRKAV ESGAEFIVSP HLDEEISQFC KEKGVFYMPG VMTPTELVKA  120
MKLGHDILKL FPGEVVGPQF VKAMKGPFPN VKFVPTGGVN LDNVCKWFKA GVLAVGVGKA  180
LVKGKPDEVR EKAKKFVKKI RGCTE                                      205

SEQ ID NO: 32                 moltype = AA  length = 157
FEATURE                       Location/Qualifiers
REGION                        1..157
                              note = I53-50B.1
VARIANT                       1
                              note = optionally absent
source                        1..157
                              mol_type = protein
                              organism = synthetic construct
SEQUENCE: 32
MNQHSHKDHE TVRIAVVRAR WHAEIVDACV SAFEAAMRDI GGDRFAVDVF DVPGAYEIPL   60
HARTLAETGR YGAVLGTAFV VNGGIYRHEF VASAVIDGMM NVQLDTGVPV LSAVLTPHRY  120
RDSDAHTLLF LALFAVKGME AARACVEILA AREKIAA                          157

SEQ ID NO: 33                 moltype = AA  length = 157
FEATURE                       Location/Qualifiers
REGION                        1..157
                              note = I53-50B.1NegT2
VARIANT                       1
                              note = optionally absent
source                        1..157
                              mol_type = protein
                              organism = synthetic construct
SEQUENCE: 33
MNQHSHKDHE TVRIAVVRAR WHAEIVDACV SAFEAAMRDI GGDRFAVDVF DVPGAYEIPL   60
HARTLAETGR YGAVLGTAFV VDGGIYDHEF VASAVIDGMM NVQLDTGVPV LSAVLTPHEY  120
EDSDADTLLF LALFAVKGME AARACVEILA AREKIAA                          157

SEQ ID NO: 34                 moltype = AA  length = 157
FEATURE                       Location/Qualifiers
REGION                        1..157
                              note = I53-50B.4PosT1
VARIANT                       1
                              note = optionally absent
source                        1..157
                              mol_type = protein
                              organism = synthetic construct
SEQUENCE: 34
MNQHSHKDHE TVRIAVVRAR WHAEIVDACV SAFEAAMRDI GGDRFAVDVF DVPGAYEIPL   60
HARTLAETGR YGAVLGTAFV VNGGIYRHEF VASAVINGMM NVQLNTGVPV LSAVLTPHNY  120
DKSKAHTLLF LALFAVKGME AARACVEILA AREKIAA                          157

SEQ ID NO: 35                 moltype = AA  length = 156
FEATURE                       Location/Qualifiers
REGION                        1..156
                              note = I53-40 A genus
VARIANT                       1
                              note = optionally absent
VARIANT                       70
                              note = Xaa is A or K
source                        1..156
                              mol_type = protein
                              organism = synthetic construct
SEQUENCE: 35
MTKKVGIVDT TFARVDMASA AILTLKMESP NIKIIRKTVP GIKDLPVACK KLLEEEGCDI   60
VMALGMPGKX EKDKVCAHEA SLGLMLAQLM TNKHIIEVFV HEDEAKDDAE LKILAARRAI  120
EHALNVYYLL FKPEYLTRMA GKGLRQGFED AGPARE                           156

SEQ ID NO: 36                 moltype = AA  length = 209
FEATURE                       Location/Qualifiers
REGION                        1..209
                              note = I53-40 B genus
VARIANT                       1
                              note = optionally absent
VARIANT                       2
                              note = Xaa is S or D
VARIANT                       3
```

```
                        note = Xaa is T or D
VARIANT                 10
                        note = Xaa is A or R
VARIANT                 85
                        note = Xaa is T or D
VARIANT                 119
                        note = Xaa is A or Q
VARIANT                 163
                        note = Xaa is S or D
VARIANT                 189
                        note = Xaa is T or R
source                  1..209
                        mol_type = protein
                        organism = synthetic construct
SEQUENCE: 36
MXXINNQLKX LKVIPVIAID NAEDIIPLGK VLAENGLPAA EITFRSSAAV KAIMLLRSAQ   60
PEMLIGAGTI LNGVQALAAK EAGAXFVVSP GFNPNTVRAC QIIGIDIVPG VNNPSTVEXA  120
LEMGLTTLKF FPAEASGGIS MVKSLVGPYG DIRLMPTGGI TPXNIDNYLA IPQVLACGGT  180
WMVDKKLVXN GEWDEIARLT REIVEQVNP                                   209

SEQ ID NO: 37           moltype = AA  length = 114
FEATURE                 Location/Qualifiers
REGION                  1..114
                        note = I53-47A genus
VARIANT                 1
                        note = optionally absent
VARIANT                 13
                        note = Xaa is T or D
VARIANT                 33
                        note = Xaa is K or E
VARIANT                 71
                        note = Xaa is S or D
VARIANT                 74
                        note = Xaa is R or E
VARIANT                 101
                        note = Xaa is N or D
VARIANT                 103
                        note = Xaa is N or D
source                  1..114
                        mol_type = protein
                        organism = synthetic construct
SEQUENCE: 37
MPIFTLNTNI KAXDVPSDFL SLTSRLVGLI LSXPGSYVAV HINTDQQLSF GGSTNPAAFG   60
TLMSIGGIEP XKNXDHSAVL FDHLNAMLGI PKNRMYIHFV XLXGDDVGWN GTTF        114

SEQ ID NO: 38           moltype = AA  length = 157
FEATURE                 Location/Qualifiers
REGION                  1..157
                        note = I53-47B genus
VARIANT                 1
                        note = optionally absent
VARIANT                 9
                        note = Xaa is Y or H
VARIANT                 82
                        note = Xaa is N or D
VARIANT                 87
                        note = Xaa is R or D
VARIANT                 105
                        note = Xaa is S or D
VARIANT                 119
                        note = Xaa is R or E
VARIANT                 121
                        note = Xaa is R or E
VARIANT                 124
                        note = Xaa is A or D
VARIANT                 126
                        note = Xaa is H or D
VARIANT                 128
                        note = Xaa is R or E
VARIANT                 150
                        note = Xaa is A or N
source                  1..157
                        mol_type = protein
                        organism = synthetic construct
SEQUENCE: 38
MNQHSHKDXE TVRIAVVRAR WHADIVDACV EAFEIAMAAI GGDRFAVDVF DVPGAYEIPL   60
HARTLAETGR YGAVLGTAFV VXGGIYXHEF VASAVIDGMM NVQLXTGPVP LSAVLTPHXY  120
XDSXEXHXFF AAHFAVKGVE AARACIEILX AREKIAA                           157
```

| | | |
|---|---|---|
| SEQ ID NO: 39 | moltype = AA length = 205 | |
| FEATURE | Location/Qualifiers | |
| REGION | 1..205 | |
| | note = I53-50A genus | |
| VARIANT | 1 | |
| | note = optionally absent | |
| VARIANT | 126 | |
| | note = Xaa is T or D | |
| VARIANT | 139 | |
| | note = Xaa is Q or E | |
| VARIANT | 142 | |
| | note = Xaa is K or E | |
| VARIANT | 160 | |
| | note = Xaa is N or D | |
| VARIANT | 163 | |
| | note = Xaa is N or D | |
| VARIANT | 166 | |
| | note = Xaa is E or K | |
| VARIANT | 169 | |
| | note = Xaa is D or K | |
| VARIANT | 179 | |
| | note = Xaa is S, D or K | |
| VARIANT | 183 | |
| | note = Xaa is K or E | |
| VARIANT | 185 | |
| | note = Xaa is T, D, or K | |
| VARIANT | 192 | |
| | note = Xaa is D or K | |
| VARIANT | 195 | |
| | note = Xaa is A, E, or K | |
| VARIANT | 198 | |
| | note = Xaa is E or K | |
| VARIANT | 199 | |
| | note = Xaa is E or K | |
| source | 1..205 | |
| | mol_type = protein | |
| | organism = synthetic construct | |
| SEQUENCE: 39 | | |
| MKMEELFKKH KIVAVLRANS VEEAIEKAVA VFAGGVHLIE ITFTVPDADT VIKALSVLKE | | 60 |
| KGAIIGAGTV TSVEQCRKAV ESGAEFIVSP HLDEEISQFC KEKGVFYMPG VMTPTELVKA | | 120 |
| MKLGHXILKL FPGEVVGPXF VXAMKGPFPN VKFVPTGGVX LDXVCXWFXA GVLAVGVGXA | | 180 |
| LVXGXPDEVR EXAKXFVXXI RGCTE | | 205 |
| | | |
| SEQ ID NO: 40 | moltype = AA length = 157 | |
| FEATURE | Location/Qualifiers | |
| REGION | 1..157 | |
| | note = I53-50B genus | |
| VARIANT | 1 | |
| | note = optionally absent | |
| VARIANT | 9 | |
| | note = Xaa is Y or H | |
| VARIANT | 38 | |
| | note = Xaa is A or R | |
| VARIANT | 82 | |
| | note = Xaa is N or D | |
| VARIANT | 87 | |
| | note = Xaa is R or D | |
| VARIANT | 97 | |
| | note = Xaa is N or D | |
| VARIANT | 105 | |
| | note = Xaa is S, N, or D | |
| VARIANT | 119 | |
| | note = Xaa is R, E, or N | |
| VARIANT | 121 | |
| | note = Xaa is R, E, or D | |
| VARIANT | 122 | |
| | note = Xaa is K or D | |
| VARIANT | 124 | |
| | note = Xaa is K or D | |
| VARIANT | 126 | |
| | note = Xaa is H or D | |
| source | 1..157 | |
| | mol_type = protein | |
| | organism = synthetic construct | |
| SEQUENCE: 40 | | |
| MNQHSHKDXE TVRIAVVRAR WHAEIVDACV SAFEAAMXDI GGDRFAVDVF DVPGAYEIPL | | 60 |
| HARTLAETGR YGAVLGTAFV VXGGIYXHEF VASAVIXGMM NVQLXTGVPV LSAVLTPHXY | | 120 |
| XXSXAXTLLF LALFAVKGME AARACVEILA AREKIAA | | 157 |

| | | |
|---|---|---|
| SEQ ID NO: 41 | moltype = AA length = 159 | |
| FEATURE | Location/Qualifiers | |
| REGION | 1..159<br>note = T32-28A | |
| VARIANT | 1<br>note = optionally absent | |
| source | 1..159<br>mol_type = protein<br>organism = synthetic construct | |

SEQUENCE: 41
```
MGEVPIGDPK ELNGMEIAAV YLQPIEMEPR GIDLAASLAD IHLEADIHAL KNNPNGFPEG   60
FWMPYLTIAY ALANADTGAI KTGTLMPMVA DDGPHYGANI AMEKDKKGGF GVGTYALTFL  120
ISNPEKQGFG RHVDEETGVG KWFEPFVVTY FFKYTGTPK                        159
```

| | | |
|---|---|---|
| SEQ ID NO: 42 | moltype = AA length = 184 | |
| FEATURE | Location/Qualifiers | |
| REGION | 1..184<br>note = T32-28B | |
| VARIANT | 1<br>note = optionally absent | |
| source | 1..184<br>mol_type = protein<br>organism = synthetic construct | |

SEQUENCE: 42
```
MSQAIGILEL TSIAKGMELG DAMLKSANVD LLVSKTISPG KFLLMLGGDI GAIQQAIETG   60
TSQAGEMLVD SLVLANIHPS VLPAISGLNS VDKRQAVGIV ETWSVAACIS AADLAVKGSN  120
VTLVRVHMAF GIGGKCYMVV AGDVLDVAAA VATASLAAGA KGLLVYASII PRPHEAMWRQ  180
MVEG                                                             184
```

| | | |
|---|---|---|
| SEQ ID NO: 43 | moltype = AA length = 103 | |
| FEATURE | Location/Qualifiers | |
| REGION | 1..103<br>note = T33-09A | |
| VARIANT | 1<br>note = optionally absent | |
| source | 1..103<br>mol_type = protein<br>organism = synthetic construct | |

SEQUENCE: 43
```
MEEVVLITVP SALVAVKIAH ALVEERLAAC VNIVPGLTSI YRWQGSVVSD HELLLLVKTT   60
THAFPKLKER VKALHPYTVP EIVALPIAEG NREYLDWLRE NTG                   103
```

| | | |
|---|---|---|
| SEQ ID NO: 44 | moltype = AA length = 122 | |
| FEATURE | Location/Qualifiers | |
| REGION | 1..122<br>note = T33-09B | |
| VARIANT | 1<br>note = optionally absent | |
| source | 1..122<br>mol_type = protein<br>organism = synthetic construct | |

SEQUENCE: 44
```
MVRGIRGAIT VEEDTPAAIL AATIELLLKM LEANGIQSYE ELAAVIFTVT EDLTSAFPAE   60
AARLIGMHRV PLLSAREVPV PGSLPRVIRV LALWNTDTPQ DRVRHVYLNE AVRLRPDLES  120
AQ                                                               122
```

| | | |
|---|---|---|
| SEQ ID NO: 45 | moltype = AA length = 177 | |
| FEATURE | Location/Qualifiers | |
| REGION | 1..177<br>note = T33-15A | |
| VARIANT | 1<br>note = optionally absent | |
| source | 1..177<br>mol_type = protein<br>organism = synthetic construct | |

SEQUENCE: 45
```
MSKAKIGIVT VSDRASAGIT ADISGKAIIL ALNLYLTSEW EPIYQVIPDE QDVIETTLIK   60
MADEQDCCLI VTTGGTGPAK RDVTPEATEA VCDRMMPGFG ELMRAESLKE VPTAILSRQT  120
AGLRGDSLIV NLPGDPASIS DCLLAVFPAI PYCIDLMEGP YLECNEAMIK PFRPKAK    177
```

| | | |
|---|---|---|
| SEQ ID NO: 46 | moltype = AA length = 122 | |
| FEATURE | Location/Qualifiers | |
| REGION | 1..122<br>note = T33-15B | |
| VARIANT | 1<br>note = optionally absent | |
| source | 1..122<br>mol_type = protein<br>organism = synthetic construct | |

```
SEQUENCE: 46
MVRGIRGAIT VNSDTPTSII IATILLLEKM LEANGIQSYE ELAAVIFTVT EDLTSAFPAE    60
AARQIGMHRV PLLSAREVPV PGSLPRVIRV LALWNTDTPQ DRVRHVYLSE AVRLRPDLES   120
AQ                                                                  122

SEQ ID NO: 47            moltype = AA   length = 172
FEATURE                  Location/Qualifiers
REGION                   1..172
                         note = T33-21A
VARIANT                  1
                         note = optionally absent
source                   1..172
                         mol_type = protein
                         organism = synthetic construct
SEQUENCE: 47
MRITTKVGDK GSTRLFGGEE VWKDSPIIEA NGTLDELTSF IGEAKHYVDE EMKGILEEIQ    60
NDIYKIMGEI GSKGKIEGIS EERIAWLLKL ILRYMEMVNL KSFVLPGGTL ESAKLDVCRT   120
IARRALRKVL TVTREFGIGA EAAAYLLALS DLLFLLARVI EIEKNKLKEV RS           172

SEQ ID NO: 48            moltype = AA   length = 123
FEATURE                  Location/Qualifiers
REGION                   1..123
                         note = T33-21B
VARIANT                  1
                         note = optionally absent
source                   1..123
                         mol_type = protein
                         organism = synthetic construct
SEQUENCE: 48
MPHLVIEATA NLRLETSPGE LLEQANKALF ASGQFGEADI KSRFVTLEAY RQGTAAVERA    60
YLHACLSILD GRDIATRTLL GASLCAVLAE AVAGGGEEGV QVSVEVREME RLSYAKRVVA   120
RQR                                                                 123

SEQ ID NO: 49            moltype = AA   length = 158
FEATURE                  Location/Qualifiers
REGION                   1..158
                         note = T33-28A
VARIANT                  1
                         note = optionally absent
source                   1..158
                         mol_type = protein
                         organism = synthetic construct
SEQUENCE: 49
MESVNTSFLS PSLVTIRDFD NGQFAVLRIG RTGFPADKGD IDLCLDKMIG VRAAQIFLGD    60
DTEDGFKGPH IRIRCVDIDD KHTYNAMVYV DLIVGTGASE VERETAEEEA KLALRVALQV   120
DIADEHSCVT QFEMKLREEL LSSDSFHPDK DEYYKDFL                           158

SEQ ID NO: 50            moltype = AA   length = 113
FEATURE                  Location/Qualifiers
REGION                   1..113
                         note = T33-28B
VARIANT                  1
                         note = optionally absent
source                   1..113
                         mol_type = protein
                         organism = synthetic construct
SEQUENCE: 50
MPVIQTFVST PLDHHKRLLL AIIYRIVTRV VLGKPEDLVM MTFHDSTPMH FFGSTDPVAC    60
VRVEALGGYG PSEPEKVTSI VTAAITAVCG IVADRIFVLY FSPLHCGWNG TNF          113

SEQ ID NO: 51            moltype = AA   length = 103
FEATURE                  Location/Qualifiers
REGION                   1..103
                         note = T33-31A
VARIANT                  1
                         note = optionally absent
source                   1..103
                         mol_type = protein
                         organism = synthetic construct
SEQUENCE: 51
MEEVVLITVP SALVAVKIAH ALVEERLAAC VNIVPGLTSI YREEGSVVSD HELLLLVKTT    60
TDAFPKLKER VKELHPYEVP EIVALPIAEG NREYLDWLRE NTG                     103

SEQ ID NO: 52            moltype = AA   length = 7
FEATURE                  Location/Qualifiers
REGION                   1..7
                         note = Synthetic peptide
source                   1..7
                         mol_type = protein
```

```
                                        organism = synthetic construct
SEQUENCE: 52
QNITEEF                                                                                 7

SEQ ID NO: 53           moltype = AA   length = 513
FEATURE                 Location/Qualifiers
REGION                  1..513
                        note = DS-Cav1
VARIANT                 1..25
                        note = optionally absent
VARIANT                 508..513
                        note = optionally absent
source                  1..513
                        mol_type = protein
                        organism = synthetic construct
SEQUENCE: 53
MELLILKANA ITTILTAVTF CFASGQNITE EFYQSTCSAV SKGYLSALRT GWYTSVITIE        60
LSNIKENKCN GTDAKVKLIK QELDKYKNAV TELQLLMQST PATNNRARRE LPRFMNYTLN       120
NAKKTNVTLS KKRKRRFLGF LLGVGSAIAS GVAVCKVLHL EGEVNKIKSA LLSTNKAVVS       180
LSNGVSVLTF KVLDLKNYID KQLLPILNKQ SCSISNIETV IEFQQKNNRL LEITREFSVN       240
AGVTTPVSTY MLTNSELLSL INDMPITNDQ KKLMSNNVQI VRQQSYSIMC IIKEEVLAYV       300
VQLPLYGVID TPCWKLHTSP LCTTNTKEGS NICLTRTDRG WYCDNAGSVS FFPQAETCKV       360
QSNRVFCDTM NSLTLPSEVN LCNVDIFNPK YDCKIMTSKT DVSSSVITSL GAIVSCYGKT       420
KCTASNKNRG IIKTFSNGCD YVSNKGVDTV SVGNTLYYVN KQEGKSLYVK GEPIINFYDP       480
LVFPSDEFDA SISQVNEKIN QSLAFIRKSD ELL                                   513

SEQ ID NO: 54           moltype = AA   length = 27
FEATURE                 Location/Qualifiers
REGION                  1..27
                        note = T4 fibritin foldon domain
source                  1..27
                        mol_type = protein
                        organism = synthetic construct
SEQUENCE: 54
GYIPEAPRDG QAYVRKDGEW VLLSTFL                                           27

SEQ ID NO: 55           moltype = AA   length = 15
FEATURE                 Location/Qualifiers
REGION                  1..15
                        note = Linker
source                  1..15
                        mol_type = protein
                        organism = synthetic construct
SEQUENCE: 55
GSGGSGSGSG GSGSG                                                        15

SEQ ID NO: 56           moltype = AA   length = 8
FEATURE                 Location/Qualifiers
REGION                  1..8
                        note = Linker
source                  1..8
                        mol_type = protein
                        organism = synthetic construct
SEQUENCE: 56
GGSGGSGS                                                                 8

SEQ ID NO: 57           moltype = AA   length = 8
FEATURE                 Location/Qualifiers
REGION                  1..8
                        note = Linker
source                  1..8
                        mol_type = protein
                        organism = synthetic construct
SEQUENCE: 57
GSGGSGSG                                                                 8

SEQ ID NO: 58           moltype = AA   length = 11
FEATURE                 Location/Qualifiers
REGION                  1..11
                        note = Helical extension
source                  1..11
                        mol_type = protein
                        organism = synthetic construct
SEQUENCE: 58
EKAAKAEEAA R                                                            11

SEQ ID NO: 59           moltype = AA   length = 25
FEATURE                 Location/Qualifiers
REGION                  1..25
```

```
                           note = Signal peptide
source                     1..25
                           mol_type = protein
                           organism = synthetic construct
SEQUENCE: 59
MELLILKANA ITTILTAVTF CFASG                                             25

SEQ ID NO: 60              moltype = AA  length = 540
FEATURE                    Location/Qualifiers
REGION                     1..540
                           note = DS-Cav1-foldon
VARIANT                    1..25
                           note = optionally absent
source                     1..540
                           mol_type = protein
                           organism = synthetic construct
SEQUENCE: 60
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLGYIPEAP RDGQAYVRKD GEWVLLSTFL   540

SEQ ID NO: 61              moltype = AA  length = 474
FEATURE                    Location/Qualifiers
REGION                     1..474
                           note = sc9-10 DS-Cav1 A149C Y458C
VARIANT                    1..25
                           note = optionally absent
VARIANT                    468..474
                           note = optionally absent
source                     1..474
                           mol_type = protein
                           organism = synthetic construct
SEQUENCE: 61
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATGSGSAIC SGVAVCKVLH   120
LEGEVNKIKS ALLSTNKAVV SLSNGVSVLT FKVLDLKNYI DKQLLPILNK QSCSISNIET   180
VIEFQQKNNR LLEITREFSV NAGVTTPVST YMLTNSELLS LINDMPITND QKKLMSNNVQ   240
IVRQQSYSIM CIIKEEVLAY VVQLPLYGVI DTPCWKLHTS PLCTTNTKEG SNICLTRTDR   300
GWYCDNAGSV SFFPQAETCK VQSNRVFCDT MNSRTLPSEV NLCNVDIFNP KYDCKIMTSK   360
TDVSSSVITS LGAIVSCYGK TKCTASNKNR GIIKTFSNGC DYVSNKGVDT VSVGNTLYCV   420
NKQEGKSLYV KGEPIINFYD PLVFPSDEFD ASISQVNEKI NQSLAFIRKS DELL         474

SEQ ID NO: 62              moltype = AA  length = 474
FEATURE                    Location/Qualifiers
REGION                     1..474
                           note = sc9-10 DS-Cav1 A149C Y458C S46G K465Q S215P E92D
VARIANT                    1..25
                           note = optionally absent
VARIANT                    468..474
                           note = optionally absent
source                     1..474
                           mol_type = protein
                           organism = synthetic construct
SEQUENCE: 62
MELLILKANA ITTILTAVTF CFASGQNITE EFYQSTCSAV SKGYLGALRT GWYTSVITIE    60
LSNIKENKCN GTDAKVKLIK QELDKYKNAV TDLQLLMQST PATGSGSAIC SGVAVCKVLH   120
LEGEVNKIKS ALLSTNKAVV SLSNGVSVLT FKVLDLKNYI DKQLLPILNK QSCSIPNIET   180
VIEFQQKNNR LLEITREFSV NAGVTTPVST YMLTNSELLS LINDMPITND QKKLMSNNVQ   240
IVRQQSYSIM CIIKEEVLAY VVQLPLYGVI DTPCWKLHTS PLCTTNTKEG SNICLTRTDR   300
GWYCDNAGSV SFFPQAETCK VQSNRVFCDT MNSRTLPSEV NLCNVDIFNP KYDCKIMTSK   360
TDVSSSVITS LGAIVSCYGK TKCTASNKNR GIIKTFSNGC DYVSNKGVDT VSVGNTLYCV   420
NKQEGQSLYV KGEPIINFYD PLVFPSDEFD ASISQVNEKI NQSLAFIRKS DELL         474

SEQ ID NO: 63              moltype = AA  length = 522
FEATURE                    Location/Qualifiers
REGION                     1..522
                           note = SC-DM (N67I, S215P)
VARIANT                    1..25
                           note = optionally absent
VARIANT                    486..522
                           note = optionally absent
source                     1..522
                           mol_type = protein
```

```
                        organism = synthetic construct
SEQUENCE: 63
MELLILKANA ITTILTAVTF CFASGQNITE EFYQSTCSAV SKGYLSALRT GWYTSVITIE    60
LSNIKKIKCN GTDAKIKLIK QELDKYKNAV TELQLLMQST PATNNQARGS GSGRSLGFLL   120
GVGSAIASGV AVSKVLHLEG EVNKIKSALL STNKAVVSLS NGVSVLTSKV LDLKNYIDKQ   180
LLPIVNKQSC SIPNIETVIE FQQKNNRLLE ITREFSVNAG VTTPVSTYML TNSELLSLIN   240
DMPITNDQKK LMSNNVQIVR QQSYSIMSII KEEVLAYVVQ LPLYGVIDTP CWKLHTSPLC   300
TTNTKEGSNI CLTRTDRGWY CDNAGSVSFF PQAETCKVQS NRVFCDTMNS LTLPSEVNLC   360
NVDIFNPKYD CKIMTSKTDV SSSVITSLGA IVSCYGKTKC TASNKNRGII KTFSNGCDYV   420
SNKGVDTVSV GNTLYYVNKQ EGKSLYVKGE PIINFYDPLV FPSDEFDASI SQVNEKINQS   480
LAFIRKSDEL LSAIGGYIPE APRDGQAYVR KDGEWVLLST FL                     522

SEQ ID NO: 64           moltype = AA  length = 522
FEATURE                 Location/Qualifiers
REGION                  1..522
                        note = SC-TM (N67I, S215P, and E487Q)
VARIANT                 1..25
                        note = optionally absent
VARIANT                 486..522
                        note = optionally absent
source                  1..522
                        mol_type = protein
                        organism = synthetic construct
SEQUENCE: 64
MELLILKANA ITTILTAVTF CFASGQNITE EFYQSTCSAV SKGYLSALRT GWYTSVITIE    60
LSNIKKIKCN GTDAKIKLIK QELDKYKNAV TELQLLMQST PATNNQARGS GSGRSLGFLL   120
GVGSAIASGV AVSKVLHLEG EVNKIKSALL STNKAVVSLS NGVSVLTSKV LDLKNYIDKQ   180
LLPIVNKQSC SIPNIETVIE FQQKNNRLLE ITREFSVNAG VTTPVSTYML TNSELLSLIN   240
DMPITNDQKK LMSNNVQIVR QQSYSIMSII KEEVLAYVVQ LPLYGVIDTP CWKLHTSPLC   300
TTNTKEGSNI CLTRTDRGWY CDNAGSVSFF PQAETCKVQS NRVFCDTMNS LTLPSEVNLC   360
NVDIFNPKYD CKIMTSKTDV SSSVITSLGA IVSCYGKTKC TASNKNRGII KTFSNGCDYV   420
SNKGVDTVSV GNTLYYVNKQ EGKSLYVKGE PIINFYDPLV FPSDQFDASI SQVNEKINQS   480
LAFIRKSDEL LSAIGGYIPE APRDGQAYVR KDGEWVLLST FL                     522

SEQ ID NO: 65           moltype = AA  length = 490
FEATURE                 Location/Qualifiers
REGION                  1..490
                        note = HMPV F protein, strain CAN97-83 (A2)
VARIANT                 1..18
                        note = optionally absent
source                  1..490
                        mol_type = protein
                        organism = synthetic construct
SEQUENCE: 65
MSWKVVIIFS LLITPQHGLK ESYLEESCST ITEGYLSVLR TGWYTNVFTL EVGDVENLTC    60
SDGPSLIKTE LDLTKSALRE LKTVSADQLA REEQIENPRQ SRFVLGAIAL GVATAAAVTA   120
GVAIAKTIRL ESEVTAIKNA LKTTNEAVST LGNGVRVLAT AVRELKDFVS KNLTRAINKN   180
KCDIDDLKMA VSFSQFNRRF LNVVRQFSDN AGITPAISLD LMTDAELARA VSNMPTSAGQ   240
IKLMLENRAM VRRKGFGILI GVYGSSVIYM VQLPIFGVID TPCWIVKAAP SCSGKKGNYA   300
CLLREDQGWY CQNAGSTVYY PNEKDCETRG DHVFCDTAAG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPIK FPEDQFNVAL DQVFENIENS QALVDQSNRI   480
LSSAEKGNTG                                                         490

SEQ ID NO: 66           moltype = AA  length = 490
FEATURE                 Location/Qualifiers
REGION                  1..490
                        note = HMPVF with A113C, A339C, T160F, I177L
VARIANT                 1..18
                        note = optionally absent
source                  1..490
                        mol_type = protein
                        organism = synthetic construct
SEQUENCE: 66
MSWKVVIIFS LLITPQHGLK ESYLEESCST ITEGYLSVLR TGWYTNVFTL EVGDVENLTC    60
SDGPSLIKTE LDLTKSALRE LKTVSADQLA REEQIENPRQ SRFVLGAIAL GVCTAAAVTA   120
GVAIAKTIRL ESEVTAIKNA LKTTNEAVST LGNGVRVLAF AVRELKDFVS KNLTRALNKN   180
KCDIDDLKMA VSFSQFNRRF LNVVRQFSDN AGITPAISLD LMTDAELARA VSNMPTSAGQ   240
IKLMLENRAM VRRKGFGILI GVYGSSVIYM VQLPIFGVID TPCWIVKAAP SCSGKKGNYA   300
CLLREDQGWY CQNAGSTVYY PNEKDCETRG DHVFCDTACG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPIK FPEDQFNVAL DQVFENIENS QALVDQSNRI   480
LSSAEKGNTG                                                         490

SEQ ID NO: 67           moltype = AA  length = 490
FEATURE                 Location/Qualifiers
REGION                  1..490
                        note = HMPV- F with A113C, A120C, A339C, T160F, I177L, and

```
VARIANT                 1..18
                        note = optionally absent
source                  1..490
                        mol_type = protein
                        organism = synthetic construct
SEQUENCE: 67
MSWKVVIIFS LLITPQHGLK ESYLEESCST ITEGYLSVLR TGWYTNVFTL EVGDVENLTC    60
SDGPSLIKTE LDLTKSALRE LKTVSADQLA REEQIENPRQ SRFVLGAIAL GVCTAAAVTC   120
GVAIAKTIRL ESEVTAIKNA LKTTNEAVST LGNGVRVLAF AVRELKDFVS KNLTRALNKN   180
KCDIDDLKMA VSFSQFNRRF LNVVRQFSDN AGITPAISLD LMTDAELARA VSNMPTSAGQ   240
IKLMLENRAM VRRKGFGILI GVYGSSVIYM VQLPIFGVID TPCWIVKAAP SCSGKKGNYA   300
CLLREDQGWY CQNAGSTVYY PNEKDCETRG DHVFCDTACG INVAEQSKEC NINISTTNYP   360
CKVSTGRHPI SMVALSPLGA LVACYKGVSC SIGSNRVGII KQLNKGCSYI TNQDADTVTI   420
DNTVYCLSKV EGEQHVIKGR PVSSSFDPIK FPEDQFNVAL DQVFENIENS QALVDQSNRI   480
LSSAEKGNTG                                                         490

SEQ ID NO: 68           moltype = AA  length = 542
FEATURE                 Location/Qualifiers
REGION                  1..542
                        note = 115-BV (A185P)
VARIANT                 1..18
                        note = optionally absent
VARIANT                 490..542
                        note = optionally absent
source                  1..542
                        mol_type = protein
                        organism = synthetic construct
SEQUENCE: 68
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKTIRL ESEVTAIKNA LKKTNEAVST LGNGVRVLAT AVRELKDFVS KNLTRAINKN   180
KCDIPDLKMA VSFSQFNRRF LNVVRQFSDN AGITPAISLD LMTDAELARA VSNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QALVDQSNRI   480
LSSAEKGNTS GRENLYFQGG GGSGYIPEAP RDGQAYVRKD GEWVLLSTFL GGIEGRHHHH   540
HH                                                                 542

SEQ ID NO: 69           moltype = AA  length = 646
FEATURE                 Location/Qualifiers
REGION                  1..646
                        note = DS-Cav1-foldon-T33-31A
VARIANT                 1..26
                        note = optionally absent
source                  1..646
                        mol_type = protein
                        organism = synthetic construct
SEQUENCE: 69
MELLILKANV IATILTAVTF CFASSQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLGYIPEAP RDGQAYVRKD GEWVLLSTFL   540
GGSMEEVVLI TVPSALVAVK IAHALVEERL AACVNIVPGL TSIYREEGSV VSDHELLLLV   600
KTTTDAFPKL KERVKELHPY EVPEIVALPI AEGNREYLDW LRENTG                 646

SEQ ID NO: 70           moltype = AA  length = 619
FEATURE                 Location/Qualifiers
REGION                  1..619
                        note = DS-Cav1-T33-31A
VARIANT                 1..25
                        note = optionally absent
source                  1..619
                        mol_type = protein
                        organism = synthetic construct
SEQUENCE: 70
MELLILKANV IATILTAVTF CFASSQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
```

```
LVFPSDEFDA SISQVNEKIN QSLAFIRKSD ELLGGSMEEV VLITVPSALV AVKIAHALVE   540
ERLAACVNIV PGLTSIYREE GSVVSDHELL LLVKTTTDAF PKLKERVKEL HPYEVPEIVA   600
LPIAEGNREY LDWLRENTG                                                619

SEQ ID NO: 71           moltype = AA  length = 665
FEATURE                 Location/Qualifiers
REGION                  1..665
                        note = DS-Cav1-foldon-T33-15B
VARIANT                 1..25
                        note = optionally absent
source                  1..665
                        mol_type = protein
                        organism = synthetic construct
SEQUENCE: 71
MELLILKANV IATILTAVTF CFASSQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLGYIPEAP RDGQAYVRKD GEWVLLSTFL   540
GGSMVRGIRG AITVNSDTPT SIIIATILLL EKMLEANGIQ SYEELAAVIF TVTEDLTSAF   600
PAEAARQIGM HRVPLLSARE VPVPGSLPRV IRVLALWNTD TPQDRVRHVY LSEAVRLRPD   660
LESAQ                                                              665

SEQ ID NO: 72           moltype = AA  length = 638
FEATURE                 Location/Qualifiers
REGION                  1..638
                        note = DS-Cav1-T33-15B
VARIANT                 1..25
                        note = optionally absent
source                  1..638
                        mol_type = protein
                        organism = synthetic construct
SEQUENCE: 72
MELLILKANV IATILTAVTF CFASSQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLGGSMVRG IRGAITVNSD TPTSIIIATI   540
LLLEKMLEAN GIQSYEELAA VIFTVTEDLT SAFPAEAARQ IGMHRVPLLS AREVPVPGSL   600
PRVIRVLALW NTDTPQDRVR HVYLSEAVRL RPDLESAQ                           638

SEQ ID NO: 73           moltype = AA  length = 769
FEATURE                 Location/Qualifiers
REGION                  1..769
                        note = DS-Cav1-foldon-I53-50A
VARIANT                 1..25
                        note = optionally absent
source                  1..769
                        mol_type = protein
                        organism = synthetic construct
SEQUENCE: 73
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGYI PEAPRDGQAY VRKDGEWVLL STFLGSGSHH   540
HHHHHGGSG GSGSEKAAKA EEAARKMEEL FKKHKIVAVL RANSVEEAIE KAVAVFAGGV   600
HLIEITFTVP DADTVIKALS VLKEKGAIIG AGTVTSVEQC RKAVESGAEF IVSPHLDEEI   660
SQFCKEKGVF YMPGVMTPTE LVKAMKLGHT ILKLFPGEVV GPQFVKAMKG PFPNVKFVPT   720
GGVNLDNVCE WFKAGVLAVG VGSALVKGTP DEVREKAKAF VEKIRGCTE               769

SEQ ID NO: 74           moltype = AA  length = 730
FEATURE                 Location/Qualifiers
REGION                  1..730
                        note = DS-Cav1-I53-50A
VARIANT                 1..25
                        note = optionally absent
```

```
source                     1..730
                           mol_type = protein
                           organism = synthetic construct
SEQUENCE: 74
MELLILKANV IATILTAVTF CFASSQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGGS GGSGSEKAAK AEEEAARKMEE LFKKHKIVAV   540
LRANSVEEAI EKAVAVFAGG VHLIEITFTV PDADTVIKAL SVLKEKGAII GAGTVTSVEQ   600
CRKAVESGAE FIVSPHLDEE ISQFCKEKGV FYMPGVMTPT ELVKAMKLGH TILKLFPGEV   660
VGPQFVKAMK GPFPNVKFVP TGGVNLDNVC EWFKAGVLAV GVGSALVKGT PDEVREKAKA   720
FVEKIRGCTE                                                          730

SEQ ID NO: 75              moltype = AA   length = 676
FEATURE                    Location/Qualifiers
REGION                     1..676
                           note = DS-Cav1-I32-28A
VARIANT                    1..25
                           note = optionally absent
source                     1..676
                           mol_type = protein
                           organism = synthetic construct
SEQUENCE: 75
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLGGSGGSG SDDARIAAIG DVDELNSQIG   540
VLLAEPLPDD VRAALSAIQH DLFDLGGELC IPGHAAITED HLLRLALWLV HYNGQLPPLE   600
EFILPGGARG AALAHVCRTV CRRAERSIKA LGASEPLNIA PAAYVNLLSD LLFVLARVLN   660
RAAGGADVLW DRTRAH                                                   676

SEQ ID NO: 76              moltype = AA   length = 730
FEATURE                    Location/Qualifiers
REGION                     1..730
                           note = DS-Cav1-8GS-HelExt-I53-50A (F10)
VARIANT                    1..25
                           note = optionally absent
source                     1..730
                           mol_type = protein
                           organism = synthetic construct
SEQUENCE: 76
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGSG GSGSEKAAK AEEEAARKMEE LFKKHKIVAV   540
LRANSVEEAI EKAVAVFAGG VHLIEITFTV PDADTVIKAL SVLKEKGAII GAGTVTSVEQ   600
CRKAVESGAE FIVSPHLDEE ISQFCKEKGV FYMPGVMTPT ELVKAMKLGH TILKLFPGEV   660
VGPQFVKAMK GPFPNVKFVP TGGVNLDNVC EWFKAGVLAV GVGSALVKGT PDEVREKAKA   720
FVEKIRGCTE                                                          730

SEQ ID NO: 77              moltype = AA   length = 764
FEATURE                    Location/Qualifiers
REGION                     1..764
                           note = DS-Cav1-foldon-15GS-HelExt-I53-50A (F14)
VARIANT                    1..25
                           note = optionally absent
source                     1..764
                           mol_type = protein
                           organism = synthetic construct
SEQUENCE: 77
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
```

```
AGVTTPVSTY MLTNSELLSL INDMPITNDQ KKLMSNNVQI VRQQSYSIMC IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRGYI PEAPRDGQAY VRKDGEWVLL STFLGSGGSG  540
SGSGGSGSGE KAAKAEEAAR KMEELFKKHK IVAVLRANSV EEAIEKAVAV FAGGVHLIEI  600
TFTVPDADTV IKALSVLKEK GAIIGAGTVT SVEQCRKAVE SGAEFIVSPH LDEEISQFCK  660
EKGVFYMPGV MTPTELVKAM KLGHTILKLF PGEVVGPQFV KAMKGPFPNV KFVPTGGVNL  720
DNVCEWFKAG VLAVGVGSAL VKGTPDEVRE KAKAFVEKIR GCTE                  764

SEQ ID NO: 78              moltype = AA   length = 774
FEATURE                    Location/Qualifiers
REGION                     1..774
                           note = HMPV F wt_CAN97-83 strain-I53-50A
VARIANT                    1..18
                           note = optionally absent
source                     1..774
                           mol_type = protein
                           organism = synthetic construct
SEQUENCE: 78
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPRQ SRFVLGAIAL GVATAAAVTA  120
GVAIAKTIRL ESEVTAIKNA LKTTNEAVST LGNGVRVLAT AVRELKDFVS KNLTRAINKN  180
KCDIDDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSGKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFNVAL DQVFENIENS QALVDQSNRI  480
LSSAEKGNTG FIIVIILIAV LGSSMILVSI FIIIKKTKKP TGAPPELSGV TNNGFIPHSG  540
SGSHHHHHH HGGSGGSGSE KAAKAEEAAR KMEELFKKHK IVAVLRANSV EEAIEKAVAV  600
FAGGVHLIEI TFTVPDADTV IKALSVLKEK GAIIGAGTVT SVEQCRKAVE SGAEFIVSPH  660
LDEEISQFCK EKGVFYMPGV MTPTELVKAM KLGHTILKLF PGEVVGPQFV KAMKGPFPNV  720
KFVPTGGVNL DNVCEWFKAG VLAVGVGSAL VKGTPDEVRE KAKAFVEKIR GCTE        774

SEQ ID NO: 79              moltype = AA   length = 725
FEATURE                    Location/Qualifiers
REGION                     1..725
                           note = HMPV F A113C_A339C_T160F_I177L-I53-50A
VARIANT                    1..18
                           note = optionally absent
source                     1..725
                           mol_type = protein
                           organism = synthetic construct
SEQUENCE: 79
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPRQ SRFVLGAIAL GVCTAAAVTA  120
GVAIAKTIRL ESEVTAIKNA LKTTNEAVST LGNGVRVLAT AVRELKDFVS KNLTRALNKN  180
KCDIDDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSGKKGNYA  300
CLLREDQGWY CQNAGSTVYY PNEKDCETRG DHVFCDTACG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPIK FPEDQFNVAL DQVFENIENS QALVDQSNRI  480
LSSAEKGNTG GSSHHHHHH HHGGSGGSGS EKAAKAEEAA RKMEELFKKH KIVAVLRANS  540
VEEAIEKAVA VFAGGVHLIE ITFTVPDADT VIKALSVLKE KGAIIGAGTV TSVEQCRKAV  600
ESGAEFIVSP HLDEEISQFC KEKGVFYMPG VMTPTELVKA MKLGHTILKL FPGEVVGPQF  660
VKAMKGPFPN VKFVPTGGVN LDNVCEWFKA GVLAVGVGSA LVKGTPDEVR EKAKAFVEKI  720
RGCTE                                                              725

SEQ ID NO: 80              moltype = AA   length = 725
FEATURE                    Location/Qualifiers
REGION                     1..725
                           note = HMPV F A113C_A339C_T160F_I177L_A120C, Q426C - I53-50A
VARIANT                    1..18
                           note = optionally absent
source                     1..725
                           mol_type = protein
                           organism = synthetic construct
SEQUENCE: 80
MSWKVVIIFS LLITPQHGLK ESYLEESCST ITEGYLSVLR TGWYTNVFTL EVGDVENLTC  60
SDGPSLIKTE LDLTKSALRE LKTVSADQLA REEQIENPRQ SRFVLGAIAL GVCTAAAVTC  120
GVAIAKTIRL ESEVTAIKNA LKTTNEAVST LGNGVRVLAF AVRELKDFVS KNLTRALNKN  180
KCDIDDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSGKKGNYA  300
CLLREDQGWY CQNAGSTVYY PNEKDCETRG DHVFCDTACG INVAEQSKEC NINISTTNYP  360
CKVSTGRHPI SMVALSPLGA LVACYKGVSC SIGSNRVGII KQLNKGCSYI TNQDADTVTI  420
DNTVYCLSKV EGEQHVIKGR PVSSSFDPIK FPEDQFNVAL DQVFENIENS QALVDQSNRI  480
LSSAEKGNTG GSSHHHHHH HHGGSGGSGS EKAAKAEEAA RKMEELFKKH KIVAVLRANS  540
VEEAIEKAVA VFAGGVHLIE ITFTVPDADT VIKALSVLKE KGAIIGAGTV TSVEQCRKAV  600
ESGAEFIVSP HLDEEISQFC KEKGVFYMPG VMTPTELVKA MKLGHTILKL FPGEVVGPQF  660
```

```
VKAMKGPFPN VKFVPTGGVN LDNVCEWFKA GVLAVGVGSA LVKGTPDEVR EKAKAFVEKI    720
RGCTE                                                                725

SEQ ID NO: 81          moltype = AA  length = 703
FEATURE                Location/Qualifiers
REGION                 1..703
                       note = sc-DS2-I53-50A
VARIANT                1..25
                       note = optionally absent
source                 1..703
                       mol_type = protein
                       organism = synthetic construct
SEQUENCE: 81
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATGSGSCIA SGVAVCKVLH    120
LEGEVNKIKS ALLSTNKAVV SLSNGVSVLT FKVLDLKNYI DKQLLPILNK QSCSISNIET    180
VIEFQQKNNR LLEITREFSV NAGVTTPVST YMLTNSELLS LINDMPITND QKKLMSNNVQ    240
IVRQQSYSIM CIIKEEVLAY VVQLPLYGVI DTPCWKLHTS PLCTTNTKEG SNICLTRTDR    300
GWYCDNAGSV SFFPQAETCK VQSNRVFCDT MNSLTLPSEV NLCNVDIFNP KYDCKIMTSK    360
TDVSSSVITS LGAIVSCYGK TKCTASNKNR GIIKTFSNGC DYVSNKGVDT VSVGNTLYCV    420
NKQEGKSLYV KGEPIINFYD PLVFPSDEFD ASISQVNEKI NQSLAFIRGS GSHHHHHHHH    480
GGSGGSGSEK AAKAEEAARK MEELFKKHKI VAVLRANSVE EAIEKAVAVF AGGVHLIEIT    540
FTVPDADTVI KALSVLKEKG AIIGAGTVTS VEQCRKAVES GAEFIVSPHL DEEISQFCKE    600
KGVFYMPGVM TPTELVKAMK LGHTILKLFP GEVVGPQFVK AMKGPFPNVK FVPTGGVNLD    660
NVCEWFKAGV LAVGVGSALV KGTPDEVREK AKAFVEKIRG CTE                     703

SEQ ID NO: 82          moltype = AA  length = 742
FEATURE                Location/Qualifiers
REGION                 1..742
                       note = tc-DS2-I53-50A
VARIANT                1..25
                       note = optionally absent
source                 1..742
                       mol_type = protein
                       organism = synthetic construct
SEQUENCE: 82
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSCIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYCVN KQEGKSLYVK GEPIINFYDP    480
LVFPSDEFDA SISQVNEKIN QSLAFIRGSG SHHHHHHHG GSGGSGSEKA AKAEEAARKM    540
EELFKKHKIV AVLRANSVEE AIEKAVAVFA GGVHLIEITF TVPDADTVIK ALSVLKEKGA    600
IIGAGTVTSV EQCRKAVESG AEFIVSPHLD EEISQFCKEK GVFYMPGVMT PTELVKAMKL    660
GHTILKLFPG EVVGPQFVKA MKGPFPNVKF VPTGGVNLDN VCEWFKAGVL AVGVGSALVK    720
GTPDEVREKA KAFVEKIRGC TE                                            742

SEQ ID NO: 83          moltype = AA  length = 734
FEATURE                Location/Qualifiers
REGION                 1..734
                       note = DS-Cav1-12GS-HelExt-I53-50A (F11)
VARIANT                1..25
                       note = optionally absent
source                 1..734
                       mol_type = protein
                       organism = synthetic construct
SEQUENCE: 83
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN    120
NAKKTNVTLS KKRKRRFLGF LLGVGSAIAS GVAVCKVLHL EGEVNKIKSA LLSTNKAVVS    180
LSNGVSVLTF KVLDLKNYID KQLLPILNKQ SCSISNIETV IEFQQKNNRL LEITREFSVN    240
AGVTTPVSTY MLTNSELLSL INDMPITNDQ KKLMSNNVQI VRQQSYSIMC IIKEEVLAYV    300
VQLPLYGVID TPCWKLHTSP LCTTNTKEGS NICLTRTDRG WYCDNAGSVS FFPQAETCKV    360
QSNRVFCDTM NSLTLPSEVN LCNVDIFNPK YDCKIMTSKT DVSSSVITSL GAIVSCYGKT    420
KCTASNKNRG IIKTFSNGCD YVSNKGVDTV SVGNTLYCVN KQEGKSLYVK GEPIINFYDP    480
LVFPSDEFDA SISQVNEKIN QSLAFIRGSG GSGSGSGGSE KAAKAEEAAR KMEELFKKHK    540
IVAVLRANSV EEAIEKAVAV FAGGVHLIEI TFTVPDADTV IKALSVLKEK GAIIGAGTVT    600
SVEQCRKAVE SGAEFIVSPH LDEEISQFCK EKGVFYMPGV MTPTELVKAM KLGHTILKLF    660
PGEVVGPQFV KAMKGPFPNV KFVPTGGVNL DNVCEWFKAG VLAVGVGSAL VKGTPDEVRE    720
KAKAFVEKIR GCTE                                                     734

SEQ ID NO: 84          moltype = AA  length = 738
FEATURE                Location/Qualifiers
REGION                 1..738
                       note = DS-Cav1-16GS-HelExt-I53-50A (F12)
VARIANT                1..25
```

```
                        note = optionally absent
source                  1..738
                        mol_type = protein
                        organism = synthetic construct
SEQUENCE: 84
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGSG GSGSGSGGSG SGGEKAAKAE EAARKMEELF   540
KKHKIVAVLR ANSVEEAIEK AVAVFAGGVH LIEITFTVPD ADTVIKALSV LKEKGAIIGA   600
GTVTSVEQCR KAVESGAEFI VSPHLDEEIS QFCKEKGVFY MPGVMTPTEL VKAMKLGHTI   660
LKLFPGEVVG PQFVKAMKGP FPNVKFVPTG GVNLDNVCEW FKAGVLAVGV GSALVKGTPD   720
EVREKAKAFV EKIRGCTE                                                 738

SEQ ID NO: 85           moltype = AA  length = 759
FEATURE                 Location/Qualifiers
REGION                  1..759
                        note = DS-Cav1-foldon-10GS-HelExt-I53-50A (F13)
VARIANT                 1..25
                        note = optionally absent
source                  1..759
                        mol_type = protein
                        organism = synthetic construct
SEQUENCE: 85
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGYI PEAPRDGQAY VRKDGEWVLL STFLGSGGSG   540
SGSGEKAAKA EEAARKMEEL FKKHKIVAVL RANSVEEAIE KAVAVFAGGV HLIEITFTVP   600
DADTVIKALS VLKEKGAIIG AGTVTSVEQC RKAVESGAEF IVSPHLDEEI SQFCKEKGVF   660
YMPGVMTPTE LVKAMKLGHT ILKLFPGEVV GPQFVKAMKG PFPNVKFVPT GGVNLDNVCE   720
WFKAGVLAVG VGSALVKGTP DEVREKAKAF VEKIRGCTE                          759

SEQ ID NO: 86           moltype = AA  length = 769
FEATURE                 Location/Qualifiers
REGION                  1..769
                        note = DS-Cav1-foldon-20GS-HelExt-I53-50A (F15)
VARIANT                 1..25
                        note = optionally absent
source                  1..769
                        mol_type = protein
                        organism = synthetic construct
SEQUENCE: 86
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATNNRARRE LPRFMNYTLN   120
NAKKTNVTLS KKRKRRFLGF LLGVGSAIAS GVAVCKVLHL EGEVNKIKSA LLSTNKAVVS   180
LSNGVSVLTF KVLDLKNYID KQLLPILNKQ SCSISNIETV IEFQQKNNRL LEITREFSVN   240
AGVTTPVSTY MLTNSELLSL INDMPITNDQ KKLMSNNVQI VRQQSYSIMC IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNVDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRGYI PEAPRDGQAY VRKDGEWVLL STFLGSGGSG   540
SGSGSGGSGG SSGSEKAAKA EEAARKMEEL FKKHKIVAVL RANSVEEAIE KAVAVFAGGV   600
HLIEITFTVP DADTVIKALS VLKEKGAIIG AGTVTSVEQC RKAVESGAEF IVSPHLDEEI   660
SQFCKEKGVF YMPGVMTPTE LVKAMKLGHT ILKLFPGEVV GPQFVKAMKG PFPNVKFVPT   720
GGVNLDNVCE WFKAGVLAVG VGSALVKGTP DEVREKAKAF VEKIRGCTE               769

SEQ ID NO: 87           moltype = AA  length = 736
FEATURE                 Location/Qualifiers
REGION                  1..736
                        note = sc9-10 DS-Cav1 A149C Y458C-foldon-I53-50A embodiment
VARIANT                 1..25
                        note = optionally absent
VARIANT                 469..474
                        note = optionally absent
source                  1..736
                        mol_type = protein
                        organism = synthetic construct
SEQUENCE: 87
```

```
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATGSGSAIC SGVAVCKVLH   120
LEGEVNKIKS ALLSTNKAVV SLSNGVSVLT FKVLDLKNYI DKQLLPILNK QSCSISNIET   180
VIEFQQKNNR LLEITREFSV NAGVTTPVST YMLTNSELLS LINDMPITND QKKLMSNNVQ   240
IVRQQSYSIM CIIKEEVLAY VVQLPLYGVI DTPCWKLHTS PLCTTNTKEG SNICLTRTDR   300
GWYCDNAGSV SFFPQAETCK VQSNRVFCDT MNSRTLPSEV NLCNVDIFNP KYDCKIMTSK   360
TDVSSSVITS LGAIVSCYGK TKCTASNKNR GIIKTFSNGC DYVSNKGVDT VSVGNTLYCV   420
NKQEGKSLYV KGEPIINFYD PLVFPSDEFD ASISQVNEKI NQSLAFIRKS DELLGYIPEA   480
PRDGQAYVRK DGEWVLLSTF LGSGSHHHHH HHHGGSGGSG SEKAAKAEEA ARKMEELFKK   540
HKIVAVLRAN SVEEAIEKAV AVFAGGVHLI EITFTVPDAD TVIKALSVLK EKGAIIGAGT   600
VTSVEQCRKA VESGAEFIVS PHLDEEISQF CKEKGVFYMP GVMTPTELVK AMKLGHTILK   660
LFPGEVVGPQ FVKAMKGPFP NVKFVPTGGV NLDNVCEWFK AGVLAVGVGS ALVKGTPDEV   720
REKAKAFVEK IRGCTE                                                   736

SEQ ID NO: 88           moltype = AA  length = 697
FEATURE                 Location/Qualifiers
REGION                  1..697
                        note = sc9-10 DS-Cav1 A149C Y458C - F10 embodiment
VARIANT                 1..25
                        note = optionally absent
VARIANT                 469..474
                        note = optionally absent
source                  1..697
                        mol_type = protein
                        organism = synthetic construct
SEQUENCE: 88
MELLILKANA ITTILTAVTF CFASGQNITE EFYQSTCSAV SKGYLSALRT GWYTSVITIE    60
LSNIKENKCN GTDAKVKLIK QELDKYKNAV TELQLLMQST PATGSGSAIC SGVAVCKVLH   120
LEGEVNKIKS ALLSTNKAVV SLSNGVSVLT FKVLDLKNYI DKQLLPILNK QSCSISNIET   180
VIEFQQKNNR LLEITREFSV NAGVTTPVST YMLTNSELLS LINDMPITND QKKLMSNNVQ   240
IVRQQSYSIM CIIKEEVLAY VVQLPLYGVI DTPCWKLHTS PLCTTNTKEG SNICLTRTDR   300
GWYCDNAGSV SFFPQAETCK VQSNRVFCDT MNSRTLPSEV NLCNVDIFNP KYDCKIMTSK   360
TDVSSSVITS LGAIVSCYGK TKCTASNKNR GIIKTFSNGC DYVSNKGVDT VSVGNTLYCV   420
NKQEGKSLYV KGEPIINFYD PLVFPSDEFD ASISQVNEKI NQSLAFIRKS DELLGSGGSG   480
SGEKAAKAEE AARKMEELFK KHKIVAVLRA NSVEEAIEKA VAVFAGGVHL IEITFTVPDA   540
DTVIKALSVL KEKGAIIGAG TVTSVEQCRK AVESGAEFIV SPHLDEEISQ FCKEKGVFYM   600
PGVMTPTELV KAMKLGHTIL KLFPGEVVGP QFVKAMKGPF PNVKFVPTGG VNLDNVCEWF   660
KAGVLAVGVG SALVKGTPDE VREKAKAFVE KIRGCTE                            697

SEQ ID NO: 89           moltype = AA  length = 736
FEATURE                 Location/Qualifiers
REGION                  1..736
                        note = sc9-10 DS-Cav1 A149C Y458C S46G K465Q S215P E92D
                        -foldon-I53-50A embodiment
VARIANT                 1..25
                        note = optionally absent
VARIANT                 469..474
                        note = optionally absent
source                  1..736
                        mol_type = protein
                        organism = synthetic construct
SEQUENCE: 89
MELLILKANA ITTILTAVTF CFASGQNITE EFYQSTCSAV SKGYLGALRT GWYTSVITIE    60
LSNIKENKCN GTDAKVKLIK QELDKYKNAV TDLQLLMQST PATGSGSAIC SGVAVCKVLH   120
LEGEVNKIKS ALLSTNKAVV SLSNGVSVLT FKVLDLKNYI DKQLLPILNK QSCSIPNIET   180
VIEFQQKNNR LLEITREFSV NAGVTTPVST YMLTNSELLS LINDMPITND QKKLMSNNVQ   240
IVRQQSYSIM CIIKEEVLAY VVQLPLYGVI DTPCWKLHTS PLCTTNTKEG SNICLTRTDR   300
GWYCDNAGSV SFFPQAETCK VQSNRVFCDT MNSRTLPSEV NLCNVDIFNP KYDCKIMTSK   360
TDVSSSVITS LGAIVSCYGK TKCTASNKNR GIIKTFSNGC DYVSNKGVDT VSVGNTLYCV   420
NKQEGQSLYV KGEPIINFYD PLVFPSDEFD ASISQVNEKI NQSLAFIRKS DELLGYIPEA   480
PRDGQAYVRK DGEWVLLSTF LGSGSHHHHH HHHGGSGGSG SEKAAKAEEA ARKMEELFKK   540
HKIVAVLRAN SVEEAIEKAV AVFAGGVHLI EITFTVPDAD TVIKALSVLK EKGAIIGAGT   600
VTSVEQCRKA VESGAEFIVS PHLDEEISQF CKEKGVFYMP GVMTPTELVK AMKLGHTILK   660
LFPGEVVGPQ FVKAMKGPFP NVKFVPTGGV NLDNVCEWFK AGVLAVGVGS ALVKGTPDEV   720
REKAKAFVEK IRGCTE                                                   736

SEQ ID NO: 90           moltype = AA  length = 697
FEATURE                 Location/Qualifiers
REGION                  1..697
                        note = sc9-10 DS-Cav1 A149C Y458C S46G K465Q S215P E92D -
                        F10 embodiment
VARIANT                 1..25
                        note = optionally absent
VARIANT                 469..474
                        note = optionally absent
source                  1..697
                        mol_type = protein
                        organism = synthetic construct
SEQUENCE: 90
```

```
MELLILKANA ITTILTAVTF CFASGQNITE EFYQSTCSAV SKGYLGALRT GWYTSVITIE      60
LSNIKENKCN GTDAKVKLIK QELDKYKNAV TDLQLLMQST PATGSGSAIC SGVAVCKVLH     120
LEGEVNKIKS ALLSTNKAVV SLSNGVSVLT FKVLDLKNYI DKQLLPILNK QSCSIPNIET     180
VIEFQQKNNR LLEITREFSV NAGVTTPVST YMLTNSELLS LINDMPITND QKKLMSNNVQ     240
IVRQQSYSIM CIIKEEVLAY VVQLPLYGVI DTPCWKLHTS PLCTTNTKEG SNICLTRTDR     300
GWYCDNAGSV SFFPQAETCK VQSNRVFCDT MNSRTLPSEV NLCNVDIFNP KYDCKIMTSK     360
TDVSSSVITS LGAIVSCYGK TKCTASNKNR GIIKTFSNGC DYVSNKGVDT VSVGNTLYCV     420
NKQEGQSLYV KGEPIINFYD PLVFPSDEFD ASISQVNEKI NQSLAFIRKS DELLGSGGSG     480
SGEKAAKAEE AARKMEELFK KHKIVAVLRA NSVEEAIEKA VAVFAGGVHL IEITFTVPDA     540
DTVIKALSVL KEKGAIIGAG TVTSVEQCRK AVESGAEFIV SPHLDEEISQ FCKEKGVFYM     600
PGVMTPTELV KAMKLGHTIL KLFPGEVVGP QFVKAMKGPF PNVKFVPTGG VNLDNVCEWF     660
KAGVLAVGVG SALVKGTPDE VREKAKAFVE KIRGCTE                              697

SEQ ID NO: 91              moltype = AA  length = 753
FEATURE                    Location/Qualifiers
REGION                     1..753
                           note = SC-DM (N67I, S215P) - foldon-I53-50A embodiment
VARIANT                    1..25
                           note = optionally absent
VARIANT                    486..491
                           note = optionally absent
source                     1..753
                           mol_type = protein
                           organism = synthetic construct
SEQUENCE: 91
MELLILKANA ITTILTAVTF CFASGQNITE EFYQSTCSAV SKGYLSALRT GWYTSVITIE      60
LSNIKKIKCN GTDAKIKLIK QELDKYKNAV TELQLLMQST PATNNQARGS GSGRSLGFLL     120
GVGSAIASGV AVSKVLHLEG EVNKIKSALL STNKAVVSLS NGVSVLTSKV LDLKNYIDKQ     180
LLPIVNKQSC SIPNIETVIE FQQKNNRLLE ITREFSVNAG VTTPVSTYML TNSELLSLIN     240
DMPITNDQKK LMSNNVQIVR QQSYSIMSII KEEVLAYVVQ LPLYGVIDTP CWKLHTSPLC     300
TTNTKEGSNI CLTRTDRGWY CDNAGSVSFF PQAETCKVQS NRVFCDTMNS LTLPSEVNLC     360
NVDIFNPKYD CKIMTSKTDV SSSVITSLGA IVSCYGKTKC TASNKNRGII KTFSNGCDYV     420
SNKGVDTVSV GNTLYYVNKQ EGKSLYVKGE PIINFYDPLV FPSDEFDASI SQVNEKINQS     480
LAFIRKSDEL GYIPEAPRD GQAYVRKDGE WVLLSTFLGS GSHHHHHHHH GGSGGSGSEK     540
AAKAEEAARK MEELFKKHKI VAVLRANSVE EAIEKAVAVF AGGVHLIEIT FTVPDADTVI     600
KALSVLKEKG AIIGAGTVTS VEQCRKAVES GAEFIVSPHL DEEISQFCKE KGVFYMPGVM     660
TPTELVKAMK LGHTILKLFP GEVVGPQFVK AMKGPFPNVK FVPTGGVNLD NVCEWFKAGV     720
LAVGVGSALV KGTPDEVREK AKAFVEKIRG CTE                                  753

SEQ ID NO: 92              moltype = AA  length = 714
FEATURE                    Location/Qualifiers
REGION                     1..714
                           note = SC-DM (N67I, S215P) - F10 embodiment
VARIANT                    1..25
                           note = optionally absent
VARIANT                    486..491
                           note = optionally absent
source                     1..714
                           mol_type = protein
                           organism = synthetic construct
SEQUENCE: 92
MELLILKANA ITTILTAVTF CFASGQNITE EFYQSTCSAV SKGYLSALRT GWYTSVITIE      60
LSNIKKIKCN GTDAKIKLIK QELDKYKNAV TELQLLMQST PATNNQARGS GSGRSLGFLL     120
GVGSAIASGV AVSKVLHLEG EVNKIKSALL STNKAVVSLS NGVSVLTSKV LDLKNYIDKQ     180
LLPIVNKQSC SIPNIETVIE FQQKNNRLLE ITREFSVNAG VTTPVSTYML TNSELLSLIN     240
DMPITNDQKK LMSNNVQIVR QQSYSIMSII KEEVLAYVVQ LPLYGVIDTP CWKLHTSPLC     300
TTNTKEGSNI CLTRTDRGWY CDNAGSVSFF PQAETCKVQS NRVFCDTMNS LTLPSEVNLC     360
NVDIFNPKYD CKIMTSKTDV SSSVITSLGA IVSCYGKTKC TASNKNRGII KTFSNGCDYV     420
SNKGVDTVSV GNTLYYVNKQ EGKSLYVKGE PIINFYDPLV FPSDEFDASI SQVNEKINQS     480
LAFIRKSDEL LGSGGSGSGE KAAKAEEAAR KMEELFKKHK IVAVLRANSV EEAIEKAVAV     540
FAGGVHLIEI TFTVPDADTV IKALSVLKEK GAIIGAGTVT SVEQCRKAVE SGAEFIVSPH     600
LDEEISQFCK EKGVFYMPGV MTPTELVKAM KLGHTILKLF PGEVVGPQFV KAMKGPFPNV     660
KFVPTGGVNL DNVCEWFKAG VLAVGVGSAL VKGTPDEVRE KAKAFVEKIR GCTE           714

SEQ ID NO: 93              moltype = AA  length = 753
FEATURE                    Location/Qualifiers
REGION                     1..753
                           note = SC-TM (N67I, S215P, and E487Q) - foldon-I53-50A
                            embodiment
VARIANT                    1..25
                           note = optionally absent
VARIANT                    486..491
                           note = optionally absent
source                     1..753
                           mol_type = protein
                           organism = synthetic construct
SEQUENCE: 93
MELLILKANA ITTILTAVTF CFASGQNITE EFYQSTCSAV SKGYLSALRT GWYTSVITIE      60
LSNIKKIKCN GTDAKIKLIK QELDKYKNAV TELQLLMQST PATNNQARGS GSGRSLGFLL     120
```

```
GVGSAIASGV AVSKVLHLEG EVNKIKSALL STNKAVVSLS NGVSVLTSKV LDLKNYIDKQ    180
LLPIVNKQSC SIPNIETVIE FQQKNNRLLE ITREFSVNAG VTTPVSTYML TNSELLSLIN    240
DMPITNDQKK LMSNNVQIVR QQSYSIMSII KEEVLAYVVQ LPLYGVIDTP CWKLHTSPLC    300
TTNTKEGSNI CLTRTDRGWY CDNAGSVSFF PQAETCKVQS NRVFCDTMNS LTLPSEVNLC    360
NVDIFNPKYD CKIMTSKTDV SSSVITSLGA IVSCYGKTKC TASNKNRGII KTFSNGCDYV    420
SNKGVDTVSV GNTLYYVNKQ EGKSLYVKGE PIINFYDPLV FPSDQFDASI SQVNEKINQS    480
LAFIRKSDEL LGYIPEAPRD GQAYVRKDGE WVLLSTFLGS GSHHHHHHHH GGSGGSGSEK    540
AAKAEEAARK MEELFKKHKI VAVLRANSVE EAIEKAVAVF AGGVHLIEIT FTVPDADTVI    600
KALSVLKEKG AIIGAGTVTS VEQCRKAVES GAEFIVSPHL DEEISQFCKE KGVFYMPGVM    660
TPTELVKAMK LGHTILKLFP GEVVGPQFVK AMKGPFPNVK FVPTGGVNLD NVCEWFKAGV    720
LAVGVGSALV KGTPDEVREK AKAFVEKIRG CTE                                753

SEQ ID NO: 94           moltype = AA  length = 714
FEATURE                 Location/Qualifiers
REGION                  1..714
                        note = SC-TM (N67I, S215P, and E487Q)-I53-50A - F10
                        embodiment
VARIANT                 1..25
                        note = optionally absent
VARIANT                 486..491
                        note = optionally absent
source                  1..714
                        mol_type = protein
                        organism = synthetic construct
SEQUENCE: 94
MELLILKANA ITTILTAVTF CFASGQNITE EFYQSTCSAV SKGYLSALRT GWYTSVITIE     60
LSNIKKIKCN GTDAKIKLIK QELDKYKNAV TELQLLMQST PATNNQARGS GSGRSLGFLL    120
GVGSAIASGV AVSKVLHLEG EVNKIKSALL STNKAVVSLS NGVSVLTSKV LDLKNYIDKQ    180
LLPIVNKQSC SIPNIETVIE FQQKNNRLLE ITREFSVNAG VTTPVSTYML TNSELLSLIN    240
DMPITNDQKK LMSNNVQIVR QQSYSIMSII KEEVLAYVVQ LPLYGVIDTP CWKLHTSPLC    300
TTNTKEGSNI CLTRTDRGWY CDNAGSVSFF PQAETCKVQS NRVFCDTMNS LTLPSEVNLC    360
NVDIFNPKYD CKIMTSKTDV SSSVITSLGA IVSCYGKTKC TASNKNRGII KTFSNGCDYV    420
SNKGVDTVSV GNTLYYVNKQ EGKSLYVKGE PIINFYDPLV FPSDQFDASI SQVNEKINQS    480
LAFIRKSDEL LGSGGSGSGE KAAKAEEEAAR KMEELFKKHK IVAVLRANSV EEAIEKAVAV   540
FAGGVHLIEI TFTVPDADTV IKALSVLKEK GAIIGAGTVT SVEQCRKAVE SGAEFIVSPH   600
LDEEISQFCK EKGVFYMPGV MTPTELVKAM KLGHTILKLF PGEVVGPQFV KAMKGPFPNV   660
KFVPTGGVNL DNVCEWFKAG VLAVGVGSAL VKGTPDEVRE KAKAFVEKIR GCTE         714

SEQ ID NO: 95           moltype = AA  length = 752
FEATURE                 Location/Qualifiers
REGION                  1..752
                        note = HMPV-F with A113C, A339C, T160F, I177L -
                        foldon-I53-50A embodiment
VARIANT                 1..18
                        note = optionally absent
source                  1..752
                        mol_type = protein
                        organism = synthetic construct
SEQUENCE: 95
MSWKVVIIFS LLITPQHGLK ESYLEESCST ITEGYLSVLR TGWYTNVFTL EVGDVENLTC     60
SDGPSLIKTE LDLTKSALRE LKTVSADQLA REEQIENPRQ SRFVLGAIAL GVCTAAAVTA    120
GVAIAKTIRL ESEVTAIKNA LKTTNEAVST LGNGVRVLAF AVRELKDFVS KNLTRALNKN    180
KCDIDDLKMA VSFSQFNRRF LNVVRQFSDN AGITPAISLD LMTDAELARA VSNMPTSAGQ    240
IKLMLENRAM VRRKGFGILI GVYGSSVIYM VQLPIFGVID TPCWIVKAAP SCSGKKGNYA    300
CLLREDQGWY CQNAGSTVYY PNEKDCETRG DHVFCDTACG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPIK FPEDQFNVAL DQVFENIENS QALVDQSNRI    480
LSSAEKGNTG GYIPEAPRDG QAYVRKDGEW VLLSTFLGSG SHHHHHHHG GSGGSGSEKA    540
AKAEEAARKM EELFKKHKIV AVLRANSVEE AIEKAVAVFA GGVHLIEITF TVPDADTVIK    600
ALSVLKEKGA IIGAGTVTSV EQCRKAVESG AEFIVSPHLD EEISQFCKEK GVFYMPGVMT    660
PTELVKAMKL GHTILKLFPG EVVGPQFVKA MKGPFPNVKF VPTGGVNLDN VCEWFKAGVL    720
AVGVGSALVK GTPDEVREKA KAFVEKIRGC TE                                 752

SEQ ID NO: 96           moltype = AA  length = 713
FEATURE                 Location/Qualifiers
REGION                  1..713
                        note = HMPV-F with A113C, A339C, T160F, I177L-I53-50A F10
                        embodiment
VARIANT                 1..18
                        note = optionally absent
source                  1..713
                        mol_type = protein
                        organism = synthetic construct
SEQUENCE: 96
MSWKVVIIFS LLITPQHGLK ESYLEESCST ITEGYLSVLR TGWYTNVFTL EVGDVENLTC     60
SDGPSLIKTE LDLTKSALRE LKTVSADQLA REEQIENPRQ SRFVLGAIAL GVCTAAAVTA    120
GVAIAKTIRL ESEVTAIKNA LKTTNEAVST LGNGVRVLAF AVRELKDFVS KNLTRALNKN    180
KCDIDDLKMA VSFSQFNRRF LNVVRQFSDN AGITPAISLD LMTDAELARA VSNMPTSAGQ    240
IKLMLENRAM VRRKGFGILI GVYGSSVIYM VQLPIFGVID TPCWIVKAAP SCSGKKGNYA    300
```

```
CLLREDQGWY CQNAGSTVYY PNEKDCETRG DHVFCDTACG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPIK FPEDQFNVAL DQVFENIENS QALVDQSNRI    480
LSSAEKGNTG GSGGSGSGEK AAKAEEEAARK MEELFKKHKI VAVLRANSVE EAIEKAVAVF   540
AGGVHLIEIT FTVPDADTVI KALSVLKEKG AIIGAGTVTS VEQCRKAVES GAEFIVSPHL   600
DEEISQFCKE KGVFYMPGVM TPTELVKAMK LGHTILKLFP GEVVGPQFVK AMKGPFPNVK   660
FVPTGGVNLD NVCEWFKAGV LAVGVGSALV KGTPDEVREK AKAFVEKIRG CTE          713

SEQ ID NO: 97           moltype = AA  length = 752
FEATURE                 Location/Qualifiers
REGION                  1..752
                        note = HMPV-F with A113C, A120C, A339C, T -continued

```
VGVGSALVKG TPDEVREKAK AFVEKIRGCT E                              751

SEQ ID NO: 100          moltype = AA  length = 712
FEATURE                 Location/Qualifiers
REGION                  1..712
                        note = HMPV-F 115-BV (A185P)-I53-50A - F10 embodiment
VARIANT                 1..18
                        note = optionally absent
source                  1..712
                        mol_type = protein
                        organism = synthetic construct
SEQUENCE: 100
MSWKVVIIFS LLITPQHGLK ESYLEESCST ITEGYLSVLR TGWYTNVFTL EVGDVENLTC  60
ADGPSLIKTE LDLTKSALRE LRTVSADQLA REEQIENPRR RRFVLGAIAL GVATAAAVTA  120
GVAIAKTIRL ESEVTAIKNA LKKTNEAVST LGNGVRVLAT AVRELKDFVS KNLTRAINKN  180
KCDIPDLKMA VSFSQFNRRF LNVVRQFSDN AGITPAISLD LMTDAELARA VSNMPTSAGQ  240
IKLMLENRAM VRRKGFGILI GVYGSSVIYM VQLPIFGVID TPCWIVKAAP SCSEKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
LSSAEKGNTG SGGSGSGEKA AKAEEAARKM EELFKKHKIV AVLRANSVEE AIEKAVAVFA  540
GGVHLIEITF TVPDADTVIK ALSVLKEKGA IIGAGTVTSV EQCRKAVESG AEFIVSPHLD  600
EEISQFCKEK GVFYMPGVMT PTELVKAMKL GHTILKLFPG EVVGPQFVKA MKGPFPNVKF  660
VPTGGVNLDN VCEWFKAGVL AVGVGSALVK GTPDEVREKA KAFVEKIRGC TE        712

SEQ ID NO: 101          moltype = AA  length = 490
FEATURE                 Location/Qualifiers
REGION                  1..490
                        note = HMPV F AAK62968.2 fusion protein [Human
                         metapneumovirus]
VARIANT                 1..18
                        note = optionally absent
source                  1..490
                        mol_type = protein
                        organism = synthetic construct
SEQUENCE: 101
MSWKVVIIFS LLITPQHGLK ESYLEESCST ITEGYLSVLR TGWYTNVFTL EVGDVENLTC  60
ADGPSLIKTE LDLTKSALRE LRTVSADQLA REEQIENPRQ SRFVLGAIAL GVATAAAVTA  120
GVAIAKTIRL ESEVTAIKNA LKKTNEAVST LGNGVRVLAT AVRELKDFVS KNLTRAINKN  180
KCDIADLKMA VSFSQFNRRF LNVVRQFSDN AGITPAISLD LMTDAELARA VSNMPTSAGQ  240
IKLMLENRAM VRRKGFGFLI GVYGSSVIYM VQLPIFGVID TPCWIVKAAP SCSGKKGNYA  300
CLLREDQGWY CQNAGSTVYY PNEKDCETRG DHVFCDTAAG INVAEQSKEC NINISTTNYP  360
CKVSTGRHPI SMVALSPLGA LVACYKGVSC SIGSNRVGII KQLNKGCSYI TNQDADTVTI  420
DNTVYQLSKV EGEQHVIKGR PVSSSFDPVK FPEDQFNVAL DQVFESIENS QALVDQSNRI  480
LSSAEKGNTG                                                      490
```

SELF-ASSEMBLING PROTEIN NANOSTRUCTURES DISPLAYING PARAMYXOVIRUS AND/OR PNEUMOVIRUS F PROTEINS AND THEIR USE

CROSS REFERENCE

This application is a continuation of U.S. patent application Ser. No. 17/523,174, filed Nov. 10, 2021, which is a divisional of U.S. patent application Ser. No. 16/500,331, filed Oct. 2, 2019 (now U.S. Pat. No. 11,192,926), which is a U.S. national phase of International Application No. PCT/US2018/025880, filed on Apr. 3, 2018, which claims priority to U.S. Provisional Application No. 62/481,331, filed Apr. 4, 2017, all of which are incorporated by reference herein in their entirety

REFERENCE TO SEQUENCE LISTING SUBMITTED ELECTRONICALLY

The instant application contains a Sequence Listing which has been submitted electronically and is hereby incorporated by reference in its entirety. The Sequence Listing is contained in the file created on Jun. 27, 2023, having the file name "17-341-PCT_amended.xml" and is 222,365 bytes in size.

BACKGROUND

Molecular self- and co-assembly of proteins into highly ordered, symmetric supramolecular complexes is an elegant and powerful means of patterning matter at the atomic scale. Recent years have seen advances in the development of self-assembling biomaterials, particularly those composed of nucleic acids. DNA has been used to create, for example, nanoscale shapes and patterns, molecular containers, and three-dimensional macroscopic crystals. Methods for designing self-assembling proteins have progressed more slowly, yet the functional and physical properties of proteins make them attractive as building blocks for the development of advanced functional materials.

SUMMARY OF THE INVENTION

In one aspect, nanostructures are provided comprising:
(a) a plurality of first assemblies, each first assembly comprising a plurality of identical first polypeptides;
(b) a plurality of second assemblies, each second assembly comprising a plurality of identical second polypeptides, wherein the second polypeptide differs from the first polypeptide;
wherein the plurality of first assemblies non-covalently interact with the plurality of second assemblies to form a nanostructure; and
wherein the nanostructure displays multiple copies of one or more paramyxovirus and/or pneumovirus F proteins, or antigenic fragments thereof, on an exterior of the nanostructure.

In one embodiment, (a) the first polypeptides comprise a polypeptide having at least 70%, 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS:1-51; and
(b) the second polypeptides comprise a polypeptide having at least 70%, 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS:1-51.

In another embodiment, the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to the amino acid sequence of a polypeptide selected from the group consisting of SEQ ID NOS: 53, 61-68, and 101.

In various embodiments:
(a) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-31A (SEQ ID NO:51) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-09B/T33-31B (SEQ ID NO:44);
(b) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-15B (SEQ ID NO:46) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of T33-15A (SEQ ID NO:45);
(c) the first polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50A (SEQ ID NO:7), I53-50A.1 (SEQ ID NO:29), I53-50A.1NegT2 (SEQ ID NO:30), and I53-50A.1PosT1 (SEQ ID NO:31), and the second polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50B (SEQ ID NO:8), I53-50B.1 (SEQ ID NO:32), I53-50B.1NegT2 (SEQ ID NO:33), and I53-50B.4PosT1 (SEQ ID NO:34); or
(d) the first polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I32-28A (SEQ ID NO:21) and the second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I32-28B (SEQ ID NO:22).

In one embodiment, the one or more paramyxovirus and/or pneumovirus F proteins, or antigenic fragments thereof, are expressed as a fusion protein with the first polypeptides. In one such embodiment, the plurality of first assemblies each comprise identical first polypeptides; in another such embodiment, the plurality of first assemblies in total comprise two or more paramyxovirus and/or pneumovirus F proteins, or antigenic fragments thereof. In another embodiment, only a subset of the first polypeptides comprise a fusion protein with an F protein or antigenic fragment thereof. In a further embodiment, each first assembly comprises a homotrimer of the first polypeptide.

In another embodiment, the fusion protein comprises an amino acid linker positioned between the first polypeptide and the paramyxovirus and/or pneumovirus F proteins, or antigenic fragment thereof. In one such embodiment, the fusion protein comprises an amino acid linker positioned between the first polypeptide and the paramyxovirus F proteins, or antigenic fragment thereof.

In one embodiment the amino acid linker sequence comprises one or more trimerization domain; in another embodiment the amino acid linker sequence comprises a Gly-Ser linker.

In various embodiments, the first polypeptides comprise or consist of first polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of DS-Cav1-foldon-T33-31A (SEQ ID NO:69), DS-Cav1-T33-31A (SEQ ID NO:70), DS-Cav1-foldon-T33-15B (SEQ ID NO:71), DS-Cav1-T33-15B (SEQ ID NO:72), DS-Cav1-foldon-I53-50A (SEQ ID NO:73), DS-Cav1-I53-50A (SEQ ID NO:74), and DS-Cav1-I32-28A (SEQ ID NO:75). In other embodiments, (a) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-T33-31A (SEQ ID NO:69) or DS-Cav1-T33-31A (SEQ ID NO:70), each second polypeptide has at least 75%, 80%, 85%, 90%, 91%, 92%, 93%, 94%, 95%, 96%, 97%, 98%, 99%, or 100% identity along its full length to the amino acid sequence of T33-31B (SEQ ID NO:44);

(b) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-T33-15B (SEQ ID NO:71) or DS-Cav1-T33-15B (SEQ ID NO:72), each second polypeptide has at least 75%, 80%, 85%, 90%, 91%, 92%, 93%, 94%, 95%, 96%, 97%, 98%, 99%, or 100% identity along its full length to the amino acid sequence of T33-15A (SEQ ID NO:45);

(c) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-foldon-I53-50A (SEQ ID NO:73) or DS-Cav1-I53-50A (SEQ ID NO:74), each second polypeptide has at least 75%, 80%, 85%, 90%, 91%, 92%, 93%, 94%, 95%, 96%, 97%, 98%, 99%, or 100% identity along its full length to the amino acid sequence of a polypeptide selected from the group consisting of I53-50B (SEQ ID NO:8), I53-50B.1 (SEQ ID NO:32), I53-50B.1NegT2 (SEQ ID NO:33), or I53-50B.4PosT1 (SEQ ID NO:34); or (d) when each first polypeptide has at least 75%, 80%, 85%, 90%, 91%, 92%, 93%, 94%, 95%, 96%, 97%, 98%, 99%, or 100% identity along its full length to the amino acid sequence of DS-Cav1-I32-28A (SEQ ID NO:75), each second polypeptide has at least 75%, 80%, 85%, 90%, 91%, 92%, 93%, 94%, 95%, 96%, 97%, 98%, 99%, or 100% identity along its full length to the amino acid sequence of I32-28B.

In one embodiment, the one or more paramyxovirus and/or pneumovirus F proteins, or antigenic fragments thereof comprises a polypeptide having at least 75%, 80%, 85%, 90%, 91%, 92%, 93%, 94%, 95%, 96%, 97%, 98%, 99%, or 100% identity along its full length to the amino acid sequence of DS-Cav1 (SEQ ID NO:53). In one such embodiment, each first polypeptide comprises a fusion polypeptide of a polypeptide having at least 75%, 80%, 85%, 90%, 91%, 92%, 93%, 94%, 95%, 96%, 97%, 98%, 99%, or 100% identity along its full length to the amino acid sequence of DS-Cav1 linked via an amino acid linker to a polypeptide having at least 75%, 80%, 85%, 90%, 91%, 92%, 93%, 94%, 95%, 96%, 97%, 98%, 99%, or 100% identity along its full length to the amino acid sequence of SEQ ID NO:7 (I53-50A). In another embodiment, the amino acid linker comprises a Gly-Ser linker. In a further embodiment, each fusion protein comprises a polypeptide having at least 75%, 80%, 85%, 90%, 91%, 92%, 93%, 94%, 95%, 96%, 97%, 98%, 99%, or 100% identity along its full length to the amino acid sequence selected from the group consisting of SEQ ID NOS:69-100. In a specific embodiment, each fusion protein comprises a polypeptide having at least 75%, 80%, 85%, 90%, 91%, 92%, 93%, 94%, 95%, 96%, 97%, 98%, 99%, or 100% identity along its full length to the amino acid sequence of SEQ ID NO:76 (F10). In other embodiments, each second polypeptide comprises a polypeptide having at least 75%, 80%, 85%, 90%, 91%, 92%, 93%, 94%, 95%, 96%, 97%, 98%, 99%, or 100% identity along its full length to the amino acid sequence selected from the group consisting of I53-50B (SEQ ID NO:8), I53-50B.1 (SEQ ID NO:32), I53-50B.1NegT2 (SEQ ID NO:33), or I53-15 50B.4PosT1 (SEQ ID NO:34). In a specific embodiment, each second polypeptide comprises a polypeptide having at least 75%, 80%, 85%, 90%, 91%, 92%, 93%, 94%, 95%, 96%, 97%, 98%, 99%, or 100% identity along its full length to the amino acid sequence of I53-50B.4PosT1 (SEQ ID NO:34).

In other aspects, recombinant expression nucleic acids expressing the first polypeptide fusions, recombinant expression vectors comprising the recombinant nucleic acids linked to a promoter, and recombinant host cells comprising the recombinant expression vectors are provided.

Also provided are immunogenic compositions comprising the nanostructure of any embodiment or combination of embodiments disclosed herein, and a pharmaceutically acceptable carrier. In one embodiment, the immunogenic compositions may further comprise an adjuvant.

In other aspects, methods for generating an immune response to RSV F protein in a subject, or for treating or limiting a RSV infection in a subject are provided, comprising administering to the subject in need thereof an effective amount of the nanostructure or immunogenic composition of embodiment or combination of embodiments disclosed herein to generate the immune response or to treat or prevent RSV infection in the subject.

Also provided are processes assembling the nanostructures of any embodiment or combination of embodiments disclosed herein, comprising mixing two or more nanostructures components in aqueous conditions to drive spontaneous assembly of the desired nanostructures.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
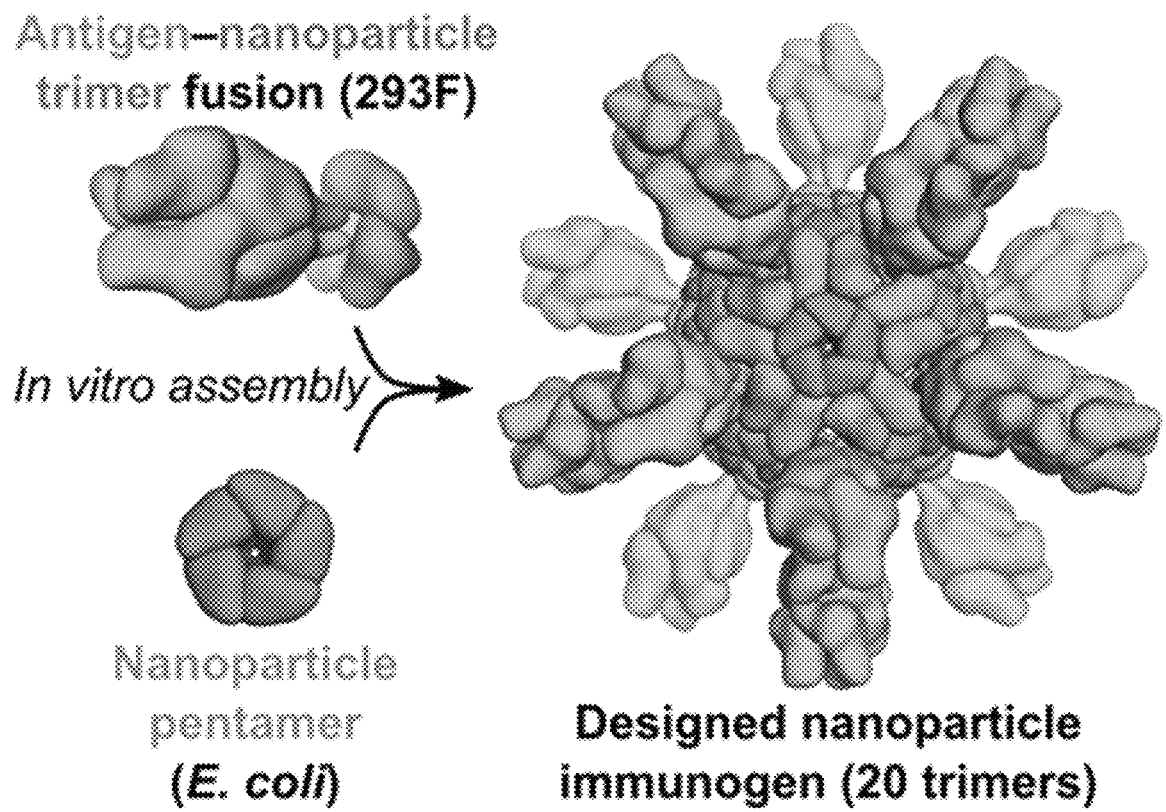
FIG. 1 shows a schematic diagram of the production of antigen-bearing nanostructures by in vitro assembly. The two components or building blocks of a given nanostructure can be expressed and purified individually, which allows assembly of the nanostructure to be initiated by mixing the purified components in vitro, a process referred to as in vitro assembly. In some embodiments, the two components of the nanostructure may be expressed in different expression hosts (e.g., human HEK293F cells or bacterial *E. coli* cells). The figure schematically depicts assembly of a 120-subunit nanostructure bearing 20 trimeric antigens (60 antigen subunits) via in vitro assembly of an antigen-nanostructure trimer fusion protein produced in HEK293F cells and a nanostructure pentamer protein produced in *E. coli*.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, "about" means +/−5% of the recited parameter.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the disclosure provides nanostructures, comprising:
(a) a plurality of first assemblies, each first assembly comprising a plurality of identical first polypeptides;
(b) a plurality of second assemblies, each second assembly comprising a plurality of identical second polypeptides, wherein the second polypeptide differs from the first polypeptide;
wherein the plurality of first assemblies non-covalently interact with the plurality of second assemblies to form a nanostructure; and
wherein the nanostructure displays multiple copies of one or more paramyxovirus and/or pneumovirus F proteins, or antigenic fragments thereof, on an exterior of the nanostructure.

Self-assembling polypeptide nanostructures are disclosed herein that multivalently display paramyxovirus and/or pneumovirus F proteins on the nanostructure exteriors. Multiple copies of pairs of first and second polypeptides are able to self-assemble to form nanostructures, such as icosahedral nanostructures. The nanostructures include symmetrically repeated, non-natural, non-covalent polypeptide-polypeptide interfaces that orient a first assembly and a second assembly into a nanostructure, such as one with an icosahedral symmetry.

The nanostructures of the invention are synthetic, in that they are not naturally occurring. The first polypeptides and the second polypeptides are non-naturally occurring proteins that can be produced by any suitable means, including recombinant production or chemical synthesis. Each member of the plurality of first polypeptides is identical to each other (though when the first polypeptide is present as a fusion polypeptide with one or more paramyxovirus and/or pneumovirus F proteins, or antigenic fragments thereof, the F protein or antigenic fragment thereof may differ from one first polypeptide to another), and each member of the plurality of second polypeptides is identical to each other. The first proteins and the second proteins are different. There are no specific primary amino acid sequence requirements for the first and second polypeptides. US published patent application 20160122392 and published PCT application WO2014/124301 describe methods for designing synthetic nanostructures, where the nanostructures are not dependent on specific primary amino acid sequences of the first and second polypeptides.

A plurality (2, 3, 4, 5, 6, or more) of first polypeptides self-assemble to form a first assembly, and a plurality (2, 3, 4, 5, 6, or more) of second polypeptides self-assemble to form a second assembly. A plurality of these first and second assemblies then self-assemble non-covalently via the designed interfaces to produce the nanostructures.

The number of first polypeptides in the first assemblies may be the same or different than the number of second polypeptides in the second assemblies. In one exemplary embodiment, the first assembly comprises trimers of the first polypeptides, and the second assembly comprises dimers of the second polypeptides. In a further exemplary embodiment, the first assembly comprises trimers of the first polypeptides, and the second assembly comprises trimers of the second polypeptides. In a further exemplary embodiment, the first assembly comprises trimers of the first polypeptides, and the second assembly comprises pentamers of the second polypeptides.

The first and second polypeptides may be of any suitable length for a given purpose of the resulting nanostructure. In one embodiment, the first polypeptides and the second polypeptides are typically between 30-250 amino acids in length; the length of the first polypeptides and the second polypeptides may be the same or different. In various further embodiments, the first polypeptides and the second polypeptides are between 30-225, 30-200, 30-175, 50-250, 50-225, 50-200, 50-175, 75-250, 75-225, 75-200, 75-175, 100-250, 100-225, 100-200, 100-175, 125-250, 125-225, 125-200, 125-175, 150-250, 150-225, 150-200, and 150-175 amino acids in length.

The isolated polypeptides of SEQ ID NOS:1-51 were designed for their ability to self-assemble in pairs to form nanostructures, such as icosahedral nanostructures. The design involved design of suitable interface residues for each member of the polypeptide pair that can be assembled to form the nanostructure. The nanostructures so formed include symmetrically repeated, non-natural, non-covalent polypeptide-polypeptide interfaces that orient a first assembly and a second assembly into a nanostructure, such as one with an icosahedral symmetry. Thus, in one embodiment the first and second polypeptides are selected from the group SEQ ID NOS:1-51. In each case, the N-terminal methionine residue is optional.

TABLE 1

| Name | Amino Acid Sequence | Identified interface residues |
|---|---|---|
| I53-34A SEQ ID NO: 1 | (M)EGMDPLAVLAESRLLPLLTVRGGEDLAGLATVLELMGV GALEITLRTEKGLEALKALRKSGLLLGAGTVRSPKEAEAAL EAGAAFLVSPGLLEEVAALAQARGVPYLPGVLTPTEVERAL | I53-34A: 28, 32, 36, 37, 186, 188, 191, 192, 195 |

TABLE 1-continued

| Name | Amino Acid Sequence | Identified interface residues |
|---|---|---|
| | ALGLSALKFFPAEPFQGVRVLRAYAEVFPEVRFLPTGGIKE EHLPHYAALPNLLAVGGSWLLQGDLAAVMKKVKAAKALLSP QAPG | |
| I53-34B SEQ ID NO: 2 | (M)TKKVGIVDTTFARVDMAEAAIRTLKALSPNIKIIRKTV PGIKDLPVACKKLLEEEGCDIVMALGMPGKAEKDKVCAHEA SLGLMLAQLMTNKHIIEVFVHEDEAKDDDELDILALVRAIE HAANVYYLLFKPEYLTRMAGKGLRQGREDAGPARE | I53-34B: 19, 20, 23, 24, 27, 109, 113, 116, 117, 120, 124, 148 |
| I53-40A SEQ ID NO: 3 | (M)TKKVGIVDTTFARVDMASAAILTLKMESPNIKIIRKTV PGIKDLPVACKKLLEEEGCDIVMALGMPGKAEKDKVCAHEA SLGLMLAQLMTNKHIIEVFVHEDEAKDDAELKILAARRAIE HALNVYYLLFKPEYLTRMAGKGLRQGFEDAGPARE | I53-40A: 20, 23, 24, 27, 28, 109, 112, 113, 116, 120, 124 |
| I53-40B SEQ ID NO: 4 | (M)STINNQLKALKVIPVIAIDNAEDIIPLGKVLAENGLPA AEITFRSSAAVKAIMLLRSAQPEMLIGAGTILNGVQALAAK EAGATFVVSPGFNPNTVRACQIIGIDIVPGVNNPSTVEAAL EMGLITLKFFPAEASGGISMVKSLVGPYGDIRLMPTGGITP SNIDNYLAIPQVLACGGTWMVDKKLVTNGEWDEIARLTREI VEQVNP | I53-40B: 47, 51, 54, 58, 74, 102 |
| I53-47A SEQ ID NO: 5 | (M)PIFTLNTNIKATDVPSDFLSLTSRLVGLILSKPGSYVA VHINTDQQLSFGGSTNPAAFGTLMSIGGIEPSKNRDHSAVL FDHLNAMLGIPKNRMYIHFVNLNGDDVGWNGTTF | I53-47A: 22, 25, 29, 72, 79, 86, 87 |
| I53-47B SEQ ID NO: 6 | (M)NQHSHKDYETVRIAVVRARWHADIVDACVEAFEIAMAA IGGDRFAVDVFDVPGAYEIPLHARTLAETGRYGAVLGTAFV VNGGIYRHEFVASAVIDGMMNVQLSTGVPVLSAVLTPHRYR DSAEHHRFFAAHFAVKGVEAARACIEILAAREKIAA | I53-47B: 28, 31, 35, 36, 39, 131, 132, 135, 139, 146 |
| I53-50A SEQ ID NO: 7 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHTILKLFPGEVVGPQFVKAMKGPFPNVKFVPTGGVNLD NVCEWFKAGVLAVGVGSALVKGTPDEVREKAKAFVEKIRGC TE | I53-50A: 25, 29, 33, 54, 57 |
| I53-50B SEQ ID NO: 8 | (M)NQHSHKDYETVRIAVVRARWHAEIVDACVSAFEAAMAD IGGDRFAVDVFDVPGAYEIPLHARTLAETGRYGAVLGTAFV VNGGIYRHEFVASAVIDGMMNVQLSTGVPVLSAVLTPHRYR DSDAHILLFLALFAVKGMEAARACVEILAAREKIAA | I53-50B: 24, 28, 36, 124, 125, 127, 128, 129, 131, 132, 133, 135, 139 |
| I53-51A SEQ ID NO: 9 | (M)FTKSGDDGNTNVINKRVGKDSPLVNFLGDLDELNSFIG FAISKIPWEDMKKDLERVQVELFEIGEDLSTQSSKKKIDES YVLWLLAATAIYRIESGPVKLFVIPGGSEEASVLHVTRSVA RRVERNAVKYTKELPEINRMIIVYLNRLSSLLFAMALVANK RRNQSEKIYEIGKSW | I53-51A: 80, 83, 86, 87, 88, 90, 91, 94, 166, 172, 176 |
| I53-51B SEQ ID NO: 10 | (M)NQHSHKDYETVRIAVVRARWHADIVDQCVRAFEEAMAD AGGDRFAVDVFDVPGAYEIPLHARTLAETGRYGAVLGTAFV VNGGIYRHEFVASAVIDGMMNVQLSTGVPVLSAVLTPHRYR SSREHHEFFREHFMVKGVEAAAACITILAAREKIAA | I53-51B: 31, 35, 36, 40, 122, 124, 128, 131, 135, 139, 143, 146, 147 |
| I52-03A SEQ ID NO: 11 | (M)GHTKGPTPQQHDGSALRIGIVHARWNKTIIMPLLIGTI AKLLECGVKASNIVVQSVPGSWELPIAVQRLYSASQLQTPS SGPSLSAGDLLGSSTTDLTALPTTTASSTGPFDALIAIGVL IKGETMHFEYIADSVSHGLMRVQLDTGVPVIFGVLTVLTDD QAKARAGVIEGSHNHGEDWGLAAVEMGVRRRDWAAGKTE | I52-03A: 28, 32, 36, 39, 44, 49 |
| I52-03B SEQ ID NO: 12 | (M)YEVDHADVYDLFYLGRGKDYAAEASDIADLVRSRTPEA SSLLDVACGTGTHLEHFTKEFGDTAGLELSEDMLTHARKRL PDATLHQGDMRDFQLGRKFSAVVSMFSSVGYLKTVAELGAA VASFAEHLEPGGVVVVEPWWFPETFADGWVSADVVRRDGRT VARVSHSVREGNATRMEVHFTVADPGKGVRHFSDVHLITLF HQREYEAAFMAAGLRVEYLEGGPSGRGLFVGVPA | I52-03B: 94, 115, 116, 206, 213 |
| I52-32A SEQ ID NO: 13 | (M)GMKEKFVLIITHGDFGKGLLSGAEVIIGKQENVHTVGL NLGDNIEKVAKEVMRIIAKLAEDKEIIIVVDLFGGSPFNI ALEMMKTFDVKVITGINMPMLVELLTSINVYDTTELLENIS KIGKDGIKVIEKSSLKM | I52-32A: 47, 49, 53, 54, 57, 58, 61, 83, 87, 88 |
| I52-32B SEQ ID NO: 14 | (M)KYDGSKLRIGILHARWNLEIIAALVAGAIKRLQEFGVK AENIIIETVPGSFELPYGSKLFVEKQKRLGKPLDAIIPIGV LIKGSTMHFEYICDSTTHQLMKLNFELGIPVIFGVLTCLTD EQAEARAGLIEGKMHNHGEDWGAAAVEMATKFN | I52-32B: 19, 20, 23, 30, 40 |

TABLE 1-continued

| Name | Amino Acid Sequence | Identified interface residues |
|---|---|---|
| I52-33A SEQ ID NO: 15 | (M)AVKGLGEVDQKYDGSKLRIGILHARWNRKIILALVAGA VLRLLEFGVKAENIIIETVPGSFELPYGSKLFVEKQKRLGK PLDAIIPIGVLIKGSTMHFEYICDSTTHQLMKLNFELGIPV IFGVLTCLTDEQAEARAGLIEGKMHNHGEDWGAAAVEMATK FN | I52-33A: 33, 41, 44, 50 |
| I52-33B SEQ ID NO: 16 | (M)GANWYLDNESSRLSFTSTKNADIAEVHRFLVLHGKVDP KGLAEVEVETESISTGIPLRDMLLRVLVFQVSKFPVAQINA QLDMRPINNLAPGAQLELRLPLTVSLRGKSHSYNAELLATR LDERRFQVVTLEPLVIHAQDFDMVRAFNALRLVAGLSAVSL SVPVGAVLIFTAR | I52-33B: 61, 63, 66, 67, 72, 147, 148, 154, 155 |
| I32-06A SEQ ID NO: 17 | (M)TDYIRDGSAIKALSFAIILAEADLRHIPQDLQRLAVRV IHACGMVDVANDLAFSEGAGKAGRNALLAGAPILCDARMVA EGITRSRLPADNRVIYTLSDPSVPELAKKIGNTRSAAALDL WLPHIEGSIVAIGNAPTALFRLFELLDAGAPKPALIIGMPV GFVGAAESKDELAANSRGVPYVIVRGRRGGSAMTAAAVNAL ASERE | I32-06A: 9, 12, 13, 14, 20, 30, 33, 34 |
| I32-06B SEQ ID NO: 18 | (M)ITVFGLKSKLAPRREKLAEVIYSSLHLGLDIPKGKHAI RFLCLEKEDFYYPFDRSDDYTVIEINLMAGRSEETKMLLIF LLFIALERKLGIRAHDVEITIKEQPAHCWGFRGRTGDSARD LDYDIYV | I32-06B: 24, 71, 73, 76, 77, 80, 81, 84, 85, 88, 114, 118 |
| I32-19A SEQ ID NO: 19 | (M)GSDLQKLQRFSTCDISDGLLNVYNIPIGGYFPNLTAIS PPQNSSIVGTAYTVLFAPIDDPRPAVNYIDSVPPNSILVLA LEPHLQSQFHPFIKITQAMYGGLMSTRAQYLKSNGTVVFGR IRDVDEHRTLNHPVFAYGVGSCAPKAVVKAVGTNVQLKILT SDGVTQTICPGDYIAGDNNGIVRIPVQETDISKLVTYIEKS IEVDRLVSEAIKNGLPAKAAQTARRMVLKDYI | I32-19A: 208, 213, 218, 222, 225, 226, 229, 233 |
| I32-19B SEQ ID NO: 20 | (M)SGMRVYLGADHAGYELKQAIIAFLKMTGHEPIDCGALR YDADDDYPAFCIAAATRTVADPGSLGIVLGGSGNGEQIAAN KVPGARCALAWSVQTAALAREHNNAQLIGIGGRMHTLEEAL RIVKAFVTTPWSKAQRHQRRIDILAEYERTHEAPPVPGAPA | I32-19B: 20, 23, 24, 27, 117, 118, 122, 125 |
| I32-28A SEQ ID NO: 21 | (M)GDDARIAAIGDVDELNSQIGVLLAEPLPDDVRAALSAI QHDLFDLGGELCIPGHAAITEDHLLRLALWLVHYNGQLPPL EEFILPGGARGAALAHVCRTVCRRAERSIKALGAsEPLNIA PAAYVNLLSDLLFVLARVLNRAAGGADVLWDRTRAH | I32-28A: 60, 61, 64, 67, 68, 71, 110, 120, 123, 124, 128 |
| I32-28B SEQ ID NO: 22 | (M)ILSAEQSFTLRHPHGQAAALAFVREPAAALAGVQRLRG LDSDGEQVWGELLVRVPLLGEVDLPFRSEIVRTPQGAELRP LTLTGERAWVAVSGQATAAEGGEMAFAFQFQAHLATPEAEG EGGAAFEVMVQAAAGVTLLLVAMALPQGLAAGLPPA | I32-28B: 35, 36, 54, 122, 129, 137, 140, 141, 144, 148 |
| I53-40A.1 SEQ ID NO: 23 | (M)TKKVGIVDTTFARVDMASAAILTLKMESPNIKIIRKTV PGIKDLPVACKKLLEEEGCDIVMALGMPGKKEKDKVCAHEA SLGLMLAQLMTNKHIIEVFVHEDEAKDDAELKILAARRAIE HALNVYYLLFKPEYLTRMAGKGLRQGFEDAGPARE | I53-40A: 20, 23, 24, 27, 28, 109, 112, 113, 116, 120, 124 |
| I53-40B.1 SEQ ID NO: 24 | (M)DDINNQLKRLKVIPVIAIDNAEDIIPLGKVLAENGLPA AEITFRSSAAVKAIMLLRSAQPEMLIGAGTILNGVQALAAK EAGADFVVSPGFNPNTVRACQIIGIDIVPGVNNPSTVEQAL EMGLTTLKFFPAEASGGISMVKSLVGPYGDIRLMPTGGITP DNIDNYLAIPQVLACGGTWMVDKKLVRNGEWDEIARLTREI VEQVNP | I53-40B: 47, 51, 54, 58, 74, 102 |
| I53-47A.1 SEQ ID NO: 25 | (M)PIFTLNTNIKADDVPSDFLSLTSRLVGLILSKPGSYVA VHINTDQQLSFGGSTNPAAFGTLMSIGGIEPDKNRDHSAVL FDHLNAMLGIPKNRMYIHFVNLNGDDVGWNGTTF | I53-47A: 22, 25, 29, 72, 79, 86, 87 |
| I53-47A.1NegT2 SEQ ID NO: 26 | (M)PIFTLNTNIKADDVPSDFLSLTSRLVGLILSEPGSYVA VHINTDQQLSFGGSTNPAAFGTLMSIGGIEPDKNEDHSAVL FDHLNAMLGIPKNRMYIHFVDLDGDDVGWNGTTF | I53-47A: 22, 25, 29, 72, 79, 86, 87 |
| I53-47B.1 SEQ ID NO: 27 | (M)NQHSKDHETVRIAVVRARWHADIVDACVEAFEIAMAA IGGDRFAVDVFDVPGAYEIPLHARTLAETGRYGAVLGTAFV VNGGIYRHEFVASAVIDGMMNVQLDTGVPVLSAVLTPHRYR DSDEHHRFFAAHFAVKGVEAARACIEILNAREKIAA | I53-47B: 28, 31, 35, 36, 39, 131, 132, 135, 139, 146 |
| I53-47B.1NegT2 | (M)NQHSKDHETVRIAVVRARWHADIVDACVEAFEIAMAA IGGDRFAVDVFDVPGAYEIPLHARTLAETGRyGAVLGTAFV | I53-47B: 28, 31, 35, 36, 39, 131, 132, 135, |

TABLE 1-continued

| Name | Amino Acid Sequence | Identified interface residues |
|---|---|---|
| SEQ ID NO: 28 | VDGGIYDHEFVASAVIDGMMNVQLDTGVPVLSAVLTPHEYE DSDEDHEFFAAHFAVKGVEAARACIEILNAREKIAA | 139, 146 |
| I53-50A.1 SEQ ID NO: 29 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCEWFKAGVLAVGVGDALVKGDPDEVREKAKKFVEKIRGC TE | I53-50A: 25, 29, 33, 54, 57 |
| I53-50A.1NegT2 SEQ ID NO: 30 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPEFVEAMKGPFPNVKFVPTGGVDLD DVCEWFDAGVLAVGVGDALVEGDPDEVREDAKEFVEEIRGC TE | I53-50A: 25, 29, 33, 54, 57 |
| I53-50A.1PosT1 SEQ ID NO: 31 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCKWFKAGVLAVGVGKALVKGKPDEVREKAKKFVKKIRGC TE | I53-50A: 25, 29, 33, 54, 57 |
| I53-50B.1 SEQ ID NO: 32 | (M)NQHSHKDHETVRIAVVRARWHAEIVDACVSAFEAAMRD IGGDRFAVDVFDVPGAYEIPLHARTLAETGRYGAVLGTAFV VNGGIYRHEFVASAVIDGMMNVQLDTGVPVLSAVLTPHRYR DSDAHILLFLALFAVKGMEAARACVEILAAREKIAA | I53-50B: 24, 28, 36, 124, 125, 127, 128, 129, 131, 132, 133, 135, 139 |
| I53-50B.1NegT2 SEQ ID NO: 33 | (M)NQHSHKDHETVRIAVVRARWHAEIVDACVSAFEAAMRD IGGDRFAVDVFDVPGAYEIPLHARTLAETGRYGAVLGTAFV VDGGIYDHEFVASAVIDGMMNVQLDTGVPVLSAVLTPHEYE DSDADTLLFLALFAVKGMEAARACVEILAAREKIAA | I53-50B: 24, 28, 36, 124, 125, 127, 128, 129, 131, 132, 133, 135, 139 |
| I53-50B.4PosT1 SEQ ID NO: 34 | (M)NQHSHKDHETVRIAVVRARWHAEIVDACVSAFEAAMRD IGGDRFAVDVFDVPGAYEIPLHARTLAETGRYGAVLGTAFV VNGGIYRHEFVASAVINGMMNVQLNTGVPVLSAVLTPHNYD KSKAHTLLFLALFAVKGMEAARACVEILAAREKIAA | I53-50B: 24, 28, 36, 124, 125, 127, 128, 129, 131, 132, 133, 135, 139 |

I53-40A genus
(SEQ ID NO: 35)
(M)TKKVGIVDTTFARVDMASAAILTLKMESPNIKIIRKTVPGIKDLPVACKKLLEEEGCDIVMA

LGMPGK(A/K)EKDKVCAHEASLGLMLAQLMTNKHIIEVFVHEDEAKDDAELKILAARRAIEHAL

NVYYLLFKPEYLTRMAGKGLRQGFEDAGPARE

I53-40B genus
(SEQ ID NO: 36)
(M)

(S/D)(T/D)INNQLK(A/R)LKVIPVIAIDNAEDIIPLGKVLAENGLPAAEITFRSSAAVKAIM

LLRSAQPEMLIGAGTILNGVQALAAKEAGA(T/D)FVVSPGFNPNTVRACQIIGIDIVPGVNNPS

TVE(A/Q)ALEMGLTTLKFFPAEASGGISMVKSLVGPYGDIRLMPTGGITP(S/D)NIDNYLAIP

QVLACGGTWMVDKKLV(T/R)NGEWDEIARLTREIVEQVNP

I53-47A genus
(SEQ ID NO: 37)
(M)PIFTLNTNIKA(T/D)DVPSDFLSLTSRLVGLILS(K/E)PGSYVAVHINTDQQLSFGGSTN

PAAFGTLMSIGGIEP(S/D)KN(R/E)DHSAVLFDHLNAMLGIPKNRMYIHFV(N/D)L(N/D)G

DDVGWNGTTF

I53-47B genus
(SEQ ID NO: 38)
(M)NQHSHKD(Y/H)ETVRIAVVRARWHADIVDACVEAFEIAMAAIGGDRFAVDVFDVPGAYEIP

LHARTLAETGRYGAVLGTAFVV(N/D)GGIY(R/D)HEFVASAVIDGMMNVQL(S/D)TGVPVLS

```
AVLTPH(R/E)Y(R/E)DS(A/D)E(H/D)H(R/E)FFAAHFAVKGVEAARACIEIL(A/N)ARE

KIAA

I53-50A genus
                                                      (SEQ ID NO: 39)
(M)KMEELFKKHKIVAVLRANSVEEAIEKAVAVFAGGVHLIEITFTVPDADTVIKALSVLKEKGA

IIGAGTVISVEQCRKAVESGAEFIVSPHLDEEISQFCKEKGVFYMPGVMTPTELVKAMKLGH(T/

D)ILKLFPGEVVGP(Q/E)FV(K/E)AMKGPFPNVKFVPTGGV(N/D)LD(N/D)VC(E/K)WF (K/D)AGVLAVGVG(S/K/D)ALV(K/E)G(T/D/K)PDEVRE(K/D)AK(A/E/K)FV(E/K)

(K/E)IRGCTE

I53-50B genus
                                                      (SEQ ID NO: 40)
(M)NQHSHKD(Y/H)ETVRIAVVRARWHAEIVDACVSAFEAAM(A/R)DIGGGDRFAVDVFDVPGA

YEIPLHARTLAETGRYGAVLGTAFVV(N/D)GGIY(R/D)HEFVASAVI(D/N)GMMNVQL(S/

D/N)TGVPVLSAVLTPH(R/E/N)Y(R/D/E)(D/K)S(D/K)A(H/D)TLLFLALFAVKGMEAA

RACVEILAAREKIAA

T32-28A
                                                      (SEQ ID NO: 41)
(M)GEVPIGDPKELNGMEIAAVYLQPIEMEPRGIDLAASLADIHLEADIHALKNNPNGFPEGFWM

PYLTIAYALANADTGAIKTGTLMPMVADDGPHYGANIAMEKDKKGGFGVGTYALTFLISNPEKQG

FGRHVDEETGVGKWFEPFVVTYFFKYTGTPK

T32-28B
                                                      (SEQ ID NO: 42)
(M)SQAIGILELTSIAKGMELGDAMLKSANVDLLVSKTISPGKFLLMLGGDIGAIQQAIETGTSQ

AGEMLVDSLVLANIHPSVLPAISGLNSVDKRQAVGIVETWSVAACISAADLAVKGSNVTLRVHM

AFGIGGKCYMVVAGDVLDVAAAVATASLAAGAKGLLVYASIIPRPHEAMWRQMVEG

T33-09A
                                                      (SEQ ID NO: 43)
(M)EEVVLITVPSALVAVKIAHALVEERLAACVNIVPGLTSIYRWQGSVVSDHELLLLVKTTTHA

FPKLKERVKALHPYTVPEIVALPIAEGNREYLDWLRENTG

T33-09B
                                                      (SEQ ID NO: 44)
(M)VRGIRGAITVEEDTPAAILAATIELLLKMLEANGIQSYEELAAVIFTVTEDLTSAFPAEAAR

LIGMHRVPLLSAREVPVPGSLPRVIRVLALWNTDTPQDRVRHVYLNEAVRLRPDLESAQ

T33-15A
                                                      (SEQ ID NO: 45)
(M)SKAKIGIVTVSDRASAGITADISGKAIILALNLYLTSEWEPIYQVIPDEQDVIETTLIKMAD

EQDCCLIVTIGGIGPAKRDVTPEATEAVCDRMMPGFGELMRAESLKEVPTAILSRQTAGLRGDSL

IVNLPGDPASISDCLLAVFPAIPYCIDLMEGPYLECNEAMIKPFRPKAK

T33-15B
                                                      (SEQ ID NO: 46)
(M)VRGIRGAITVNSDTPTSIIIATILLLEKMLEANGIQSYEELAAVIFTVTEDLTSAFPAEAAR

QIGMHRVPLLSAREVPVPGSLPRVIRVLALWNTDTPQDRVRHVYLSEAVRLRPDLESAQ

T33-21A
                                                      (SEQ ID NO: 47)
(M)RITTKVGDKGSTRLFGGEEVWKDSPIIEANGTLDELTSFIGEAKHYVDEEMKGILEEIQNDI

YKIMGEIGSKGKIEGISEERIAWLLKLILRYMEMVNLKSFVLPGGTLESAKLDVCRTIARRALRK

VLIVTREFGIGAEAAAYLLALSDLLFLLARVIEIEKNKLKEVRS

T33-21B
                                                      (SEQ ID NO: 48)
(M)PHLVIEATANLRLETSPGELLEQANKALFASGQFGEADIKSRFVTLEAYRQGTAAVERAYLH

ACLSILDGRDIATRTLLGASLCAVLAEAVAGGGEEGVQVSVEVREMERLSYAKRVVARQR
```

-continued

T33-28A
(SEQ ID NO: 49)
(M)ESVNTSFLSPSLVTIRDFDNGQFAVLRIGRTGFPADKGDIDLCLDKMIGVRAAQIFLGDDTE

DGFKGPHIRIRCVDIDDKHTYNAMVYVDLIVGTGASEVERETAEEEAKLALRVALQVDIADEHSC

VTQFEMKLREELLSSDSFHPDKDEYYKDFL

T33-28B
(SEQ ID NO: 50)
(M)PVIQTFVSTPLDHHKRLLLAIIYRIVTRVVLGKPEDLVMMTFHDSTPMHFFGSTDPVACVRV

EALGGYGPSEPEKVTSIVTAAITAVCGIVADRIFVLYFSPLHCGWNGTNF

T33-31A
(SEQ ID NO: 51)
(M)EEVVLITVPSALVAVKIAHALVEERLAACVNIVPGLTSIYREEGSVVSDHELLLLVKTTTDA

FPKLKERVKELHPYEVPEIVALPIAEGNREYLDWLRENTG

Table 1 provides the amino acid sequence of the first and second polypeptides; the right hand column in Table 1 identifies the residue numbers in each exemplary polypeptide that were identified as present at the interface of resulting assembled nanostructures (i.e.: "identified interface residues"). As can be seen, the number of interface residues for the exemplary polypeptides of SEQ ID NO:1-34 range from 4-13. In various embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given polypeptide), to the amino acid sequence of a polypeptide selected from the group consisting of SEQ ID NOS: 1-34. In other embodiments, the first and second polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a polypeptide selected from the group consisting of SEQ ID NOS:1-51.

As is the case with proteins in general, the polypeptides are expected to tolerate some variation in the designed sequences without disrupting subsequent assembly into nanostructures: particularly when such variation comprises conservative amino acid substitutions. As used here, "conservative amino acid substitution" means that: hydrophobic amino acids (Ala, Cys, Gly, Pro, Met, See, Sme, Val, Ile, Leu) can only be substituted with other hydrophobic amino acids; hydrophobic amino acids with bulky side chains (Phe, Tyr, Trp) can only be substituted with other hydrophobic amino acids with bulky side chains; amino acids with positively charged side chains (Arg, His, Lys) can only be substituted with other amino acids with positively charged side chains; amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

Table 2 lists surface amino acid residue numbers for each exemplary polypeptide of the invention denoted by SEQ ID NOS: 1-34. Thus, in various embodiments, 1 or more (at least 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47, 48, 49, 50, or more) of these surface residues may be modified in the polypeptides of the invention. Residues in parentheses are optional.

TABLE 2

| Name | Amino Acid Sequence | Surface residues not near interface |
|---|---|---|
| I53-34A SEQ ID NO: 1 | (M)EGMDPLAVLAESRLLPLLTVRGGEDLAGLATVLELMGV GALEITLRTEKGLEALKALRKSGLLLGAGTVRSPKEAEAAL EAGAAFLVSPGLLEEVAALAQARGVPYLPGVLTPTEVERAL ALGLSALKFFPAEPFQGVRVLRAYAEVFPEVRFLPTGGIKE EHLPHYAALPNLLAVGGSWLLQGDLAAVMKKVKAAKALLSP QAPG | I53-34A: 6, 8, 9, 12, 14, 22, 25, 48, 49, 50, 52, 53, 56, 73, 74, 81, 94, 95, 101, 102, 103, 104, 119, 122, 137, 140, 143, 147, 150, 151, 153, 161, 162, 163, 164, 166, 167, 170, 172, 184, 193, 198, 199, 200, 202 |
| I53-34B SEQ ID NO: 2 | (M)TKKVGIVDTTFARVDMAEAAIRTLKALSPNIKIIRKTV PGIKDLPVACKKLLEEEGCDIVMALGMPGKAEKDKVCAHEA SLGLMLAQLMTNKHIIEVFVHEDEAKDDDELDILALVRAIE HAANVYYLLFKPEYLTRMAGKGLRQGREDAGPARE | I53-34B: 3, 12, 31, 33, 35, 36, 51, 54, 55, 56, 59, 69, 70, 71, 74, 93, 103, 106, 107, 108, 131, 132, 133, 134, 138, 142, 153 |
| I53-40A SEQ ID NO: 3 | (M)TKKVGIVDTTFARVDMASAAILTLKMESPNIKIIRKTV PGIKDLPVACKKLLEEEGCDIVMALGMPGKAEKDKVCAHEA SLGLMLAQLMTNKHIIEVFVHEDEAKDDAELKILAARRAIE HALNVYYLFKPEYLTRMAGKGLRQGFEDAGPARE | I53-40A: 3, 4, 31, 33, 35, 36, 37, 51, 54, 55, 56, 57, 59, 69, 70, 71, 74, 93, 103, 106, 118, 127, 128, 131, 132, 133, 134, 135, 138, 139, 142, 150, 153 |

TABLE 2-continued

| Name | Amino Acid Sequence | Surface residues not near interface |
|---|---|---|
| I53-40B SEQ ID NO: 4 | (M)STINNQLKALKVIPVIAIDNAEDIIPLGKVLAENGLPA AEITFRSSAAVKAIMLLRSAQPEMLIGAGTILNGVQALAAK EAGATFVVSPGFNPNTVRACQIIGIDIVPGVNNPSTVEAAL EMGLTTLKFFPAEASGGISMVKSLVGPYGDIRLMPTGGITP SNIDNYLAIPQVLACGGTWMVDKKLVINGEWDEIARLTREI VEQVNP | I53-40B: 2, 3, 7, 9, 10, 12, 20, 21, 23, 26, 27, 30, 34, 38, 45, 60, 62, 75, 85, 94, 95, 122, 124, 126, 134, 139, 143, 151, 153, 161, 163, 166, 167, 170, 172, 180, 184, 185, 186, 189, 190, 192, 193, 194, 195, 198, 201, 202, 205, 208, 209 |
| I53-47A SEQ ID NO: 5 | (M)PIFTLNTNIKATDVPSDFLSLTSRLVGLILSKPGSYVA VHINTDQQLSFGGSTNPAAFGTLMSIGGIEPSKNRDHSAVL FDHLNAMLGIPKNRMYIHFVNLNGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47B SEQ ID NO: 6 | (M)NQHSHKDYETVRIAVVRARWHADIVDACVEAFEIAMAA IGGDRFAVDVFDVPGAYEIPLHARTLAETGRYGAVLGTAFV VNGGIYRHEFVASAVIDGMMNVQLSTGVPVLSAVLTPHRYR DSAEHHRFFAAHFAVKGVEAARACIEILAAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-50A SEQ ID NO: 7 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHTILKLFPPGEVVGPQFVKAMKGPFPNVKFVPTGGVNLD NVCEWFKAGVLAVGVGSALVKGTPDEVREKAKAFVEKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50B SEQ ID NO: 8 | (M)NQHSHKDYETVRIAVVRARWHAEIVDACVSAFEAAMAD IGGDRFAVDVFDVPGAYEIPLHARTLAETGRYGAVLGTAFV VNGGIYRHEFVASAVIDGMMNVQLSTGVPVLSAVLTPHRYR DSDAHILLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |
| I53-51A SEQ ID NO: 9 | (M)FIKSGDDGNINVINKRVGKDSPLVNFLGDLDELNSFIG FAISKIPWEDMKKDLERVQVELFEIGEDLSTQSSKKKIDES YVLWLLAATAIYRIESGPVKLFVIPGGSEEASVLHVTRSVA RRVERNAVKYTKELPEINRMIIVYLNRLSSLLFAMALVANK RRNQSEKIYEIGKSW | I53-51A: 19, 20, 24, 28, 46, 47, 51, 70, 71, 73, 74, 75, 76, 102, 122, 130, 133, 134, 135, 136, 137, 140, 162, 163, 164, 165, 169, 175, 177 |
| I53-51B SEQ ID NO: 10 | (M)NQHSHKDYETVRIAVVRARWHADIVDQCVRAFEEAMAD AGGDRFAVDVFDVPGAYEIPLHARTLAETGRYGAVLGTAFV VNGGIYRHEFVASAVIDGMMNVQLSTGVPVLSAVLTPHRYR SSREHHEFFREHFMVKGVEAAAACITILAAREKIAA | I53-51B: 6, 7, 8, 9, 10, 11, 13, 18, 21, 27, 34, 38, 43, 48, 63, 67, 70, 85, 87, 101, 118, 125, 126, 129, 152, 153, 154 |
| I52-03A SEQ ID NO: 11 | (M)GHTKGPTPQQHDGSALRIGIVHARWNKTIIMPLLIGTI AKLLECGVKASNIVVQSVPGSWELPIAVQRLYSASQLQTPS SGPSLSAGDLLGSSTTDLTALPTTTASSTGPFDALIAIGVL IKGETMHFEYIADSVSHGLMRVQLDTGVPVIFGVLTVLTDD QAKARAGVIEGSHNHGEDWGLAAVEMGVRRRDWAAGKTE | I52-03A: 6, 9, 10, 11, 13, 15, 16, 26, 48, 69, 75, 76, 78, 79, 111, 125, 127, 142, 146, 159, 160, 161, 162, 171, 175, 193, 194, 196, 197, 199, 200 |
| I52-03B SEQ ID NO: 12 | (M)YEVDHADVYDLFYLGRGKDYAAEASDIADLVRSRTPEA SSLLDVACGTGTHLEHFTKEFGDTAGLELSEDMLTHARKRL PDATLHQGDMRDFQLGRKFSAVVSMFSSVGYLKTVAELGAA VASFAEHLEPGGVVVVEPWWFPETFADGWVSADVVRRDGRT VARVSHSVREGNATRMEVHFTVADPGKGVRHFSDVHLITLF HQREYEAAFMAAGLRVEYLEGGPSGRGLFVGVPA | I52-03B: 2, 3, 5, 6, 8, 15, 17, 20, 22, 23, 26, 27, 30, 33, 34, 35, 37, 38, 40, 54, 55, 57, 58, 59, 61, 62, 68, 70, 71, 74, 77, 78, 79, 81, 82, 84, 86, 87, 91, 96, 97, 98, 111, 127, 130, 131, 132, 141, 144, 145, 148, 150, 154, 157, 158, 159, 160, 161, 171, 172, 173, 174, 177, 187, 189, 192, 198, 199, 222, 223, 224, 236 |

TABLE 2-continued

| Name | Amino Acid Sequence | Surface residues not near interface |
|---|---|---|
| I52-32A SEQ ID NO: 13 | (M)GMKEKFVLIITHGDFGKGLLSGAEVIIGKQENVHTVGL NLGDNIEKVAKEVMRIIIAKLAEDKEIIIVVDLFGGSPFNI ALEMMKTFDVKVITGINMPMLVELLTSINVYDTTELLENIS KIGKDGIKVIEKSSLKM | I52-32A: 3, 5, 15, 18, 30, 32, 35, 40, 41, 42, 44, 45, 65, 73, 79, 91, 103, 106, 109, 110, 111, 112, 114, 115, 118, 122, 123, 125, 126, 129, 131 |
| I52-32B SEQ ID NO: 14 | (M)KYDGSKLRIGILHARWNLEIIAALVAGAIKRLQEFGVK AENIIETVPGSFELPYGSKLFVEKQKRLGKPLDAIIPIGV LIKGSTMHFEYICDSTTHQLMKLNFELGIPVIFGVLTCLTD EQAEARAGLIEGKMHNHGEDWGAAAVEMATKFN | I52-32B: 4, 6, 7, 9, 17, 32, 35, 42, 59, 63, 64, 66, 67, 68, 69, 70, 71, 73, 83, 85, 90, 106, 119, 120, 121, 122, 125, 131, 133, 134, 135, 136, 154 |
| I52-33A SEQ ID NO: 15 | (M)AVKGLGEVDQKYDGSKLRIGILHARWNRKIILALVAGA VLRLLEFGVKAENIIETVPGSFELPYGSKLFVEKQKRLGK PLDAIIPIGVLIKGSTMHFEYICDSTTHQLMKLNFELGIPV IFGVLTCLTDEQAEARAGLIEGKMHNHGEDWGAAAVEMATK FN | I52-33A: 12, 14, 16, 17, 19, 26, 27, 46, 69, 73, 74, 76, 77, 78, 80, 81, 83, 93, 95, 100, 116, 129, 130, 131, 132, 145, 164 |
| I52-33B SEQ ID NO: 16 | (M)GANWYLDNESSRLSFTSTKNADIAEVHRFLVLHGKVDP KGLAEVEVETESISTGIPLRDMLLRVLVFQVSKFPVAQINA QLDMRPINNLAPGAQLELRLPLTVSLRGKSHSYNAELLATR LDERRFQVVTLEPLVIHAQDFDMVRAFNALRLVAGLSAVSL SVPVGAVLIFTAR | I52-33B: 4, 6, 10, 20, 21, 23, 24, 31, 32, 34, 36, 39, 40, 42, 44, 46, 48, 56, 73, 77, 81, 83, 85, 88, 89, 91, 92, 96, 97, 99, 101, 103, 109, 110, 111, 112, 114, 124, 125, 138, 140, 143, 158, 175 |
| I32-06A SEQ ID NO: 17 | (M)TDYIRDGSAIKALSFAIILAEADLRHIPQDLQRLAVRV IHACGMVDVANDLAFSEGAGKAGRNALLAGAPILCDARMVA EGITRSRLPADNRVIYTLSDPSVPELAKKIGNTRSAAALDL WLPHIEGSIVAIGNAPTALFRLFELLDAGAPKPALIIGMPV GFVGAAESKDELAANSRGVPYVIVRGRRGGSAMTAAAVNAL ASERE | I32-06A: 24, 26, 27, 41, 47, 50, 51, 56, 60, 63, 64, 67, 68, 77, 84, 85, 86, 91, 93, 98, 99, 100, 101, 102, 105, 108, 109, 114, 123, 124, 125, 127, 135, 142, 145, 148, 149, 152, 153, 169, 172, 173, 176, 177, 180, 187, 189 |
| I32-06B SEQ ID NO: 18 | (M)ITVFGLKSKLAPRREKLAEVIYSSLHLGLDIPKGKHAI RFLCLEKEDFYYPFDRSDDYTVIEINLMAGRSEETKMLLIF LLFIALERKLGIRAHDVEITIKEQPAHCWGFRGRTGDSARD LDYDIYV | I32-06B: 8, 9, 10, 13, 14, 15, 16, 17, 20, 34, 36, 45, 46, 47, 50, 51, 53, 54, 57, 67, 70, 91, 93, 95, 105, 112 |
| I32-19A SEQ ID NO: 19 | (M)GSDLQKLQRFSTCDISDGLLNVYNIPIGGYFPNLTAIS PPQNSSIVGTAYTVLFAPIDDPRPAVNYIDSVPPNSILVLA LEPHLQSQFHPFIKITQAMYGGLMSTRAQYLKSNGTVVFGR IRDVDEHRTLNHPVFAYGVGSCAPKAVVKAVGTNVQLKILT SDGVTQTICPGDYIAGDNNGIVRIPVQETDISKLVTYIEKS IEVDRLVSEAIKNGLPAKAAQTARRMVLKDYI | I32-19A: 3, 4, 6, 7, 9, 10, 25, 27, 36, 40, 42, 43, 44, 49, 58, 59, 61, 62, 63, 70, 72, 73, 74, 82, 84, 88, 89, 109, 110, 112, 126, 127, 129, 130, 132, 146, 155, 156, 157, 159, 166, 169, 172, 189, 190, 192, 194, 195, 198, 201, 204, 215, 232 |
| I32-19B SEQ ID NO: 20 | (M)SGMRVYLGADHAGYELKQAIIAFLKMTGHEPIDCGALR YDADDDYPAFCIAAATRTVADPGSLGIVLGGSGNGEQIAAN KVPGARCALAWSVQTAALAREHNNAQLIGIGGRMHTLEEAL RIVKAFVTTPWSKAQRHQRRIDILAEYERTHEAPPVPGAPA | I32-19B: 4, 5, 31, 33, 38, 41, 42, 43, 55, 56, 59, 61, 62, 83, 93, 94, 101, 104, 113, 119, 129, 131, 134, 136, 137, 139, 140, 143, 144, 146, 147, 150, 152, 153, 156, 158, 159 |
| I32-28A SEQ ID NO: 21 | (M)GDDARIAAIGDVDELNSQIGVLLAEPLPDDVRAALSAI QHDLFDLGGELCIPGHAAITEDHLLRLALWLVHYNGQLPPL EEFILPGGARGAALAHVCRTVCRRAERSIKALGASEPLNIA PAAYVNLLSDLLFVLARVLNRAAGGADVLWDRTRAH | I32-28A: 4, 6, 7, 10, 14, 27, 30, 31, 33, 34, 41, 44, 45, 51, 52, 53, 54, 55, 56, 59, 76, 78, 79, 80, 81, 82, 83, 90, 103, 111, 115, 116, 131, 134, 142, 145, 147, 150 |
| I32-28B SEQ ID NO: 22 | (M)ILSAEQSFTLRHPHGQAAALAFVREPAAALAGVQRLRG LDSDGEQVWGELLRVPLLGEVDLPFRSEIVRTPQGAELRP LTLTGERAWVAVSGQATAAEGGEMAFAFQFQAHLATPEAEG EGGAAFEVMVQAAAGVTLLLVAMALPQGLAAGLPPA | I32-28B: 3, 4, 6, 8, 12, 15, 17, 18, 22, 26, 28, 32, 38, 39, 41, 43, 45, 46, 48, 50, 60, 66, 68, 71, 73, 74, 79, 81, 82, 83, |

TABLE 2-continued

| Name | Amino Acid Sequence | Surface residues not near interface |
|---|---|---|
| | | 84, 86, 87, 95, 100, 103, 105, 109, 111, 113, 151, 152, 155, 156, 157 |
| I53-40A.1 SEQ ID NO: 23 | (M)TKKVGIVDTTFARVDMASAAILTLKMESPNIKIIRKTV PGIKDLPVACKKLLEEEGCDIVMALGMPGKKEKDKVCAHEA SLGLMLAQLMTNKHIIEVFVHEDEAKDDAELKILAARRAIE HALNVYYLLFKPEYLTRMAGKGLRQGFEDAGPARE | I53-40A: 3, 4, 31, 33, 35, 36, 37, 51, 54, 55, 56, 57, 59, 69, 70, 71, 74, 93, 103, 106, 118, 127, 128, 131, 132, 133, 134, 135, 138, 139, 142, 150, 153 |
| I53-40B.1 SEQ ID NO: 24 | (M)DDINNQLKRLKVIPVIAIDNAEDIIPLGKVLAENGLPA AEITFRSSAAVKAIMLLRSAQPEMLIGAGTILNGVQALAAK EAGADFVVSPGFNPNTVRACQIIGIDIVPGVNNPSTVEQAL EMGLTTLKFFPAEASGGISMVKSLVGPYGDIRLMPTGGITP DNIDNYLAIPQVLACGGTWMVDKKLVRNGEWDEIARLTREI VEQVNP | I53-40B: 2, 3, 7, 9, 10, 12, 20, 21, 23, 26, 27, 30, 34, 38, 45, 60, 62, 75, 85, 94, 95, 122, 124, 126, 134, 139, 143, 151, 153, 161, 163, 166, 167, 170, 172, 180, 184, 185, 186, 189, 190, 192, 193, 194, 195, 198, 201, 202, 205, 208, 209 |
| I53-47A.1 SEQ ID NO: 25 | (M)PIFTLNTNIKADDVPSDFLSLTSRLVGLILSKPGSYVA VHINTDQQLSFGGSTNPAAFGTLMSIGGIEPDKNRDHSAVL FDHLNAMLGIPKNRMYIHFVNLNGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47A.1NegT2 SEQ ID NO: 26 | (M)PIFTLNTNIKADDVPSDFLSLTSRLVGLILSEPGSYVA VHINTDQQLSFGGSTNPAAFGTLMSIGGIEPDKNEDHSAVL FDHLNAMLGIPKNRMYIHFVDLDGDDVGWNGTTF | I53-47A: 11, 13, 14, 17, 34, 36, 37, 45, 47, 54, 55, 56, 65, 69, 70, 71, 74, 91, 92, 93, 101, 103, 105, 109, 110, 112, 114 |
| I53-47B.1 SEQ ID NO: 27 | (M)NQHSHKDHETVRIAVVRARWHADIVDACVEAFEIAMAA IGGDRFAVDVEDVPGAYEIPLHARTLAETGRYGAVLGTAFV VNGGIYRHEFVASAVIDGMMNVQLDTGVPVLSAVLTPHRYR DSDEHHRFFAAHFAVKGVEAARACIEILNAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-47B.1NegT2 SEQ ID NO: 28 | (M)NQHSHKDHETVRIAVVRARWHADIVDACVEAFEIAMAA IGGDRFAVDVEDVPGAYEIPLHARTLAETGRYGAVLGTAFV VDGGIYDHEFVASAVIDGMMNVQLDTGVPVLSAVLTPHEYE DSDEDHEFFAAHFAVKGVEAARACIEILNAREKIAA | I53-47B: 6, 7, 8, 9, 10, 11, 13, 18, 20, 21, 24, 43, 44, 51, 63, 67, 70, 85, 87, 101, 105, 122, 123, 124, 125, 126, 147, 152, 153, 154 |
| I53-50A.1 SEQ ID NO: 29 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCEWFKAGVLAVGVGDALVKGDPDEVREKAKKFVEKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50A.1NegT2 SEQ ID NO: 30 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPEFVEAMKGPFPNVKFVPTGGVDLD DVCEWFDAGVLAVGVGDALVEGDPDEVREDAKEFVEEIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50A.1PosT1 SEQ ID NO: 31 | (M)KMEELFKKHKIVAVLRANSVEEAIEKAVAVFAGGVHLI EITFTVPDADTVIKALSVLKEKGAIIGAGTVTSVEQCRKAV ESGAEFIVSPHLDEEISQFCKEKGVFYMPGVMTPTELVKAM KLGHDILKLFPGEVVGPQFVKAMKGPFPNVKFVPTGGVNLD NVCKWFKAGVLAVGVGKALVKGKPDEVREKAKKFVKKIRGC TE | I53-50A: 4, 5, 6, 8, 9, 11, 17, 19, 23, 37, 46, 47, 59, 74, 77, 78, 81, 94, 95, 98, 101, 102, 103, 106, 119, 122, 126, 139, 142, 145, 149, 150, 152, 160, 161, 162, 163, 166, 169, 179, 183, 185, 188, 191, 192, 194, 198, 199 |
| I53-50B.1 SEQ ID | (M)NQHSHKDHETVRIAVVRARWHAEIVDACVSAFEAAMRD IGGDRFAVDVEDVPGAYEIPLHARTLAETGRYGAVLGTAFV VNGGIYRHEFVASAVIDGMMNVQLDTGVPVLSAVLTPHRYR | I53-50B: 6, 7, 8, 9, 10, 11, 13, 18, 20, 21, 34, 38, 39, 40, 43, 44, 48, 51, 63, |

TABLE 2-continued

| Name | Amino Acid Sequence | Surface residues not near interface |
|---|---|---|
| NO: 32 | DSDAHILLFLALFAVKGMEAARACVEILAAREKIAA | 67, 70, 87, 101, 105, 118, 143, 147, 152, 153, 154 |
| I53-50B.1NegT2 SEQ ID NO: 33 | (M)NQHSHKDHETVRIAVVRARWHAEIVDACVSAFEAAMRD IGGDRFAVDVEDVPGAYEIPLHARTLAETGRYGAVLGTAFV VDGGIYDHEFVASAVIDGMMNVQLDTGVPVLSAVLTPHEYE DSDADTLLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |
| I53-50B.4PosT1 SEQ ID NO: 34 | (M)NQHSHKDHETVRIAVVRARWHAEIVDACVSAFEAAMRD IGGDRFAVDVEDVPGAYEIPLHARTLAETGRYGAVLGTAFV VNGGIYRHEEVASAVINGMMNVQLNTGVPVLSAVLTPHNYD KSKAHTLLFLALFAVKGMEAARACVEILAAREKIAA | I53-50B: 6, 7, 8, 9, 10, 11, 13, 18, 20, 21, 34, 38, 39, 40, 43, 44, 48, 51, 63, 67, 70, 87, 101, 105, 118, 143, 147, 152, 153, 154 |

In various embodiments of the nanostructure of the invention, the first polypeptides and the second polypeptides comprise polypeptides with the amino acid sequence selected from the following pairs, or modified versions thereof (i.e.: permissible modifications as disclosed for the polypeptides of the invention: isolated polypeptides comprising an amino acid sequence that is at least 75% 80%, 85%, 90%, 91%, 92%, 93%, 94%, 95%, 96%, 97%, 98%, 99%, or 100% identical over its length, and/or identical at least at one identified interface position, to the amino acid sequence indicated by the SEQ ID NO.):

SEQ ID NO:1 and SEQ ID NO:2 (I53-34A and I53-34B);
SEQ ID NO:3 and SEQ ID NO:4 (I53-40A and I53-40B);
SEQ ID NO:3 and SEQ ID NO:24 (I53-40A and I53-40B.1);
SEQ ID NO:23 and SEQ ID NO:4 (I53-40A.1 and I53-40B);
SEQ ID NO:35 and SEQ ID NO:36 (I53-40A genus and I53-40B genus);
SEQ ID NO:5 and SEQ ID NO:6 (I53-47A and I53-47B);
SEQ ID NO:5 and SEQ ID NO:27 (I53-47A and I53-47B.1);
SEQ ID NO:5 and SEQ ID NO:28 (I53-47A and I53-47B.1NegT2);
SEQ ID NO:25 and SEQ ID NO:6 (I53-47A.1 and I53-47B);
SEQ ID NO:25 and SEQ ID NO:27 (I53-47A.1 and I53-47B.1);
SEQ ID NO:25 and SEQ ID NO:28 (I53-47A.1 and I53-47B.1NegT2);
SEQ ID NO:26 and SEQ ID NO:6 (I53-47A.1NegT2 and I53-47B);
SEQ ID NO:26 and SEQ ID NO:27 (I53-47A.1NegT2 and I53-47B.1);
SEQ ID NO:26 and SEQ ID NO:28 (I53-47A.1NegT2 and I53-47B.1NegT2);
SEQ ID NO:37 and SEQ ID NO:38 (I53-47A genus and I53-47B genus);
SEQ ID NO:7 and SEQ ID NO:8 (I53-50A and I53-50B);
SEQ ID NO:7 and SEQ ID NO:32 (I53-50A and I53-50B.1);
SEQ ID NO:7 and SEQ ID NO:33 (I53-50A and I53-50B.1NegT2);
SEQ ID NO:7 and SEQ ID NO:34 (I53-50A and I53-50B.4PosT1);
SEQ ID NO:29 and SEQ ID NO:8 (I53-50A.1 and I53-50B);
SEQ ID NO:29 and SEQ ID NO:32 (I53-50A.1 and I53-50B.1);
SEQ ID NO:29 and SEQ ID NO:33 (I53-50A.1 and I53-50B.1NegT2);
SEQ ID NO:29 and SEQ ID NO:34 (I53-50A.1 and I53-50B.4PosT1);
SEQ ID NO:30 and SEQ ID NO:8 (I53-50A.1NegT2 and I53-50B);
SEQ ID NO:30 and SEQ ID NO:32 (I53-50A.1NegT2 and I53-50B.1);
SEQ ID NO:30 and SEQ ID NO:33 (I53-50A.1NegT2 and I53-50B.1NegT2);
SEQ ID NO:30 and SEQ ID NO:34 (I53-50A.1NegT2 and I53-50B.4PosT1);
SEQ ID NO:31 and SEQ ID NO:8 (I53-50A.1PosT1 and I53-50B);
SEQ ID NO:31 and SEQ ID NO:32 (I53-50A.1PosT1 and I53-50B.1);
SEQ ID NO:31 and SEQ ID NO:33 (I53-50A.1PosT1 and I53-50B.1NegT2);
SEQ ID NO:31 and SEQ ID NO:34 (I53-50A.1PosT1 and I53-50B.4PosT1);
SEQ ID NO:39 and SEQ ID NO:40 (I53-50A genus and I53-50B genus);
SEQ ID NO:9 and SEQ ID NO:10 (I53-51A and I53-51B);
SEQ ID NO:11 and SEQ ID NO:12 (I52-03A and I52-03B);
SEQ ID NO:13 and SEQ ID NO:14 (I52-32A and I52-32B);
SEQ ID NO:15 and SEQ ID NO:16 (I52-33A and I52-33B)
SEQ ID NO:17 and SEQ ID NO:18 (I32-06A and I32-06B);
SEQ ID NO:19 and SEQ ID NO:20 (I32-19A and I32-19B);
SEQ ID NO:21 and SEQ ID NO:22 (I32-28A and I32-28B);
SEQ ID NO:23 and SEQ ID NO:24 (I53-40A.1 and I53-40B.1);
SEQ ID NO:41 and SEQ ID NO:42 (T32-28A and T32-28B);
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and SEQ ID NO:51 and SEQ ID NO:44 (T33-31A and T33-09B (also referred to as T33-31B))

In one embodiment, the one or more paramyxovirus and/or pneumovirus F proteins, or antigenic fragments thereof, are expressed as a fusion protein with the first and/or second polypeptides. In these embodiments, it is preferred that the one or more paramyxovirus and/or pneumovirus F proteins, or antigenic fragments thereof are present at the N terminus of the fusion protein, whenever this configuration can facilitate presentation of the one or more paramyxovirus and/or pneumovirus F proteins, or antigenic fragments thereof on an exterior of the nanostructure. This preference for the presence of the paramyxovirus and/or pneumovirus F protein at the N terminus of the fusion protein derives from the location of the C terminus of the paramyxovirus and/or pneumovirus F proteins at one extreme (the "bottom") of the F protein trimer; by locating the genetic fusion at this point, the majority of the F protein structure will be displayed and accessible on the nanostructure exterior. In a further embodiment, the nanostructures comprise one or more copies of a fusion protein comprising at least two domains—a paramyxovirus and/or pneumovirus F protein, or an antigenic fragment thereof, and a trimeric assembly domain (i.e.: each first assembly is a homotrimer of the first polypeptide)—and one or more copies of a second oligomeric block (i.e.: each second assembly is an oligomer of two or more copies of the second polypeptide). In another embodiment, the first and or second polypeptides may be modified to permit the one or more paramyxovirus and/or pneumovirus F proteins, or antigenic fragments thereof, to be covalently linked to the first and/or second polypeptides. In one non-limiting example, the first and/or second polypeptides can be modified, such as by introduction of various cysteine residues at defined positions to facilitate linkage one or more paramyxovirus and/or pneumovirus F proteins, or antigenic fragments thereof.

In other embodiments, the one or more paramyxovirus and/or pneumovirus F proteins, or antigenic fragments thereof are attached to the first or second polypeptides via any suitable technique, including but not limited to covalent chemical cross-linking (via any suitable cross-linking technique) and non-covalent attachment including engineered electrostatic interactions.

Trimeric Assembly Domains

In one embodiment of a trimeric assembly that comprises a trimeric paramyxovirus and/or pneumovirus F protein, or antigenic fragments thereof, the paramyxovirus and/or pneumovirus F protein, or antigenic fragment thereof is genetically fused to the first polypeptides that self-assemble into the trimeric assembly. The trimeric assembly comprises a protein-protein interface that induces three copies of the first polypeptides to self-associate to form trimeric building blocks. Each copy of the first polypeptides further comprises a surface-exposed interface that interacts with a complementary surface-exposed interface on a second assembly domain. As described in King et al. (Nature 510, 103-108, 2014), Bale et al. (Science 353, 389-394, 2016), and patent publications WO2014124301 A1 and US20160122392 A1, the complementary protein-protein interface between the trimeric assembly domain and second assembly domain drives the assembly of multiple copies of the trimeric assembly domain and second assembly domain to a target nanostructure. In some embodiments, each copy of the trimeric assembly domains of the nanostructure bears a paramyxovirus and/or pneumovirus F proteins, or antigenic fragment thereof, as a genetic fusion; these nanostructures display the F proteins at full valency. In other embodiments, the nanostructures of the invention comprise one or more copies of trimeric assembly domains bearing paramyxovirus and/or pneumovirus F proteins, or antigenic fragments thereof as genetic fusions as well as one or more trimeric assembly domains that do not bear F proteins as genetic fusions; these nanostructures display the F proteins at partial valency. The trimeric assembly domain can be any polypeptide sequence that forms a trimer and interacts with a second assembly domain to drive assembly to a target nanostructure.

In one specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-31A (SEQ ID NO:51) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-09B/T33-31B (SEQ ID NO:44) (residues in parentheses are optional)

```
T33-31A
                                          (SEQ ID NO: 51)
(M)EEVVLITVPSALVAVKIAHALVEERLAACVNIVPGLTSIYREEGSV
VSDHELLLLVKITTDAFPKLKERVKELHPYEVPEIVALPIAEGNREYLD
WLRENTG

>T33-31B
                                          (SEQ ID NO: 44)
(M)VRGIRGAITVEEDTPAAILAATIELLLKMLEANGIQSYEELAAVIF
TVTEDLTSAFPAEAARLIGMHRVPLLSAREVPVPGSLPRVIRVLALWNT
DTPQDRVRHVYLNEAVRLRPDLESAQ
```

In another specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15A (SEQ ID NO:45) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15B (SEQ ID NO:46).

In various further specific embodiments, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptides selected from the group consisting of I53-50A (SEQ ID NO:7), I53-50A.1 (SEQ ID NO:29), I53-50A.1NegT2 (SEQ ID NO:30), and I53-50A.1PosT1 (SEQ ID NO:31), and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of I53-50B (SEQ ID NO:8), I53-50B.1 (SEQ ID NO:32), I53-50B.1NegT2 (SEQ ID NO:33), and I53-50B.4PosT1 (SEQ ID NO:34).

In another specific embodiment, the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of I32-28A (SEQ ID NO:21) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of I32-28B (SEQ ID NO:22).

The nanostructures of the invention display multiple copies (i.e.: 2, 3, or more) of one or more paramyxovirus and/or pneumovirus F proteins, or antigenic fragments thereof, on an exterior of the nanostructure. Exemplary paramyxovirus and/or pneumovirus include, but are not limited to, respiratory syncytial virus (RSV) and Human metapneumovirus (hMPV). (C. L. Afonso et al., Taxonomy of the order Mononegavirales: update 2016. Arch. Virol. 161, 2351-2360 (2016)).

As used herein, "on an exterior of the nanostructure" means that an antigenic portion of the one or more paramyxovirus and/or pneumovirus F proteins, or antigenic fragments thereof, must be accessible for binding by B cell receptors, antibodies, or antibody fragments and not buried within the nanostructure.

The one or more paramyxovirus and/or pneumovirus F proteins, or antigenic fragments thereof, may comprise any suitable native F proteins, post-fusion, or pre-fusion (preF) antigens, or mutants thereof capable of inducing an immune response that will generate antibodies that bind to paramyxovirus and/or pneumovirus F proteins. A nanostructure may display more than one F protein; thus, in some embodiments the one or more paramyxovirus and/or pneumovirus F proteins, or antigenic fragments thereof comprise 1, 2, 3, 4, or more F proteins or antigenic fragments thereof. In one embodiment, the one or more paramyxovirus and/or pneumovirus F proteins, or antigenic fragments thereof may be as defined in patent publication number US 2016/0046675 A1. In some embodiments, the one or more paramyxovirus and/or pneumovirus F proteins, or antigenic fragments thereof, are selected from the group consisting of SEQ ID NOS: 1-350, 370-382, 389-693, 698-1026, 1429-1442, 1456-1468, and 1474-1478 as disclosed in US published patent application 2016/0046675. In other embodiments, the one or more paramyxovirus and/or pneumovirus F proteins, or antigenic fragments thereof may be as defined in WO2012158613, US 20160102123, US20140141037, WO2014079842, WO2014160463, US20140271699, EP2970393, WO2014174018, US20140271699, US20160176932, US20160122398, WO2017040387, WO2017109629, WO2017172890, WO2017207477, Krarup et al. (2015) Nature Communications 6:8143, and WO2017207480.

In a specific embodiment, the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to the amino acid sequence of DS-Cav1 shown below (residues in parentheses are optional; note that the N-terminal residues in parentheses are cleaved from the protein during secretion—the mature N terminus begins with QNITEEF . . . (SEQ ID NO:52)). DS-Cav1 comprises a prefusion-stabilized form of the fusion (F) glycoprotein, which elicits improved protective responses against respiratory syncytial virus (RSV) in mice and macaques compared to postfusion RSV F (McLellan et al. (2013) *Science* 342:592-8).

```
DS-Cav1 (SEQ ID NO: 53):
(MELLILKANAITTILTAVTFCFASG)QNITEEFYQSTCSAVSKGYLSA

LRTGWYTSVITIELSNIKENKCNGTDAKVKLIKQELDKYKNAVTELQLL

MQSTPATNNRARRELPRFMNYTLNNAKKTNVTLSKKRKRRFLGFLLGVG

SAIASGVAVCKVLHLEGEVNKIKSALLSTNKAVVSLSNGVSVLTFKVLD

LKNYIDKQLLPILNKQSCSISNIETVIEFQQKNNRLLEITREFSVNAGV
```

```
-continued
TTPVSTYMLTNSELLSLINDMPITNDQKKLMSNNVQIVRQQSYSIMCII

KEEVLAYVVQLPLYGVIDTPCWKLHTSPLCTINTKEGSNICLTRTDRGW

YCDNAGSVSFFPQAETCKVQSNRVFCDTMNSLTLPSEVNLCNVDIFNPK

YDCKIMTSKTDVSSSVITSLGAIVSCYGKTKCTASNKNRGIIKTFSNGC

DYVSNKGVDTVSVGNTLYYVNKQEGKSLYVKGEPIINFYDPLVFPSDEF

DASISQVNEKINQSLAFIR(KSDELL)
```

In other embodiments, the F protein may comprise a polypeptide having at least 75%, 80%, 85%, 90%, 91%, 92%, 93%, 94%, 95%, 96%, 97%, 98%, 99%, or 100% identity along its full length to a polypeptide selected from:

```
RSV F
sc9-10 DS-Cav1 A149C Y458C
                                      (SEQ ID NO: 61)
(MELLILKANAITTILTAVTFCFASG)QNITEEFYQSTCSAVSKGYLSA

LRTGWYTSVITIELSNIKENKCNGTDAKVKLIKQELDKYKNAVTELQLL

MQSTPATGSGSAICSGVAVCKVLHLEGEVNKIKSALLSTNKAVVSLSNG

VSVLTFKVLDLKNYIDKQLLPILNKQSCSISNIETVIEFQQKNNRLLEI

TREFSVNAGVTTPVSTYMLTNSELLSLINDMPITNDQKKLMSNNVQIVR

QQSYSIMCIIKEEVLAYVVQLPLYGVIDTPCWKLHTSPLCTTNTKEGSN

ICLTRTDRGWYCDNAGSVSFFPQAETCKVQSNRVFCDTMNSRTLPSEVN

LCNVDIFNPKYDCKIMTSKTDVSSSVITSLGAIVSCYGKTKCTASNKNR

GIIKTFSNGCDYVSNKGVDTVSVGNTLYCVNKQEGKSLYVKGEPIINFY

DPLVFPSDEFDASISQVNEKINQSLAFIR(KSDELL)

sc9-10 DS-Cav1 A149C Y458C S46G K465Q S215P E92D
                                      (SEQ ID NO: 62)
(MELLILKANAITTILTAVTFCFASG)QNITEEFYQSTCSAVSKGYLGA

LRTGWYTSVITIELSNIKENKCNGTDAKVKLIKQELDKYKNAVTDLQLL

MQSTPATGSGSAICSGVAVCKVLHLEGEVNKIKSALLSTNKAVVSLSNG

VSVLTFKVLDLKNYIDKQLLPILNKQSCSIPNIETVIEFQQKNNRLLEI

TREFSVNAGVTTPVSTYMLTNSELLSLINDMPITNDQKKLMSNNVQIVR

QQSYSIMCIIKEEVLAYVVQLPLYGVIDTPCWKLHTSPLCTTNTKEGSN

ICLTRTDRGWYCDNAGSVSFFPQAETCKVQSNRVFCDTMNSRTLPSEVN

LCNVDIFNPKYDCKIMTSKTDVSSSVITSLGAIVSCYGKTKCTASNKNR

GIIKTFSNGCDYVSNKGVDTVSVGNTLYCVNKQEGQSLYVKGEPIINFY

DPLVFPSDEFDASISQVNEKINQSLAFIR(KSDELL)
```

SEQ ID NO:61-62 represent second-generation stabilized DS-Cav1 immunogens; mutations relative to DS-Cav1 are noted and it should be noted that the present disclosure contemplates the use of DS-Cav1 mutants that differ by a single one of the noted amino acid substitutions in SEQ ID NO:61 or 62 above, or two or more of the amino acid substitutions noted. In other embodiments, the F protein may comprise one or more of the following, each of which may additionally include 1, 2, or more of the noted amino acid substitutions in SEQ ID NO:61 or 62 above:

RSV F SC-DM (N67I, S215P)
(SEQ ID NO: 63)
(MELLILKANAITTILTAVTFCFASG)QNITEEFYQSTCSAVSKGYLSALRTGWYTSVITIELSN
IKKIKCNGTDAKIKLIKQELDKYKNAVTELQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSIP
NIETVIEFQQKNNRLLEITREFSVNAGVTTPVSTYMLTNSELLSLINDMPITNDQKKLMSNNVQI
VRQQSYSIMSIIKEEVLAYVVQLPLYGVIDTPCWKLHTSPLCTTNTKEGSNICLTRTDRGWYCDN
AGSVSFFPQAETCKVQSNRVFCDTMNSLTLPSEVNLCNVDIFNPKYDCKIMTSKTDVSSSVITSL
GAIVSCYGKTKCTASNKNRGIIKTFSNGCDYVSNKGVDTVSVGNTLYYVNKQEGKSLYVKGEPII
NFYDPLVFPSDEFDASISQVNEKINQSLAFIR(KSDELLSAIGGYIPEAPRDGQAYVRKDGEWVL
LSTFL)

SC-TM (N67I, S215P, and E487Q)
(SEQ ID NO: 64)
(MELLILKANAITTILTAVTFCFASG)QNITEEFYQSTCSAVSKGYLSALRTGWYTSVITIELSN
IKKIKCNGTDAKIKLIKQELDKYKNAVTELQLLMQSTPATNNQARGSGSGRSLGFLLGVGSAIAS
GVAVSKVLHLEGEVNKIKSALLSTNKAVVSLSNGVSVLTSKVLDLKNYIDKQLLPIVNKQSCSIP
NIETVIEFQQKNNRLLEITREFSVNAGVTTPVSTYMLTNSELLSLINDMPITNDQKKLMSNNVQI
VRQQSYSIMSIIKEEVLAYVVQLPLYGVIDTPCWKLHTSPLCTTNTKEGSNICLTRTDRGWYCDN
AGSVSFFPQAETCKVQSNRVFCDTMNSLTLPSEVNLCNVDIFNPKYDCKIMTSKTDVSSSVITSL
GAIVSCYGKTKCTASNKNRGIIKTFSNGCDYVSNKGVDTVSVGNTLYYVNKQEGKSLYVKGEPII
NFYDPLVFPSDQFDASISQVNEKINQSLAFIR(KSDELLSAIGGYIPEAPRDGQAYVRKDGEWVL
LSTFL)

HMPV F protein, strain CAN97-83 (A2)
(SEQ ID NO: 65)
(MSWKVVIIFSLLITPQHG)LKESYLEESCSIITEGYLSVLRTGWYTNVFTLEVGDVENLICSDG
PSLIKTELDLTKSALRELKTVSADQLAREEQIENPRQSRFVLGAIALGVATAAAVTAGVAIAKTI
RLESEVTAIKNALKTTNEAVSTLGNGVRVLATAVRELKDFVSKNLTRAINKNKCDIDDLKMAVSF
SQFNRRFLNVVRQFSDNAGITPAISLDLMTDAELARAVSNMPTSAGQIKLMLENRAMVRRKGFGI
LIGVYGSSVIYMVQLPIFGVIDTPCWIVKAAPSCSGKKGNYACLLREDQGWYCQNAGSTVYYPNE
KDCETRGDHVFCDTAAGINVAEQSKECNINISTTNYPCKVSTGRHPISMVALSPLGALVACYKGV
SCSIGSNRVGIIKQLNKGCSYITNQDADTVTIDNTVYQLSKVEGEQHVIKGRPVSSSFDPIKFPE
DQFNVALDQVFENIENSQALVDQSNRILSSAEKGNIG HMPVF with A113C, A339C, T160F, I177L
(SEQ ID NO: 66)
(MSWKVVIIFSLLITPQHG)LKESYLEESCSIITEGYLSVLRTGWYTNVFTLEVGDVENLICSDG
PSLIKTELDLTKSALRELKTVSADQLAREEQIENPRQSRFVLGAIALGVCTAAAVTAGVAIAKTI
RLESEVTAIKNALKTTNEAVSTLGNGVRVLAFAVRELKDFVSKNLTRALNKNKCDIDDLKMAVSF
SQFNRRFLNVVRQFSDNAGITPAISLDLMTDAELARAVSNMPTSAGQIKLMLENRAMVRRKGFGI
LIGVYGSSVIYMVQLPIFGVIDTPCWIVKAAPSCSGKKGNYACLLREDQGWYCQNAGSTVYYPNE
KDCETRGDHVFCDTACGINVAEQSKECNINISTTNYPCKVSTGRHPISMVALSPLGALVACYKGV
SCSIGSNRVGIIKQLNKGCSYITNQDADTVTIDNTVYQLSKVEGEQHVIKGRPVSSSFDPIKFPE
DQFNVALDQVFENIENSQALVDQSNRILSSAEKGNIG HMPV F with A113C, A120C, A339C, T160F, I177L, and Q426C
(SEQ ID NO: 67)
(MSWKVVIIFSLLITPQHG)LKESYLEESCSTITEGYLSVLRTGWYTNVFTLEVGDVENLICSDG
PSLIKTELDLTKSALRELKTVSADQLAREEQIENPRQSRFVLGAIALGVCTAAAVTCGVAIAKTI -continued

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNIG

HMPV F_>AAK62968.2 fusion protein [Human metapneumovirus]
(SEQ ID NO: 101)
(MSWKVVIIFSLLITPQHG)LKESYLEESCSTITEGYLSVLRTGWYTNVFTLEVGDVENLICADG

PSLIKTELDLIKSALRELRIVSADQLAREEQIENPRQSRFVLGAIALGVATAAAVTAGVAIAKTI

RLESEVTAIKNALKKTNEAVSTLGNGVRVLATAVRELKDFVSKNLTRAINKNKCDIADLKMAVSF

SQFNRRFLNVVRQFSDNAGITPAISLDLMTDAELARAVSNMPTSAGQIKLMLENRAMVRRKGFGF

LIGVYGSSVIYMVQLPIFGVIDTPCWIVKAAPSCSGKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNIG

115-BV (A185P)
(SEQ ID NO: 68)
(MSWKVVIIFSLLITPQHG)LKESYLEESCSTITEGYLSVLRTGWYTNVFTLEVGDVENLICADG

PSLIKTELDLIKSALRELRIVSADQLAREEQIENPRRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNT(SGRENLYFQGGGGSGYIPEAPRDGQAYV

RKDGEWVLLSTFLGGIEGRHHHHHH)

In other embodiments, the one or more paramyxovirus and/or pneumovirus F proteins, or antigenic fragments thereof, may comprise a polypeptide having at least 75%, 80%, 85%, 90%, 91%, 92%, 93%, 94%, 95%, 96%, 97%, 98%, 99%, or 100% identity along its full length to an RSV F protein or mutant thereof selected from the group consisting of SEQ ID NO:53 and 61-64, wherein the polypeptide includes one or more of the following residues: 67I, 149C, 458C, 46G, 465Q, 215P, 92D, and 487Q.

In other embodiments, the one or more paramyxovirus and/or pneumovirus F proteins, or antigenic fragments thereof, may comprise a polypeptide having at least 75%, 80%, 85%, 90%, 91%, 92%, 93%, 94%, 95%, 96%, 97%, 98%, 99%, or 100% identity along its full length to an MPV F protein or mutant thereof selected from the group consisting of SEQ ID NO:65-68 and 101, wherein the polypeptide includes one or more of the following residues: 113C, 120C, 339C, 160F, 177L, 185P, and 426C.

Linker Between F Proteins and Trimeric Assembly Domains and Geometric Requirements In the nanostructures of the invention, the F protein and the trimeric assembly domain may be genetically fused such that they are both present in a single polypeptide. Preferably, the linkage between the F protein and the trimeric assembly domain allows the F protein, or antigenic fragment thereof, to be displayed on the exterior of the nanostructures of the invention. As such, the point of connection to the trimeric assembly domain should be on the exterior of the nanostructure formed by the trimeric assembly domain and the second assembly domain in the absence of any F protein. As will be understood by those of skill in the art, a wide variety of polypeptide sequences can be used to link the paramyxovirus and/or pneumovirus F proteins, or antigenic fragments thereof and the trimeric assembly domain. These polypeptide sequences are referred to as linkers. Any suitable linker can be used; there is no amino acid sequence requirement to serve as an appropriate linker. There is no requirement that the linker impose a rigid relative orientation of the F protein or antigenic fragment thereof to the trimeric assembly domain beyond enabling the F protein or antigenic fragment thereof to be displayed on the exterior of the nanostructures of the invention. In some embodiments, the linker includes additional trimerization domains (e.g., the foldon domain of T4 fibritin) that assist in stabilizing the trimeric form of the F protein.

T4 Fibritin Foldon Domain (Optional in the Linker Region)
(SEQ ID NO:54)
GYIPEAPRDGQAYVRKDGEWVLLSTFL In other embodiments, the linker may comprise a Gly-Ser linker (i.e.: a linker consisting of glycine and serine residues) of any suitable length. In various embodiments, the Gly-Ser linker may be 3, 4, 5, 6, 7, 8, 9, 10, 11, 12, 13, 14, 15, 16, 17, 18, 19, 20, or more amino acids in length. In various embodiments, the Gly-Ser linker may comprise or consist of the amino acid sequence of GSGGSGSGSGGSGSG (SEQ ID NO:55), GGSGGSGS (SEQ ID NO:56) or GSGGSGSG (SEQ ID NO:57).

In further embodiments the linker may comprise a helical extension domain that may serve to extend the N-terminal helix of the first polypeptide, when expressed as a fusion polypeptide with the one or more paramyxovirus and/or pneumovirus F proteins, or antigenic fragments thereof, so that it is located at the exterior of the nanostructure surface. The helical extension may be present in combination with the other linker components described herein, or may be absent. The helical extension may be of any suitable length (i.e.: 7, 8, 9, 10, 11, 12, or more amino acids) and comprise any suitable primary amino acid sequence. In one embodiment, the helical extension may comprise or consist of the amino acid sequence EKAAKAEEAAR (SEQ ID NO:58).

Thus, in various non-limiting embodiments in which the F protein is present as a fusion protein with the first polypeptide and a linker is used, the F protein-linker sequence may comprise the following (exemplified by DS-Cav1 as the F protein in these non-limiting embodiments). Residues in parentheses are optional and the amino acid sequence MELLILKANAITTILTAVTFCFASG (SEQ ID NO:59) represents the N-terminal DS-Cav1 signal peptide that is cleaved during processing:

```
DS-Cav1-foldon (SEQ ID NO: 60):
(MELLILKANAITTILTAVTFCFASG)QNITEEFYQSTCSAVSKGYLSA

LRTGWYTSVITIELSNIKENKCNGTDAKVKLIKQELDKYKNAVTELQLL

MQSTPATNNRARRELPRFMNYTLNNAKKTNVTLSKKRKRRFLGFLLGVG

SAIASGVAVCKVLHLEGEVNKIKSALLSTNKAVVSLSNGVSVLTFKVLD

LKNYIDKQLLPILNKQSCSISNIETVIEFQQKNNRLLEITREFSVNAGV

TTPVSTYMLTNSELLSLINDMPITNDQKKLMSNNVQIVRQQSYSIMCII

KEEVLAYVVQLPLYGVIDTPCWKLHTSPLCTINTKEGSNICLTRTDRGW

YCDNAGSVSFFPQAETCKVQSNRVFCDTMNSLTLPSEVNLCNVDIFNPK

YDCKIMTSKTDVSSSVITSLGAIVSCYGKTKCTASNKNRGIIKTFSNGC

DYVSNKGVDTVSVGNTLYYVNKQEGKSLYVKGEPIINFYDPLVFPSDEF

DASISQVNEKINQSLAFIRKSDELLGYIPEAPRDGQAYVRKDGEWVLLS

TFL
```

In various further embodiments, the first polypeptides comprise or consist of fusion polypeptides of first polypeptides fused to an F protein, where the fusion protein has a sequence selected from the following (optional residues in parentheses):

```
DS-Cav1-foldon-T33-31A
                                                    (SEQ ID NO: 69)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGYIPE

APRDGQAYVRKDGEWVLLSTFLGGSMEEVVLITVPSALVAVKIAHALVEERLAACVNIVPGLTSI

YREEGSVVSDHELLLLVKITTDAFPKLKERVKELHPYEVPEIVALPIAEGNREYLDWLRENTG

DS-Cav1-T33-31A
                                                    (SEQ ID NO: 70)
(MELLILKANVIATILTAVTFCFASS)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGGSME

EVVLITVPSALVAVKIAHALVEERLAACVNIVPGLTSIYREEGSVVSDHELLLLVKITTDAFPKL

KERVKELHPYEVPEIVALPIAEGNREYLDWLRENTG
```

DS-Cav1-foldon-T33-15B
(SEQ ID NO: 71)
(MELLILKANVIATILTAVTFCFASS)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRKSDELLGYIPE
APRDGQAYVRKDGEWVLLSTFLGGSMVRGIRGAITVNSDTPTSIIIATILLLEKMLEANGIQSYE
ELAAVIFTVTEDLTSAFPAEAARQIGMHRVPLLSAREVPVPGSLPRVIRVLALWNTDTPQDRVRH
VYLSEAVRLRPDLESAQ DS-Cav1-T33-15B
(SEQ ID NO: 72)
(MELLILKANVIATILTAVTFCFASS)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRKSDELLGGSMV
RGIRGAITVNSDTPTSIIIATILLLEKMLEANGIQSYEELAAVIFTVTEDLTSAFPAEAARQIGM
HRVPLLSAREVPVPGSLPRVIRVLALWNTDTPQDRVRHVYLSEAVRLRPDLESAQ DS-Cav1-foldon-I53-50A
(SEQ ID NO: 73)
(MELLILKANAITTILTAVTFCFASG)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL
SLINDMPITNDQKKLMSNNVQIVRQQSYSIMCIIKEEVLAYVVQLPLYGVIDTPCWKLHTSPLCT
INTKEGSNICLTRTDRGWYCDNAGSVSFFPQAETCKVQSNRVFCDTMNSLTLPSEVNLCNVDIFN
PKYDCKIMTSKTDVSSSVITSLGAIVSCYGKTKCTASNKNRGIIKTFSNGCDYVSNKGVDTVSVG
NTLYYVNKQEGKSLYVKGEPIINFYDPLVFPSDEFDASISQVNEKINQSLAFIRGYIPEAPRDGQ
AYVRKDGEWVLLSTFLGSGSHHHHHHHHGGSGGSGSEKAAKAEEAARKMEELFKKHKIVAVLRAN
SVEEAIEKAVAVFAGGVHLIEITFTVPDADTVIKALSVLKEKGAIIGAGTVTSVEQCRKAVESGA
EFIVSPHLDEEISQFCKEKGVFYMPGVMTPTELVKAMKLGHTILKLFPGEVVGPQFVKAMKGPFP
NVKFVPTGGVNLDNVCEWFKAGVLAVGVGSALVKGTPDEVREKAKAFVEKIRGCTE DS-Cav1-I53-50A
(SEQ ID NO: 74)
(MELLILKANVIATILTAVTFCFASS)QNITEEFYQSTCSAVSKGYLSALRTGWYTSVITIELSN
IKENKCNGTDAKVKLIKQELDKYKNAVTELQLLMQSTPATNNRARRELPRFMNYTLNNAKKTNVT
LSKKRKRRFLGFLLGVGSAIASGVAVCKVLHLEGEVNKIKSALLSTNKAVVSLSNGVSVLTFKVL
DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGGSGGSGSEKA

AKAEEAARKMEELFKKHKIVAVLRANSVEEAIEKAVAVFAGGVHLIEITFTVPDADTVIKALSVL

KEKGAIIGAGTVTSVEQCRKAVESGAEFIVSPHLDEEISQFCKEKGVFYMPGVMTPTELVKAMKL

GHTILKLFPGEVVGPQFVKAMKGPFPNVKFVPTGGVNLDNVCEWFKAGVLAVGVGSALVKGTPDE

VREKAKAFVEKIRGCTE

DS-Cav1-I32-28A
(SEQ ID NO: 75)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRKSDELLGGSGG

SGSDDARIAAIGDVDELNSQIGVLLAEPLPDDVRAALSAIQHDLFDLGGELCIPGHAAITEDHLL

RLALWLVHYNGQLPPLEEFILPGGARGAALAHVCRTVCRRAERSIKALGASEPLNIAPAAYVNLL

SDLLFVLARVLNRAAGGADVLWDRTRAH

DS-Cav1-8GS-HelExt-I53-50A (F10)
(SEQ ID NO: 76)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGSGGSGSEKA

AKAEEAARKMEELFKKHKIVAVLRANSVEEAIEKAVAVFAGGVHLIEITFTVPDADTVIKALSVL

KEKGAIIGAGTVTSVEQCRKAVESGAEFIVSPHLDEEISQFCKEKGVFYMPGVMTPTELVKAMKL

GHTILKLFPGEVVGPQFVKAMKGPFPNVKFVPTGGVNLDNVCEWFKAGVLAVGVGSALVKGTPDE

VREKAKAFVEKIRGCTE

DS-Cav1-foldon-15GS-HelExt-I53-50A (F14)
(SEQ ID NO: 77)
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

-continued

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGYIPEAPRDGQ

AYVRKDGEWVLLSTFLGSGGSGSGGSGSGEKAAKAEEAARKMEELFKKHKIVAVLRANSVEEA

IEKAVAVFAGGVHLIEITFTVPDADTVIKALSVLKEKGAIIGAGTVTSVEQCRKAVESGAEFIVS

PHLDEEISQFCKEKGVFYMPGVMTPTELVKAMKLGHTILKLFPGEVVGPQFVKAMKGPFPNVKFV

PTGGVNLDNVCEWFKAGVLAVGVGSALVKGTPDEVREKAKAFVEKIRGCTE

HMPV_F_wt_CAN97-83 strain-I53-50A (SEQ ID NO: 78)

(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVATAAAVTAGVAIAKTI

RLESEVTAIKNALKTTNEAVSTLGNGVRVLATAVRELKDFVSKNLTRAINKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGFIIVIILIAVLGSSMILVSIFIIIKKTK

KPTGAPPELSGVTNNGFIPHSGSGSHHHHHHHHGSGGSGSEKAAKAEEAARKMEELFKKHKIVA

VLRANSVEEAIEKAVAVFAGGVHLIEITFTVPDADTVIKALSVLKEKGAIIGAGTVTSVEQCRKA

VESGAEFIVSPHLDEEISQFCKEKGVFYMPGVMTPTELVKAMKLGHTILKLFPGEVVGPQFVKAM

KGPFPNVKFVPTGGVNLDNVCEWFKAGVLAVGVGSALVKGTPDEVREKAKAFVEKIRGCTE

HMPV_F_A113C_A339C_T160F_I177L-I53-50A (SEQ ID NO: 79)

(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGGSGSHHHHHHHHGSGGSGSEKAAKAEE

AARKMEELFKKHKIVAVLRANSVEEAIEKAVAVFAGGVHLIEITFTVPDADTVIKALSVLKEKGA

IIGAGTVTSVEQCRKAVESGAEFIVSPHLDEEISQFCKEKGVFYMPGVMTPTELVKAMKLGHTIL

KLFPGEVVGPQFVKAMKGPFPNVKFVPTGGVNLDNVCEWFKAGVLAVGVGSALVKGTPDEVREKA

KAFVEKIRGCTE

HMPV_F_A113C_A339C_T160F_I177L_A120C, Q426C mutations-I53-50A (SEQ ID NO: 80)

(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGSGSHHHHHHHHGSGGSGSEKAAKAEE

```
AARKMEELFKKHKIVAVLRANSVEEAIEKAVAVFAGGVHLIEITFTVPDADTVIKALSVLKEKGA

IIGAGTVTSVEQCRKAVESGAEFIVSPHLDEEISQFCKEKGVFYMPGVMTPTELVKAMKLGHTIL

KLFPGEVVGPQFVKAMKGPFPNVKFVPTGGVNLDNVCEWFKAGVLAVGVGSALVKGTPDEVREKA

KAFVEKIRGCTE
``` sc-DS2-I53-50A
(SEQ ID NO: 81)
```
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATGSGSCIASGVAVCKVLHLEGEVNKI

KSALLSTNKAVVSLSNGVSVLTFKVLDLKNYIDKQLLPILNKQSCSISNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTTNTKEGSNICLTRTDRGWYCDNAGSVSFFPQAETCKVQS

NRVFCDTMNSLTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGKSLYVKGEPIINFYDPLVFPSDEFDASI

SQVNEKINQSLAFIRGSGSHHHHHHHGGSGGSGSEKAAKAEEAARKMEELFKKHKIVAVLRANS

VEEAIEKAVAVFAGGVHLIEITFTVPDADTVIKALSVLKEKGAIIGAGTVTSVEQCRKAVESGAE

FIVSPHLDEEISQFCKEKGVFYMPGVMTPTELVKAMKLGHTILKLFPGEVVGPQFVKAMKGPFPN

VKFVPTGGVNLDNVCEWFKAGVLAVGVGSALVKGTPDEVREKAKAFVEKIRGCTE
``` tc-DS2-I53-50A
(SEQ ID NO: 82)
```
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSCIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYCVNKQEGKSLYVKGEPIINFYDPLVFPSDEFDASISQVNEKINQSLAFIRGSGSHHHHHHH

HGGSGGSGSEKAAKAEEAARKMEELFKKHKIVAVLRANSVEEAIEKAVAVFAGGVHLISITFTVP

DADTVIKALSVLKEKGAIIGAGTVTSVEQCRKAVESGAEFIVSPHLDEEISQFCKEKGVFYMPGV

MTPTELVKAMKLGHTILKLFPGEVVGPQFVKAMKGPFPNVKFVPTGGVNLDNVCEWFKAGVLAVG

VGSALVKGTPDEVREKAKAFVEKIRGCTE
```

DS-Cav1-12GS-HelExt-I53-50A (F11)
(SEQ ID NO: 83)
```
(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGSGGSGSGSGG

SEKAAKAEEAARKMEELFKKHKIVAVLRANSVEEAIEKAVAVFAGGVHLIEliFTVPDADTVIKA

LSVLKEKGAIIGAGTVTSVEQCRKAVESGAEFIVSPHLDEEISQFCKEKGVFYMPGVMTPTELVK
```

-continued

AMKLGHTILKLFPGEVVGPQFVKAMKGPFPNVKFVPTGGVNLDNVCEWFKAGVLAVGVGSALVKG

TPDEVREKAKAFVEKIRGCTE

DS-Cav1-16GS-HelExt-I53-50A (F12)
(SEQ ID NO: 84)

(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGSGGGSGSGSGG

SGSGGEKAAKAEEAARKMEELFKKHKIVAVLRANSVEEAIEKAVAVFAGGVHLIEliFTVPDADT

VIKALSVLKEKGAIIGAGTVTSVEQCRKAVESGAEFIVSPHLDEEISQFCKEKGVFYMPGVMTPT

ELVKAMKLGHTILKLFPGEVVGPQFVKAMKGPFPNVKFVPTGGVNLDNVCEWFKAGVLAVGVGSA

LVKGTPDEVREKAKAFVEKIRGCTE

DS-Cav1-foldon-10GS-HelExt-I53-50A (F13
(SEQ ID NO: 85)

(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGYIPEAPRDGQ

AYVRKDGEWVLLSTFLGSGGSGSGSGEKAAKAEEAARKMEELFKKHKIVAVLRANSVEEAIEKAV

AVFAGGVHLIEITFTVPDADTVIKALSVLKEKGAIIGAGTVTSVEQCRKAVESGAEFIVSPHLDE

EISQFCKEKGVFYMPGVMTPTELVKAMKLGHTILKLFPGEVVGPQFVKAMKGPFPNVKFVPTGGV

NLDNVCEWFKAGVLAVGVGSALVKGTPDEVREKAKAFVEKIRGCTE

DS-Cav1-foldon-20GS-HelExt-I53-50A (F15)
(SEQ ID NO: 86)

(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATNNRARRELPRFMNYTLNNAKKTNVT

LSKKRKRRFLGFLLGVGSAIASGVAVCKVLHLEGEVNKIKSALLSTNKAVVSLSNGVSVLTFKVL

DLKNYIDKQLLPILNKQSCSISNIETVIEFQQKNNRLLEITREFSVNAGVTTPVSTYMLTNSELL

SLINDMPITNDQKKLMSNNVQIVRQQSYSIMCIIKEEVLAYVVQLPLYGVIDTPCWKLHTSPLCT

INTKEGSNICLTRTDRGWYCDNAGSVSFFPQAETCKVQSNRVFCDTMNSLTLPSEVNLCNVDIFN

PKYDCKIMTSKTDVSSSVITSLGAIVSCYGKTKCTASNKNRGIIKTFSNGCDYVSNKGVDTVSVG

NTLYYVNKQEGKSLYVKGEPIINFYDPLVFPSDEFDASISQVNEKINQSLAFIRGYIPEAPRDGQ

AYVRKDGEWVLLSTFLGSGGSGSGSGGSGSGGSSGSEKAAKAEEAARKMEELFKKHKIVAVLRAN

SVEEAIEKAVAVFAGGVHLIEITFTVPDADTVIKALSVLKEKGAIIGAGTVTSVEQCRKAVESGA

EFIVSPHLDEEISQFCKEKGVFYMPGVMTPTELVKAMKLGHTILKLFPGEVVGPQFVKAMKGPFP

NVKFVPTGGVNLDNVCEWFKAGVLAVGVGSALVKGTPDEVREKAKAFVEKIRGCTE sc9-10 DS-Cav1 A149C Y458C-foldon-I53-50A embodiment (SEQ ID NO: 87)

(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATGSGSAICSGVAVCKVLHLEGEVNKI

KSALLSTNKAVVSLSNGVSVLTFKVLDLKNYIDKQLLPILNKQSCSISNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTINTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGKSLYVKGEPIINFYDPLVFPSDEFDASI

SQVNEKINQSLAFIR(KSDELL)GYIPEAPRDGQAYVRKDGEWVLLSTFLGSGSHHHHHHHHGGS

GGSGSEKAAKAEEAARKMEELFKKHKIVAVLRANSVEEAIEKAVAVFAGGVHLIEITFTVPDADT

VIKALSVLKEKGAIIGAGTVTSVEQCRKAVESGAEFIVSPHLDEEISQFCKEKGVFYMPGVMTPT

ELVKAMKLGHTILKLFPGEVVGPQFVKAMKGPFPNVKFVPTGGVNLDNVCEWFKAGVLAVGVGSA

LVKGTPDEVREKAKAFVEKIRGCTE sc9-10 DS-Cav1 A149C Y458C-I53-50A - F10 embodiment (SEQ ID NO: 88)

(MELLILKANAITTILTAVTFCFASG)QNITEEFYQSTCSAVSKGYLSALRTGWYTSVITIELSN

IKENKCNGTDAKVKLIKQELDKYKNAVTELQLLMQSTPATGSGSAICSGVAVCKVLHLEGEVNKI

KSALLSTNKAVVSLSNGVSVLTFKVLDLKNYIDKQLLPILNKQSCSISNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTINTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGKSLYVKGEPIINFYDPLVFPSDEFDASI

SQVNEKINQSLAFIR(KSDELL)GSGGSGSGEKAAKAEEAARKMEELFKKHKIVAVLRANSVEEA

IEKAVAVFAGGVHLIEITFTVPDADTVIKALSVLKEKGAIIGAGTVTSVEQCRKAVESGAEFIVS

PHLDEEISQFCKEKGVFYMPGVMTPTELVKAMKLGHTILKLFPGEVVGPQFVKAMKGPFPNVKFV

PTGGVNLDNVCEWFKAGVLAVGVGSALVKGTPDEVREKAKAFVEKIRGCTE sc9-10 DS-Cav1 A149C Y458C S46G K465Q S215P E92D-foldon-I53-50A embodiment (SEQ ID NO: 89)

(MELLILKANAITTILTAVTFCFASG)QNITEEFYQSTCSAVSKGYLGALRTGWYTSVITIELSN

IKENKCNGTDAKVKLIKQELDKYKNAVTDLQLLMQSTPATGSGSAICSGVAVCKVLHLEGEVNKI

KSALLSTNKAVVSLSNGVSVLTFKVLDLKNYIDKQLLPILNKQSCSIPNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTTNTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGQSLYVKGEPIINFYDPLVFPSDEFDASI

SQVNEKINQSLAFIR(KSDELL)GYIPEAPRDGQAYVRKDGEWVLLSTFLGSGSHHHHHHHHGGS

GGSGSEKAAKAEEAARKMEELFKKHKIVAVLRANSVEEAIEKAVAVFAGGVHLIEliFTVPDADT

VIKALSVLKEKGAIIGAGTVTSVEQCRKAVESGAEFIVSPHLDEEISQFCKEKGVFYMPGVMTPT

ELVKAMKLGHTILKLFPGEVVGPQFVKAMKGPFPNVKFVPTGGVNLDNVCEWFKAGVLAVGVGSA

LVKGTPDEVREKAKAFVEKIRGCTE sc9-10 DS-Cav1 A149C Y458C S46G K465Q S215P E92D-I53-50A - F10
embodiment (SEQ ID NO: 90)

(MELLILKANAITTILTAVTFCFASG)QNITEEFYQSTCSAVSKGYLGALRTGWYTSVITIELSN

IKENKCNGTDAKVKLIKQELDKYKNAVTDLQLLMQSTPATGSGSAICSGVAVCKVLHLEGEVNKI

KSALLSTNKAVVSLSNGVSVLTFKVLDLKNYIDKQLLPILNKQSCSIPNIETVIEFQQKNNRLLE

ITREFSVNAGVTTPVSTYMLINSELLSLINDMPITNDQKKLMSNNVQIVRQQSYSIMCIIKEEVL

AYVVQLPLYGVIDTPCWKLHTSPLCTTNTKEGSNICLTRTDRGWYCDNAGSVSFFPQAETCKVQS

NRVFCDTMNSRTLPSEVNLCNVDIFNPKYDCKIMTSKTDVSSSVITSLGAIVSCYGKTKCTASNK

NRGIIKTFSNGCDYVSNKGVDTVSVGNTLYCVNKQEGQSLYVKGEPIINFYDPLVFPSDEFDASI

SQVNEKINQSLAFIR(KSDELL)GSGGGSGSGEKAAKAEEAARKMEELFKKHKIVAVLRANSVEEA

IEKAVAVFAGGVHLIEITFTVPDADTVIKALSVLKEKGAIIGAGTVTSVEQCRKAVESGAEFIVS

PHLDEEISQFCKEKGVFYMPGVMTPTELVKAMKLGHTILKLFPGEVVGPQFVKAMKGPFPNVKFV

PTGGVNLDNVCEWFKAGVLAVGVGSALVKGTPDEVREKAKAFVEKIRGCTE

SC-DM (N67I, S215P) - foldon-I53-50A embodiment (SEQ ID NO: 91)

(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDEFDASISQVNEKINQSLAFIR(KSDELL)GYIPEAPRDGQAYVRKDGEWVLLST

FLGSGSHHHHHHGGSGGSGSEKAAKAEEAARKMEELFKKHKIVAVLRANSVEEAIEKAVAVFA

GGVHLIEITFTVPDADTVIKALSVLKEKGAIIGAGTVTSVEQCRKAVESGAEFIVSPHLDEEISQ

FCKEKGVFYMPGVMTPTELVKAMKLGHTILKLFPGEVVGPQFVKAMKGPFPNVKFVPTGGVNLDN

VCEWFKAGVLAVGVGSALVKGTPDEVREKAKAFVEKIRGCTE

SC-DM (N67I, S215P)-I53-50A - F10 embodiment (SEQ ID NO: 92)

(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDEFDASISQVNEKINQSLAFIR(KSDELL)GSGGSGSGEKAAKAEEAARKMEELF

KKHKIVAVLRANSVEEAIEKAVAVFAGGVHLIEITFTVPDADTVIKALSVLKEKGAIIGAGTVTS

VEQCRKAVESGAEFIVSPHLDEEISQFCKEKGVFYMPGVMTPTELVKAMKLGHTILKLFPGEVVG

PQFVKAMKGPFPNVKFVPTGGVNLDNVCEWFKAGVLAVGVGSALVKGTPDEVREKAKAFVEKIRG

CTE

SC-TM (N67I, S215P, and E487Q) - foldon-I53-50A embodiment (SEQ ID NO: 93)

(MELLILKANAITTILTAVTFCFASG)QNITEEFYQSTCSAVSKGYLSALRTGWYTSVITIELSN

```
IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDQFDASISQVNEKINQSLAFIR(KSDELL)GYIPEAPRDGQAYVRKDGEWVLLST

FLGSGSHHHHHHHGGSGGSGSEKAAKAEEAARKMEELFKKHKIVAVLRANSVEEAIEKAVAVFA

GGVHLIEITFTVPDADTVIKALSVLKEKGAIIGAGTVTSVEQCRKAVESGAEFIVSPHLDEEISQ

FCKEKGVFYMPGVMTPTELVKAMKLGHTILKLFPGEVVGPQFVKAMKGPFPNVKFVPTGGVNLDN

VCEWFKAGVLAVGVGSALVKGTPDEVREKAKAFVEKIRGCTE

SC-TM (N67I, S215P, and E487Q)-I53-50A - F10 embodiment
                                                                (SEQ ID NO: 94)
(MELLILKANAITTILTAVTFCFASG)QNITEEFYQSTCSAVSKGYLSALRTGWYTSVITIELSN

IKKIKCNGTDAKIKLIKQELDKYKNAVTELQLLMQSTPATNNQARGSGSGRSLGFLLGVGSAIAS

GVAVSKVLHLEGEVNKIKSALLSTNKAVVSLSNGVSVLTSKVLDLKNYIDKQLLPIVNKQSCSIP

NIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDCKIMTSKTDVSSSVITSL

GAIVSCYGKTKCTASNKNRGIIKTFSNGCDYVSNKGVDTVSVGNTLYYVNKQEGKSLYVKGEPII

NFYDPLVFPSDQFDASISQVNEKINQSLAFIR(KSDELL)GSGGSGSGEKAAKAEEAARKMEELF

KKHKIVAVLRANSVEEAIEKAVAVFAGGVHLIEITFTVPDADTVIKALSVLKEKGAIIGAGTVTS

VEQCRKAVESGAEFIVSPHLDEEISQFCKEKGVFYMPGVMTPTELVKAMKLGHTILKLFPGEVVG

PQFVKAMKGPFPNVKFVPTGGVNLDNVCEWFKAGVLAVGVGSALVKGTPDEVREKAKAFVEKIRG

CTE

HMPV-F with A113C, A339C, T160F, I177L - foldon-I53-50A embodiment
                                                                (SEQ ID NO: 95)
(MSWKVVIIFSLLITPQHG)LKESYLEESCSTITEGYLSVLRTGWYTNVFTLEVGDVENLICSDG

PSLIKTELDLTKSALRELKTVSADQLAREEQIENPRQSRFVLGAIALGVCTAAAVTAGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGGYIPEAPRDGQAYVRKDGEWVLLSTFLG

SGSHHHHHHHGGSGGSGSEKAAKAEEAARKMEELFKKHKIVAVLRANSVEEAIEKAVAVFAGGV

HLIEITFTVPDADTVIKALSVLKEKGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLDNVCE

WFKAGVLAVGVGSALVKGTPDEVREKAKAFVEKIRGCTE

HMPV-F with A113C, A339C, T160F, I177L-I53-50A F10 embodiment
                                                                (SEQ ID NO: 96)
(MSWKVVIIFSLLITPQHG)LKESYLEESCSTITEGYLSVLRTGWYTNVFTLEVGDVENLICSDG

PSLIKTELDLTKSALRELKTVSADQLAREEQIENPRQSRFVLGAIALGVCTAAAVTAGVAIAKTI
```

-continued

```
RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPIKFPE

DQFNVALDQVFENIENSQALVDQSNRILSSAEKGNTGGSGGSGSGEKAAKAEEAARKMEELFKKH

KIVAVLRANSVEEAIEKAVAVFAGGVHLIEITFTVPDADTVIKALSVLKEKGAIIGAGTVTSVEQ

CRKAVESGAEFIVSPHLDEEISQFCKEKGVFYMPGVMTPTELVKAMKLGHTILKLFPGEVVGPQF

VKAMKGPFPNVKFVPTGGVNLDNVCEWFKAGVLAVGVGSALVKGTPDEVREKAKAFVEKIRGCTE
```

HMPV-F with A113C, A120C, A339C, T160F, I177L, and Q426C - foldon-I53-50A embodiment (SEQ ID NO: 97)

```
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGYIPEAPRDGQAYVRKDGEWVLLSTFLG

SGSHHHHHHHHGGSGGSGSEKAAKAEEAARKMEELFKKHKIVAVLRANSVEEAIEKAVAVFAGGV

HLIEITFTVPDADTVIKALSVLKEKGAIIGAGTVTSVEQCRKAVESGAEFIVSPHLDEEISQFCK

EKGVFYMPGVMTPTELVKAMKLGHTILKLFPGEVVGPQFVKAMKGPFPNVKFVPTGGVNLDNVCE

WFKAGVLAVGVGSALVKGTPDEVREKAKAFVEKIRGCTE
```

HMPV-F with A113C, A120C, A339C, T160F, I177L, and Q426C - F10 embodiment (SEQ ID NO: 98)

```
(MSWKVVIIFSLLITPQHG)LKESYLEESCSTITEGYLSVLRTGWYINVFTLEVGDVENLICSDG

PSLIKTELDLTKSALRELKTVSADQLAREEQIENPRQSRFVLGAIALGVCTAAAVTCGVAIAKTI

RLESEVTAIKNALKTTNEAVSTLGNGVRVLAFAVRELKDFVSKNLTRALNKNKCDIDDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSGKKGNYACLLREDQGWYCQNAGSTVYYPNE

KDCETRGDHVFCDTACGINVAEQSKECNINISTTNYPCKVSTGRHPISMVALSPLGALVACYKGV

SCSIGSNRVGIIKQLNKGCSYITNQDADTVTIDNTVYCLSKVEGEQHVIKGRPVSSSFDPIKFPE

DQFNVALDQVFENIENSQALVDQSNRILSSAEKGNTGGSGGSGSGEKAAKAEEAARKMEELFKKH

KIVAVLRANSVEEAIEKAVAVFAGGVHLIEITFTVPDADTVIKALSVLKEKGAIIGAGTVTSVEQ

CRKAVESGAEFIVSPHLDEEISQFCKEKGVFYMPGVMTPTELVKAMKLGHTILKLFPGEVVGPQF

VKAMKGPFPNVKFVPTGGVNLDNVCEWFKAGVLAVGVGSALVKGTPDEVREKAKAFVEKIRGCTE
```

HMPV-F 115-BV (A185P)-foldon-I53-50A embodiment (SEQ ID NO: 99)

```
(MSWKVVIIFSLLITPQHG)LKESYLEESCSTITEGYLSVLRTGWYINVFTLEVGDVENLICADG

PSLIKTELDLIKSALRELRIVSADQLAREEQIENPRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE
```

-continued

```
KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNTGYIPEAPRDGQAYVRKDGEWVLLSTFLGS

GSHHHHHHHGGSGGSGSEKAAKAEEAARKMEELFKKHKIVAVLRANSVEEAIEKAVAVFAGGVH

LIEITFTVPDADTVIKALSVLKEKGAIIGAGTVTSVEQCRKAVESGAEFIVSPHLDEEISQFCKE

KGVFYMPGVMTPTELVKAMKLGHTILKLFPGEVVGPQFVKAMKGPFPNVKFVPTGGVNLDNVCEW

FKAGVLAVGVGSALVKGTPDEVREKAKAFVEKIRGCTE

HMPV-F 115-BV (A185P)-I53-50A - F10 embodiment
                                                           (SEQ ID NO: 100)
(MSWKVVIIFSLLITPQHG)LKESYLEESCSTITEGYLSVLRTGWYINVFTLEVGDVENLICADG

PSLIKTELDLIKSALRELRIVSADQLAREEQIENPRRRRFVLGAIALGVATAAAVTAGVAIAKTI

RLESEVTAIKNALKKTNEAVSTLGNGVRVLATAVRELKDFVSKNLTRAINKNKCDIPDLKMAVSF

SQFNRRFLNVVRQFSDNAGITPAISLDLMTDAELARAVSNMPTSAGQIKLMLENRAMVRRKGFGI

LIGVYGSSVIYMVQLPIFGVIDTPCWIVKAAPSCSEKKGNYACLLREDQGWYCQNAGSTVYYPNE

KDCETRGDHVFCDTAAGINVAEQSKECNINISTTNYPCKVSTGRHPISMVALSPLGALVACYKGV

SCSIGSNRVGIIKQLNKGCSYITNQDADTVTIDNTVYQLSKVEGEQHVIKGRPVSSSFDPVKFPE

DQFNVALDQVFESIENSQALVDQSNRILSSAEKGNTGSGGSGSGEKAAKAEEAARKMEELFKKHK

IVAVLRANSVEEAIEKAVAVFAGGVHLIEITFTVPDADTVIKALSVLKEKGAIIGAGTVTSVEQC

RKAVESGAEFIVSPHLDEEISQFCKEKGVFYMPGVMTPTELVKAMKLGHTILKLFPGEVVGPQFV

KAMKGPFPNVKFVPTGGVNLDNVCEWFKAGVLAVGVGSALVKGTPDEVREKAKAFVEKIRGCTE
```

Second Assemblies

The nanostructures of the invention may comprise multiple copies of a trimeric first assembly and multiple copies of a second assembly. The second assembly comprises a protein-protein interface that induces multiple copies of the second polypeptide to self-associate to form the second assemblies. Multiple oligomeric states of the second assembly may be compatible with nanostructure formation, including dimeric (two copies), trimeric (three copies), tetrameric (four copies), pentameric (five copies), hexameric (six copies), or higher oligomeric states. Each copy of the second assembly further comprises a surface-exposed interface that interacts with a complementary surface-exposed interface on a trimeric assembly domain. As described in King et al., Bale et al., and patent publications WO2014124301 A1 and US20160122392 A1, the complementary interface between the trimeric assembly domain and second assembly domain drives the assembly of multiple copies of the trimeric assembly domain and second assembly domain to a target nanostructure. In various specific embodiments:

(a) when each first polypeptide is DS-Cav1-foldon-T33-31A (SEQ ID NO:69) or DS-Cav1-T33-31A (SEQ ID NO:70), each second polypeptide is T33-31B (SEQ ID NO:44);

(b) when each first polypeptide is DS-Cav1-foldon-T33-15B (SEQ ID NO:71) or DS-Cav1-T33-15B (SEQ ID NO:72), each second polypeptide is T33-15A (SEQ ID NO:45);

(c) when each first polypeptide is DS-Cav1-foldon-I53-50A (SEQ ID NO:73) or DS-Cav1-I53-50A (SEQ ID NO:74), each second polypeptide is I53-50B (SEQ ID NO:8), I53-50B.1 (SEQ ID NO:32), I53-50B.1NegT2 (SEQ ID NO:33), or I53-50B.4PosT1 (SEQ ID NO:34);

(d) when each first polypeptide is DS-Cav1-I32-28A (SEQ ID NO:75), each second polypeptide is I32-28B.

Assembly of Full Valency Nanostructures by In Vitro Assembly of Two Components

In some embodiments, each trimeric first assembly of the nanostructure bears an identical F protein as a genetic fusion; these nanostructures display the F protein at full (100%) valency. Such nanostructures are produced from purified first polypeptides and second polypeptides in a process called in vitro assembly. Purified trimeric first polypeptides comprising an F protein, are mixed with appropriate second polypeptides in an approximately 1:1 molar ratio in aqueous conditions (see FIG. 1). The second assembly interacts with the trimeric first assembly in order to drive assembly of the target nanostructure. Successful assembly of the target nanostructure can be confirmed by analyzing the in vitro assembly reaction by common biochemical or biophysical methods used to assess the physical size of proteins or protein assemblies, including but not limited to size exclusion chromatography, native (non-denaturing) gel electrophoresis, dynamic light scattering, multi-angle light scattering, analytical ultracentrifugation, negative stain electron microscopy, cryo-electron microscopy, or X-ray crystallography. If necessary, the assembled nanostructure can be purified from other species or molecules present in the in vitro assembly reaction using preparative techniques commonly used to isolate proteins by their physical size, including but not limited to size exclusion chromatography, preparative ultracentrifugation, tangential flow filtration, or preparative gel electrophoresis. The presence of the F protein in the nanostructure can be assessed by techniques commonly used to determine the identity of protein molecules in aqueous solutions, including but not limited to SDS-PAGE, mass spectrometry, protein sequencing, or amino acid analysis. The accessibility of the F protein on the exterior of the particle, as well as its conformation or antigenicity, can be assessed by techniques commonly used to detect the presence and conformation of an antigen, including but not limited to binding by monoclonal antibodies, conformation-specific monoclonal antibodies, or antisera specific to the antigen.

In Vitro Assembly of Partial Valency Nanostructures

In other embodiments, the nanostructures of the invention comprise one or more copies of trimeric first assemblies bearing F proteins as genetic fusions as well as one or more trimeric first assemblies that do not bear F proteins as genetic fusions; these nanostructures display the F proteins at partial valency. These partial valency nanostructures are produced by performing in vitro assembly with mixtures of first polypeptides in which the fraction of trimeric first assemblies bearing an F protein as a genetic fusion is equal to the desired valency of the antigen in the resulting nanostructure. The in vitro assembly reaction typically contains an approximately 1:1 molar ratio of total first polypeptides to total second polypeptides. By way of non-limiting example, performing an in vitro assembly reaction with a mixture of trimeric assemblies in which one half of the first polypeptides bear an F protein as a genetic fusion would yield an assembled nanostructure with an F protein valency of 50%. That is, 50% of the possible sites for F protein display on the nanostructure would be occupied. By way of non-limiting example, if the nanostructure is a 120-subunit assembly with icosahedral symmetry, the nanostructure comprises 20 total trimeric building blocks, and a 50% valency nanostructure displays 10 of the possible 20 F protein trimers. In this way, the ratio of F protein-bearing first polypeptides to first polypeptides lacking F proteins in an in vitro assembly reaction can be used to precisely tune the F protein valency of the resulting nanostructures. It will be understood by those of skill in the art that it is the average valency that can be tuned in this manner; the valency of individual nanostructures in the mixture will be a distribution centered around the average. Successful assembly of such partial valency nanostructures can be assessed using the techniques described above for evaluating full-valency nanostructures, and, if necessary, the partial valency nanostructures can be purified using the methods described for purifying full-valency nanostructures. The average valency of F protein-bearing first polypeptides in a given sample can be assessed by quantitative analysis using the techniques described above for evaluating the presence of F proteins in full-valency nanostructures.

In Vitro Assembly of Nanostructures Co-Displaying Multiple F Proteins

In other embodiments, the nanostructures of the invention comprise two or more distinct first polypeptides bearing different F proteins as genetic fusions; these nanostructures co-display multiple different F proteins on the same nanostructure. These multi-antigen nanostructures are produced by performing in vitro assembly with mixtures of first polypeptides in which each first polypeptide bears one of two or more distinct F proteins as a genetic fusion. The fraction of each first polypeptide in the mixture determines the average valency of each F protein in the resulting nanostructures. The in vitro assembly reaction typically contains an approximately 1:1 molar ratio of total trimeric first polypeptides to total second polypeptides. The presence and average valency of each F protein-bearing first polypeptides in a given sample can be assessed by quantitative analysis using the techniques described above for evaluating the presence of F proteins in full-valency nanostructures.

In various embodiments, the nanostructures are between about 20 nanometers (nm) to about 40 nm in diameter, with interior lumens between about 15 nm to about 32 nm across and pore sizes in the protein shells between about 1 nm to about 14 nm in their longest dimensions.

In one embodiment, the nanostructure has icosahedral symmetry. In this embodiment, the nanostructure may comprise 60 copies of the first polypeptide and 60 copies of the second polypeptide. In one such embodiment, the number of identical first polypeptides in each first assembly is different than the number of identical second polypeptides in each second assembly. For example, in one embodiment, the nanostructure comprises twelve first assemblies and twenty second assemblies; in this embodiment, each first assembly may, for example, comprise five copies of the identical first polypeptide, and each second assembly may, for example, comprise three copies of the identical second polypeptide. In another embodiment, the nanostructure comprises twelve first assemblies and thirty second assemblies; in this embodiment, each first assembly may, for example, comprise five copies of the identical first polypeptide, and each second assembly may, for example, comprise two copies of the identical second polypeptide. In a further embodiment, the nanostructure comprises twenty first assemblies and thirty second assemblies; in this embodiment, each first assembly may, for example, comprise three copies of the identical first polypeptide, and each second assembly may, for example, comprise two copies of the identical second polypeptide. All of these embodiments are capable of forming synthetic nanomaterials with regular icosahedral symmetry. In various further embodiments, oligomeric states of the first and second polypeptides are as follows:

I53-34A: trimer+I53-34B: pentamer;
I53-40A: pentamer+I53-40B: trimer;
I53-47A: trimer+I53-47B: pentamer;
I53-50A: trimer+I53-50B: pentamer;
I53-51A: trimer+I53-51B: pentamer;
I32-06A: dimer+I32-06B: trimer;
I32-19A: trimer+I32-19B: dimer;
I32-28A: trimer+I32-28B: dimer;
I52-03A: pentamer+I52-03B: dimer;
I52-32A: dimer+I52-32B: pentamer; and
I52-33A: pentamer+I52-33B: dimer In another embodiment, the nanostructure of any embodiment or combination of embodiments of the invention has one or more of the following characteristics, each as demonstrated in the examples that follow:

(a) binds prefusion F-specific antibodies including but not limited to monoclonal antibody D25;
(b) forms a symmetrical structure, including but not limited to an icosahedral structure;
(c) is stable at 50° C.; and/or
(d) is stable in 2.25M guanidine hydrochloride.

In another aspect, the present invention provides isolated nucleic acids encoding a fusion protein of the present invention. The isolated nucleic acid sequence may comprise RNA or DNA. As used herein, “isolated nucleic acids” are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the invention.

In a further aspect, the present invention provides recombinant expression vectors comprising the isolated nucleic acid of any embodiment or combination of embodiments of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, TX). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic, such as mammalian cells. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, NY). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In a further aspect, the invention provides an immunogenic composition comprising an effective amount of the nanostructure of any embodiment or combination of embodiments of the invention and a pharmaceutically acceptable carrier. The composition may comprise (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the composition additionally includes a stabilizer, e.g., a molecule which substantially prevents or reduces chemical and/or physical instability of the nanostructure, in lyophilized or liquid form. Exemplary stabilizers include sucrose, sorbitol, glycine, inositol, sodium chloride, methionine, arginine, and arginine hydrochloride.

The nanostructure may be the sole active agent in the composition, or the composition may further comprise one or more other agents suitable for an intended use, including but not limited to adjuvants to stimulate the immune system generally and improve immune responses overall. Any suitable adjuvant can be used. The term "adjuvant" refers to a compound or mixture that enhances the immune response to an antigen. Exemplary adjuvants include, but are not limited to, Adju-Phos™, Adjumer™, albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod™, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL.TM., MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. Selection of an adjuvant depends on the subject to be treated. Preferably, a pharmaceutically acceptable adjuvant is used.

In another aspect, the invention provides methods for generating an immune response to paramyxovirus and/or pneumovirus F protein in a subject, comprising administering to the subject an effective amount of the immunogenic composition of any embodiment or combination of embodiments of the invention to generate the immune response. In a further aspect, the invention provides methods for treating or preventing a paramyxovirus and/or pneumovirus infection in a subject, comprising administering to the subject an effective amount of the immunogenic composition of any embodiment or combination of embodiments of the invention, thereby treating or preventing paramyxovirus and/or pneumovirus infection in the subject.

In one embodiment, the paramyxovirus and/or pneumovirus comprises respiratory syncytial virus. "Respiratory Syncytial Virus" and "RSV" refer to a negative-sense, single-stranded RNA virus that causes a respiratory disease, especially in children. When the method comprises treating an RSV infection, the immunogenic compositions are administered to a subject that has already been infected with the RSV, and/or who is suffering from symptoms (including but not limited to lower respiratory tract infections, upper respiratory tract infections, bronchiolitis, pneumonia, fever, listlessness, diminished appetite, recurrent wheezing, and asthma) indicating that the subject is likely to have been infected with the RSV. As used herein, "treat" or "treating" includes, but is not limited to accomplishing one or more of the following: (a) reducing paramyxovirus and/or pneumovirus titer in the subject; (b) limiting any increase of paramyxovirus and/or pneumovirus titer in the subject; (c) reducing the severity of paramyxovirus and/or pneumovirus symptoms; (d) limiting or preventing development of paramyxovirus and/or pneumovirus symptoms after infection; (e) inhibiting worsening of paramyxovirus and/or pneumovirus symptoms; (f) limiting or preventing recurrence of paramyxovirus and/or pneumovirus symptoms in subjects that were previously symptomatic for paramyxovirus and/or pneumovirus infection; and/or promoting maternal transmission of paramyxovirus and/or pneumovirus antibodies to infants (after maternal immunization).

When the method comprises limiting a paramyxovirus and/or pneumovirus infection, the immunogenic compositions are administered prophylactically to a subject that is not known to be infected, but may be at risk of exposure to the paramyxovirus and/or pneumovirus. As used herein, "limiting" means to limit RSV infection in subjects at risk of RSV infection. Groups at particularly high risk include children under age 18 (particularly infants 3 years or younger), adults over the age of 65, and individuals suffering from any type of immunodeficiency.

As used herein, an "effective amount" refers to an amount of the immunogenic composition that is effective for treating and/or limiting RSV infection. The immunogenic compositions are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Polypeptide compositions may also be administered via microspheres, liposomes, immune-stimulating complexes (ISCOMs), or other microparticulate delivery systems or sustained release formulations introduced into suitable tissues (such as blood). Dosage regimens can be adjusted to provide the optimum desired response (e.g., a therapeutic or prophylactic response). A suitable dosage range may, for instance, be 0.1 ug/kg-100 mg/kg body weight of the F protein or antigenic fragment thereof. The composition can be delivered in a single bolus, or may be administered more than once (e.g., 2, 3, 4, 5, or more times) as determined by attending medical personnel.

In one embodiment, the administering results in production of paramyxovirus and/or pneumovirus neutralizing antibodies in the subject. In another embodiment, the neutralizing antibodies are present in sera of the subject at a titer ($1/ID_{50}$) of at least 1,000; in other embodiments, the neutralizing antibodies are present in sera of the subject at a titer of 2,000 or 5,000.

Examples

Methods:
Expression and Screening of Trimeric Building Blocks Comprising an F Protein and a Trimeric Assembly Domain Human codon-optimized sequences for trimeric building blocks including and lacking DS-Cav1 fusions were ordered from Genscript. Building blocks for single-component nanostructures (i.e., I3-01) were cloned into the pcDNA3.1 vector (ThermoFisher Scientific) containing one CMV promoter, while building blocks for two-component nanostructures (e.g., I53-50) were cloned into the pBudCE4.1™ vector (ThermoFisher Scientific) containing both CMV and EF-1α promoters. Recombinant proteins were expressed by transient transfection of Expi293F™ cells (ThermoFisher Scientific) using polyethylenimine (PEI). Cell cultures were harvested five days post-transfection by centrifugation. Secreted proteins were analyzed by ELISA, using either direct coating of the cell supernatants or by sandwich ELISA. Briefly, 96-well MaxiSorp™ plates (Nunc) were coated with cell supernatant for direct ELISA or murine anti-His tag monoclonal antibody (ThermoFisher Scientific) for sandwich ELISA. Secreted proteins were detected using the human Palivizumab, MPE8, RSD5, and D25 monoclonal antibodies. Transfected Expi293F cells were fixed and permeabilized with BD cytofix/cytoperm (BD Biosciences), incubated with human Palivizumab, MPE8, and D25 monoclonal antibodies, and stained with Alexa Fluor 647-conjugated anti-human IgG antibody (Jackson ImmunoResearch). Stained cells were counted with a FACS Fortessa™ flow cytometer (BD Biosciences). Analysis was performed with FlowJo™ software. Cell lines were routinely tested for mycoplasma contamination.

Expression and Purification of DS-Cav1-I53-50A

Lentivirus was produced by transient transfection of 293T (ATCC) cells using linear 25-kDa polyethyleneimine (PEI; Polysciences). Briefly, 4×10⁶ cells were plated onto 10 cm tissue culture plates. After 24 h, 3 µg of psPAX2, 1.5 µg of pMD2G (Addgene™ plasmid #12260 and #12259, respectively) and 6 µg of lentiviral vector plasmid were mixed in 500 µl diluent (5 mM HEPES, 150 mM NaCl, pH=7.05) and 42 µl of PEI (1 mg/ml) and incubated for 15 min. The DNA/PEI complex was then added to the plate drop-wise. Lentivirus was harvested 48 h post-transfection and concentrated 100-fold by low-speed centrifugation at 8000 g for 18 h. Transduction of the target cell line was carried out in 125 mL shake flasks containing 10×10⁶ cells in 10 mL of growth media. 100 uL of 100× lentivirus was added to the flask and the cells were incubated with shaking (225 rpm) at 37° C., in 8% $CO_2$ for 4-6 h. 20 mL of growth media was added to the shake flask after 4-6 h.

Transduced cells were expanded every other day to a density of 1×10⁶ cells/ml until a final culture size of 4 L was reached. The media was harvested after 17 days of total incubation after measuring final cell concentration (~5×10⁶ cells/mL) and viability (~90% viable). Culture supernatant was harvested by low-speed centrifugation to remove cells from the supernatant. NaCl and $NaN_3$ were added to final concentrations of 250 mM and 0.02%, respectively. The supernatant was loaded over one 5 mL HisTrap™ FF Crude column (GE Healthsciences) at 5 ml/min by an AKTA Pure™ (GE Healthsciences). The nickel elution was applied to a HiLoad™ 16/600 Superdex 200 pg column (GE Healthsciences) to further purify the target protein by size-exclusion chromatography. The size-exclusion purified target protein was snap frozen in liquid nitrogen and stored at −80° C.

In Vitro Assembly of DS-Cav1-Bearing Nanostructures

100% valency particles (20 DS-Cav1 trimers per icosahedral nanostructure) were prepared by mixing DS-Cav1-foldon-I53-50A trimers and I53-50B.4PT1 pentamers at 50 µM each and incubating with rocking overnight at 4° C. In some cases, assembled nanostructures were purified from excess components remaining in the in vitro assembly reaction using a GE Sephacryl S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin™ 20 30 kDa MWCO centrifugal filter, and quantified using an Agilent 8454 spectrophotometer.

66% valency particles (~14 DS-Cav1 trimers per icosahedral nanostructure) were prepared by mixing DS-Cav1-foldon-I53-50A trimers, I53-50A trimers, and I53-50B.4PosT1 pentamers at 50, 25, and 75 µM, respectively. 33% valency particles (~7 DS-Cav1 trimers per icosahedral nanostructure) were prepared by mixing DS-Cav1-foldon-I53-50A trimers, I53-50A trimers, and I53-50B.4PosT1 pentamers at 25, 50, and 75 µM, respectively. The in vitro assembly reactions were allowed to incubate with rocking overnight at 4° C. In some cases, assembled nanostructures were purified from excess components remaining in the in vitro assembly reaction using a GE Sephacryl™ S-500 HR 16/60 column in a buffer comprising 25 mM Tris pH 8, 250 mM NaCl, 5% glycerol. Sample load and SEC fractions were analyzed by SDS-PAGE in the presence and absence of reducing agent. Peak fractions were pooled, concentrated using a GE Vivaspin™ 20 30 kDa MWCO centrifugal filter, and quantified using an Agilent 8454 spectrophotometer after centrifuging at ~21,000 g for 10 minutes at 4° C.

Samples were then transferred to cryogenic tubes in 1 mL aliquots at 1.1 mg/mL for the 33% valency particles and 0.6 mg/mL for the 66% valency particles, flash frozen in liquid nitrogen, and stored at −80° C.

Electron Microscopy of DS-Cav1-Bearing Nanostructures

Samples were prepared for negative stain EM by diluting to 0.01 mg/mL using 25 mM Tris pH 8, 250 mM NaCl, 5% glycerol and 3.5 µL was incubated on a glow-discharged, copper, carbon-coated grid for 20 seconds before blotting away the liquid with a piece of Whatman No. 1 filter paper. Within seconds of blotting away the sample, a 3.5 µL droplet of stain (2% w/v uranyl formate) was deposited and blotted away immediately, and then a second cycle of staining/blotting was performed.

Circular Dichroism (CD) Spectropolarimetry

CD spectra from F proteins (0.5 mg ml⁻¹) were recorded on a Chirascan™ spectropolarimeter (Applied Photophysics) over the wavelength range of 195 to 260 nm at a bandwidth of 1 nm, step size of 0.5 nm, and 1 s per step. The spectra in the far-ultraviolet region required an average of three scans and were subtracted from blank spectra performed with buffer. Thermal denaturation was monitored by performing scans at intervals of 1° C., after equilibration for 1 min at each temperature. Data were fitted to a simple first order curve. The values of $\Delta A222$ are represented on the y axis as the percentage of the values recorded at 20° C.

Enzyme-Linked Immunosorbent Assay (ELISA)

To test specific binding of antibody or sera, 96-well MaxiSorp™ plates (Nunc) were coated with serial dilutions of tissue culture supernatants from cells expressing trimeric building blocks comprising F proteins and a trimeric assembly domain or 2 µg ml⁻¹ of the following purified proteins: Ds-Cav1 with foldon, Ds-Cav1 fused to a trimeric first polypeptide or DS-Cav1-displaying nanostructures. Plates were blocked with 1% bovine serum albumin (BSA) and incubated with titrated antibodies (D25, MPE8, Palivizumab, RSD5) or murine sera followed by AP-conjugated goat anti-human IgG (Southern Biotech, 2040-04) or goat anti-mouse IgG (Southern Biotech, 1030-04). Plates were then washed with PBS buffer (Gibco, Invitrogen), 0.05% Tween-20 and substrate (p-NPP, Sigma) was added and plates were read at 405 nm.

Surface Plasmon Resonance (SPR)

The experiments were carried out at 25° C. on a ProteON™ XPR-36 instrument (Bio-Rad Laboratories) in a PBS buffer (Gibco, Invitrogen), 0.05% Tween-20. The D25 mAb was immobilized on a GLM sensor chip surface through amine coupling at 1000 response units (RU) and a blank surface with no protein was created under identical coupling conditions for use as a reference. Monoclonal antibodies (D25, MPE8, Palivizumab and 131-2a) were injected at a flow rate of 100 µl/min, at concentrations of 50 nM in different sensor channels. The data were processed using Proteon software and double referenced by subtraction of the blank surface and buffer only injection before local fitting of the data.

Vaccination and Serological Analysis

Female BALB/c mice 6-9 weeks of age were obtained from ENVIGO Laboratories (Italy). All proteins were formulated with AddaVax™ adjuvant (Invivogen) according to the manufacturer's instruction. Mice were immunized subcutaneously (s.c) with a total protein dose corresponding to 5 µg of the DS-Cav1 antigen equivalent on day 0, 14, and 28 in 50% AddaVax™ in PBS. Mice were bled on day 24 and 40. Recovered sera were used to measure binding and neutralizing titers. Binding titers were measured by coating 3 µg/ml of DS-Cav1, I53-50 nanostructures or I53-50 nanostructure subunits.

Virus Neutralization Assay and Microscopy Analysis

Neutralization of RSV infection by sera was measured using a micro-neutralization flow cytometry-based assay. Serial dilutions of sera were pre-incubated with RSV for 1 hour at 37° C. and added to 10000 HEp-2 (ATCC® CCL-23™) cells/well in 96-well flat-bottom plates (MOI of 1). After 24 hours, cells were washed, detached and fixed with 2% formaldehyde. Percentage of GFP positive cells were measured by High throughput FACS with an Intellicyt coupled to an automated platform. The Tissue Culture Inhibiting Dilution (TCID) neutralizing 50% of the Infection ($TCID_{50}$) was calculated by nonlinear regression with Prism 7 (GraphPad Software).

Non-Human Primate (NHP) Immunization

Rhesus macaques were immunized i.m. (right quadriceps) at weeks 0 and 4 with trimeric DS-Cav1 (50 µg; n=4) or DS-Cav1-foldon-I53-50 nanostructures (96 µg, comprising 50 µg of displayed DS-Cav1; n=5) formulated in the MF59-like adjuvant SWE. Sera were obtained at weeks 6 and 16 for serological analysis.

Stability of DS-Cav1-Bearing Nanostructures by Relative Binding to D25

Experiments were carried out at 20° C. on a ProteON™ XPR-36 instrument (Bio-Rad Laboratories) in a PBS buffer (Gibco, Thermo Fisher Scientific) and 0.05% Tween-20 (Sigma). 100 nM D25 antibody was immobilized on a GLM sensor chip surface through amine coupling (EDC/NHS chemistry) and a blank surface with no antibody was created under identical coupling conditions for use as a reference. Analyte proteins (soluble DS-Cav1, soluble DS-Cav1-I53-50A and DS-Cav1-foldon-I53-50 nanostructures), heat stressed at different temperatures (20, 50, 70 or 80° C.) for 1 h, were injected at a flow rate of 100 µl/min, at a concentration of 50 nM in the different sensor channels. Data were processed using Proteon software and double referenced by subtraction of the blank surface and buffer-only injection before local fitting of the data.

Chemical Denaturation of Nanostructure-Related Proteins

Trimeric DS-Cav1, DS-Cav1-I53-50A, DS-Cav1-I53-50, I53-50, trimeric I53-50A, or pentameric I53-50B.4PT1 was diluted to a final concentration of 2.5 µM in 25 mM Tris pH 8, 250 mM NaCl, 5% glycerol with varying concentrations of guanidine hydrochloride, ranging from 0 M to 6.5 M, increasing in 0.25 M increments. Samples were prepared in triplicate and incubated for 16 hours at ambient temperature. On a Cary Eclipse Fluorescence Spectrophotometer, intrinsic fluorescence was measured for each guanidine hydrochloride concentration of each protein and of each replicate. A Peltier controller was used in the cell holder to maintain a temperature of 25° C. throughout all experiments. Using a 10 mm cell (Agilent Cuvette, part #6610021600), fluorescence spectra were collected, exciting at 290 nm and scanning emission from 310 nm to 510 nm at a rate of 60 nm/minute with a bandpass of 1 nm.

Statistical Analysis

No statistical methods were used to predetermine sample size. Data were analyzed with Prism 6 (GraphPad™ Software) using the two-tailed non-parametric Mann-Whitney U test for two groups' comparison, or Kruskall-Wallis test (and Dunn's posttest) when three or more groups were compared.

Results

Trimeric Building Blocks Comprising an F Protein and a Trimeric Assembly Domain

Figure 2:
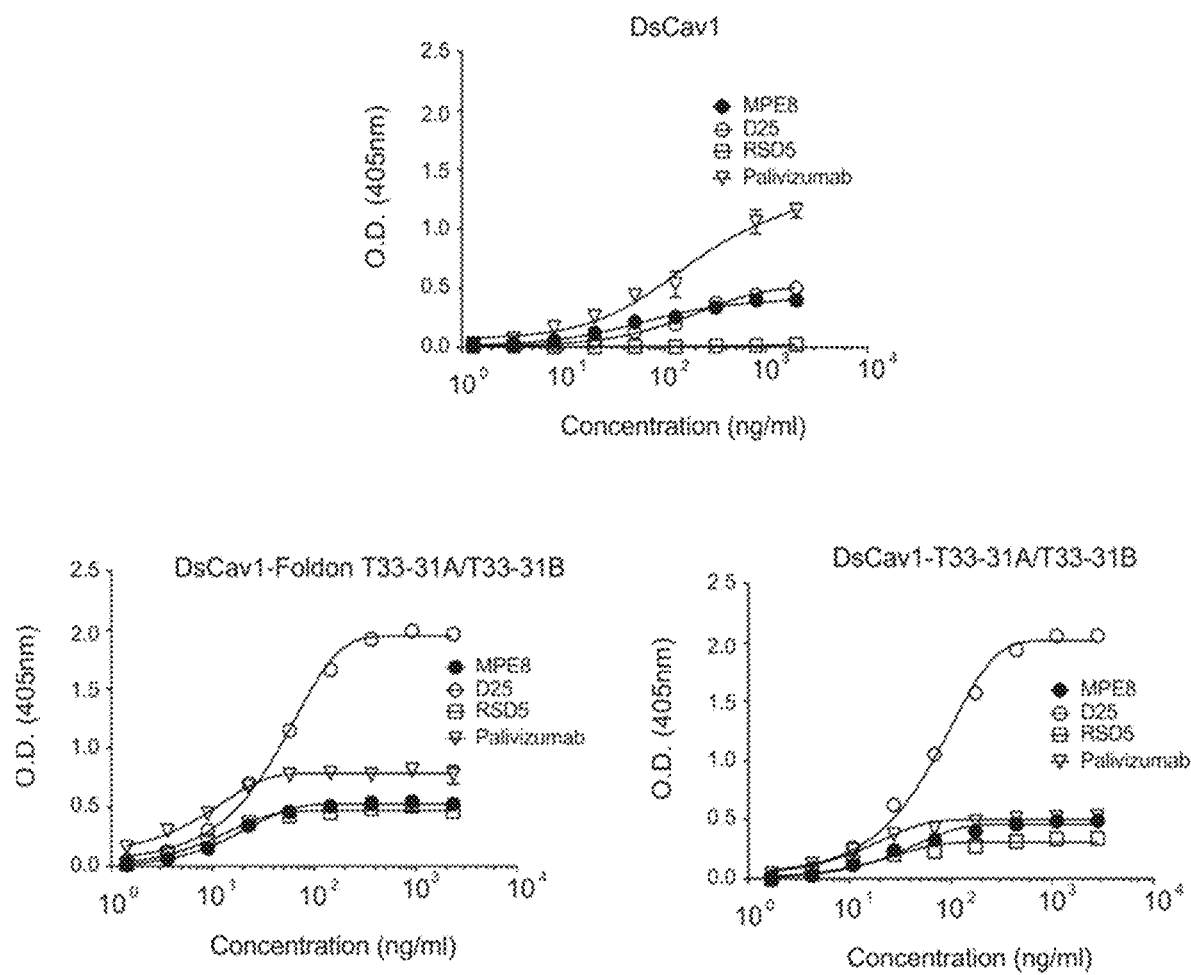
FIG. 2 shows graphs illustrating detection of secreted DS-Cav1, DS-Cav1-foldon-T33-31A, and DS-Cav1-T33-31A fusion proteins in tissue culture supernatants. ELISA assays were performed on tissue culture supernatants from cells expressing DS-Cav1 (top), DS-Cav-1-foldon-T33-31A/T33-31B (bottom left), and DS-Cav-1-T33-31A/T33-31B (bottom right). Four different monoclonal antibodies that bind RSV F were used to evaluate the presence of DS-Cav1 or DS-Cav1 fusion proteins in the supernatants. The results confirm the secretion of proteins comprising well-folded RSV F antigen.

Several trimeric building blocks, each comprising an F protein genetically fused to a trimeric assembly domain, were found to be secreted from HEK293F cells with their F proteins in a well-folded, prefusion conformation as judged by prefusion-specific monoclonal antibody binding in ELISA assays. FIG. 2 shows an example of ELISA data analyzing the supernatant of HEK293F cells expressing DS-Cav1-foldon, DS-Cav1-foldon-T33-31A, and DS-Cav1-T33-31A. Several other trimeric building blocks yielded detectable secretion of well-folded, prefusion F proteins.

Expression and Purification of DS-Cav1-Foldon-I53-50A

Figure 3:
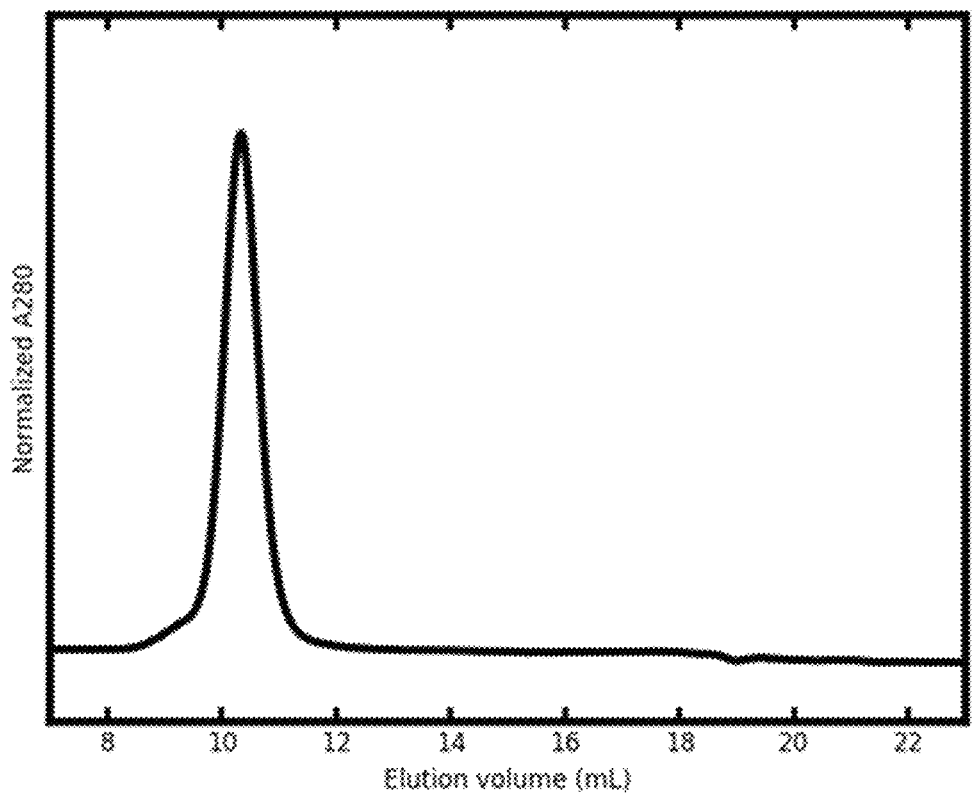
FIG. 3 shows size-exclusion chromatography of DS-Cav1-I53-50A. Protein purified from tissue culture supernatants by immobilized metal affinity chromatography was applied to a Superose™ 6 10/300 GL size exclusion column. The protein eluted as a single, monodisperse species.

A lentiviral vector encoding DS-Cav1-foldon-I53-50A was used to transduce HEK293F cells for large-scale expression. The secreted protein was purified from tissue culture supernatants by immobilized metal affinity chromatography and size exclusion chromatography. Size exclusion chromatograms (FIG. 3) indicated that the purified protein formed a single, monodisperse species.

Expression and Purification of I53-50B.4PT1

I53-50B.4PT1, a pentameric protein comprising a second assembly domain that interacts with the trimeric assembly domain in I53-50A or DS-Cav1-foldon-I53-50A to drive assembly of icosahedral I53-50-based nanostructures, was expressed and purified as described in Bale et al. and patent publication US20160122392 A1.

In Vitro Assembly and Characterization of DS-Cav1-Bearing I53-50 Nanostructures

Figure 4:
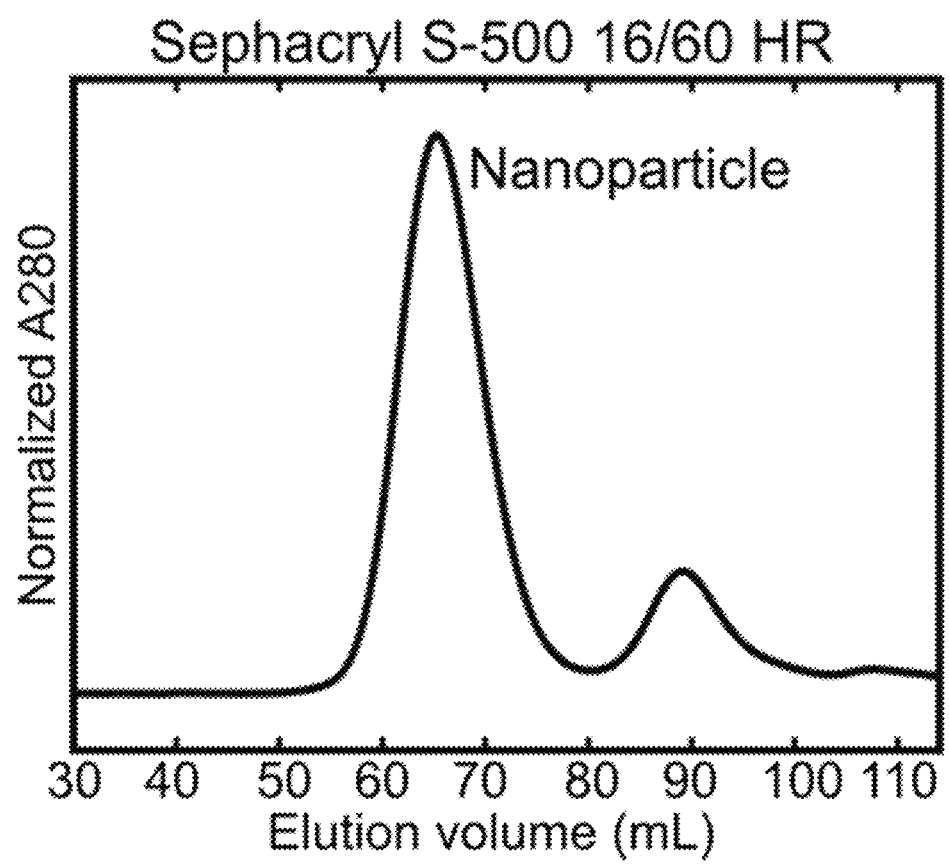
FIG. 4 shows size exclusion chromatography of in vitro-assembled DS-Cav1-I53-50 nanostructures. Purified DS-Cav1-I53-50A and I53-50B.4PT1 proteins were mixed at an approximately 1:1 molar ratio, incubated overnight at 4° C., and then applied to a Sephacryl S-500 16/60 HR size exclusion column. The assembled nanostructure eluted as a single, monodisperse peak around 65 mL, while excess DS-Cav1-I53-50A trimeric component eluted around 90 mL.
Figure 5:
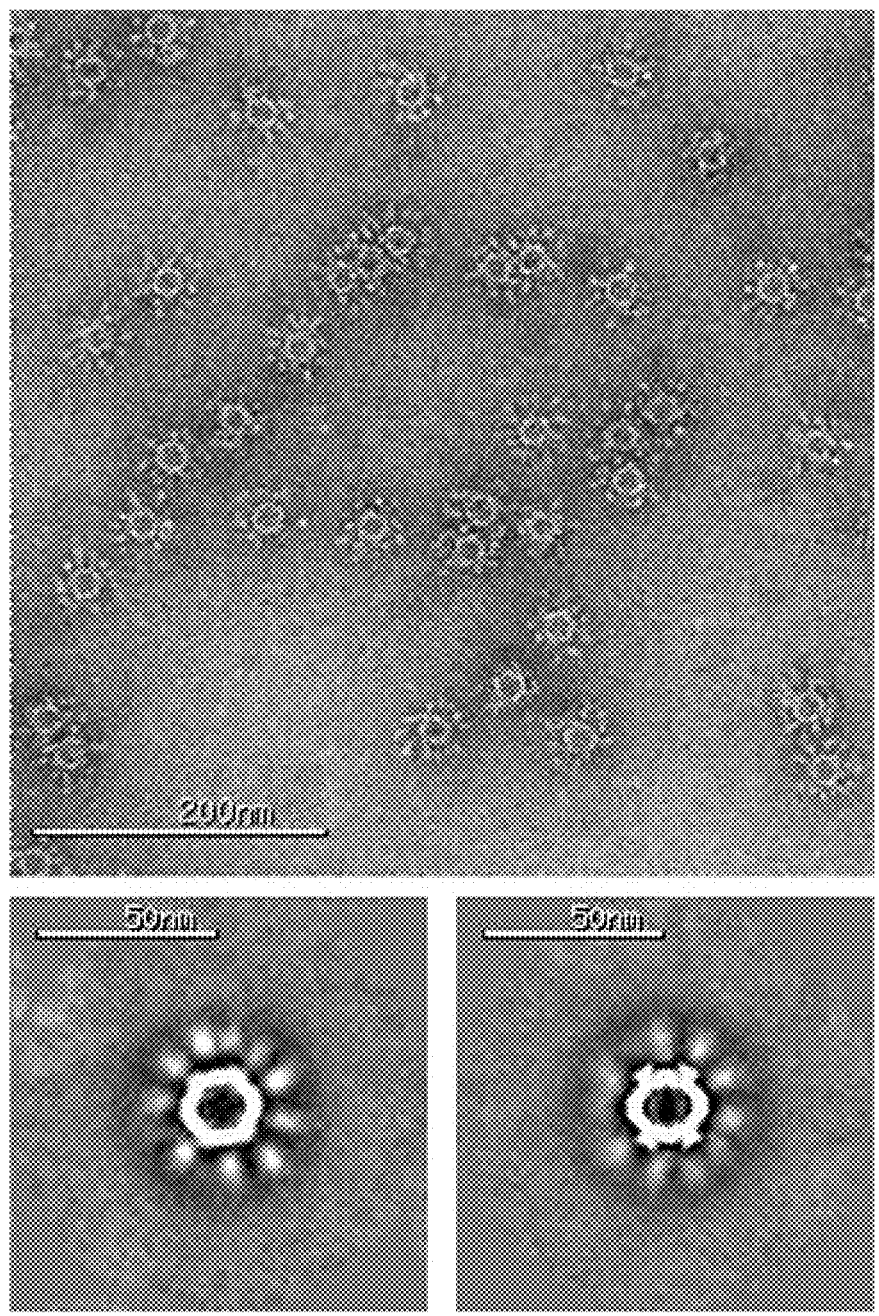
FIG. 5 shows a negative stain electron micrograph and two-dimensional class averages of in vitro-assembled DS-Cav1-I53-50 nanostructures. In vitro-assembled DS-Cav1-I53-50 nanostructures, purified by size exclusion chromatography, were imaged by negative stain electron microscopy (top). Averaging many nanostructures yielded two-dimensional class averages (bottom) that indicate that the I53-50 portion of the nanostructures is highly ordered and consistent, while the precise three-dimensional position of the displayed antigen varies slightly due to the flexible nature of the linker between the DS-Cav1 and I53-50A domains of the DS-Cav1-I53-50A fusion protein.
Figure 6A:
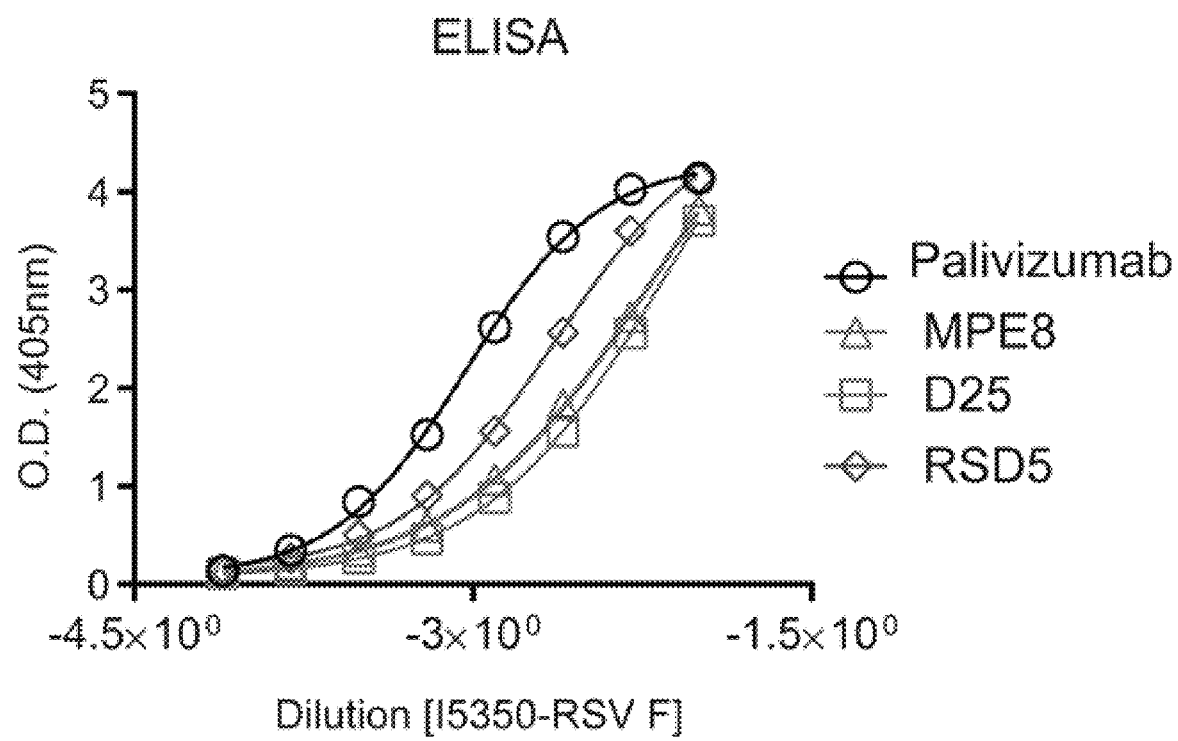
FIG. 6A-6C show a series of graphs depicting the antigenicity of DS-Cav1-I53-50 nanostructures. Analysis of purified DS-Cav1-I53-50 nanostructures by ELISA (FIG. 6A) using four RSV F-specific monoclonal antibodies, including the prefusion-specific antibodies MPE8, D25, and RSD5, indicated that the DS-Cav1 antigen is correctly folded and maintained in the prefusion state when multivalently displayed on DS-Cav1-I53-50 nanostructures. This finding was confirmed by surface plasmon resonance measurements using multiple RSV F-specific antibodies (FIG. 6B-6C), which, when compared to trimeric DS-Cav1, further suggested that multivalent display of DS-Cav1 results in an avidity effect that reduces the dissociation rate of the antibodies.
Figure 6B:
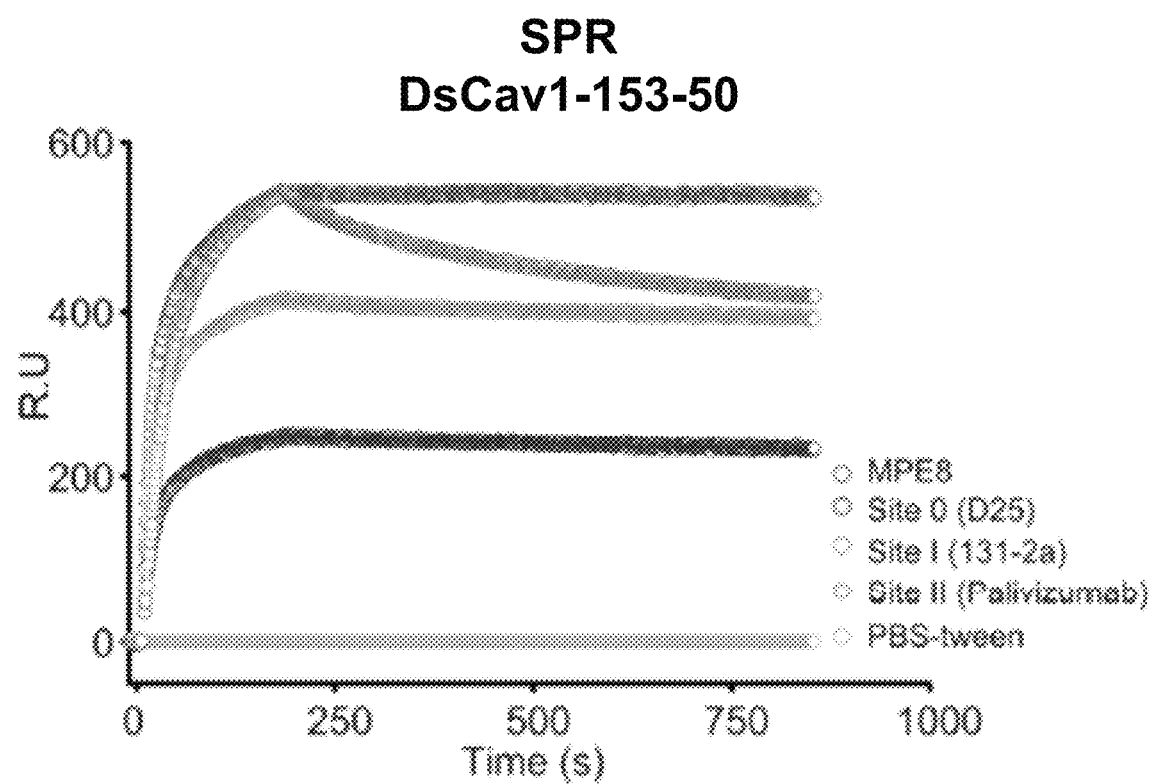
Figure 6C:
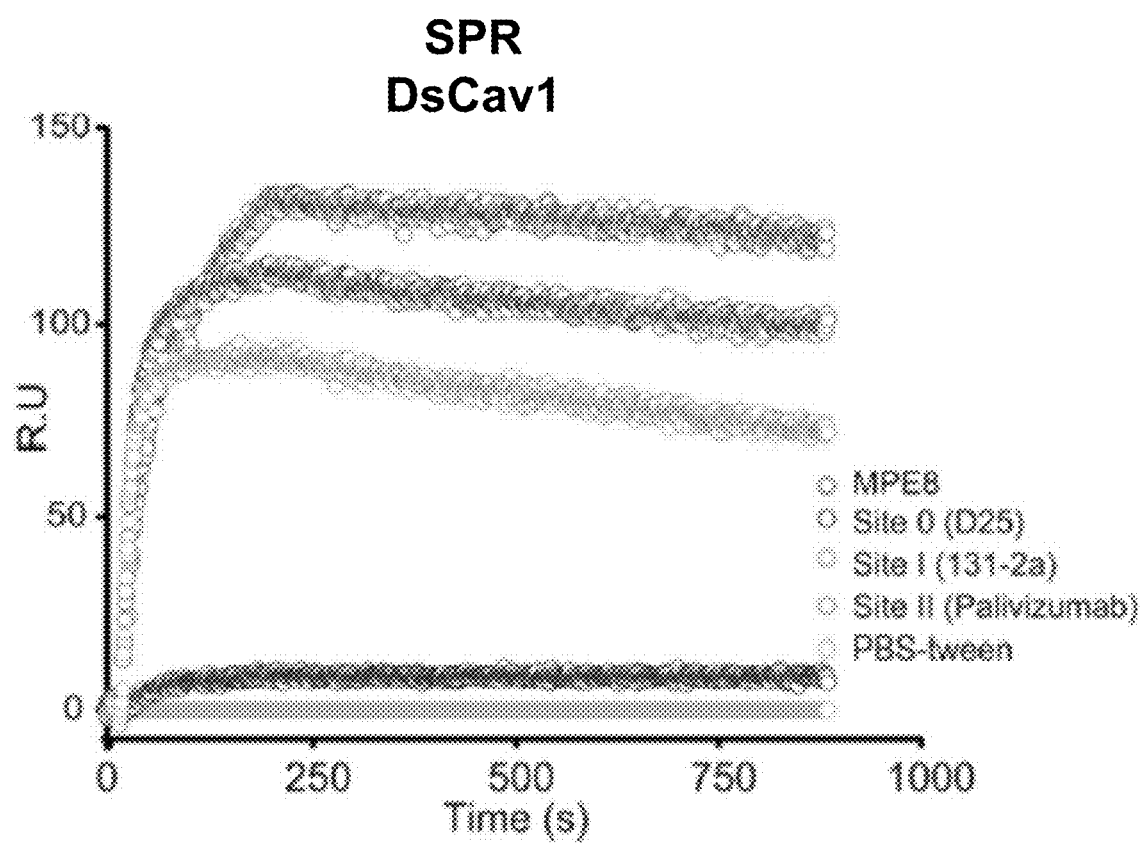

I53-50 is a 120-subunit two-component nanostructure with icosahedral symmetry comprising 20 trimeric (I53-50A) and 12 pentameric (I53-50B) building blocks, as recently described by Bale et al. The N terminus of I53-50A is exposed on the exterior of the I53-50 nanostructure, which enables the display of antigens on the nanostructure exterior through genetic fusion to the I53-530A N terminus. Purified DS-Cav1-foldon-I53-50A and I53-50B.4PT1 were assembled in vitro to form 120-subunit icosahedral nanostructures displaying various amounts of DS-Cav1 on the nanostructure exteriors by mixing the two purified proteins in various molar ratios. In separate preparations, nanostructures displaying DS-Cav1 at valencies of 100% (20 trimers), 66% (~14 trimers), and 33% (~7 trimers) were prepared as described above. The species present in the in vitro assembly reactions after overnight incubation were assessed by several techniques, including size exclusion chromatography-multi-angle light scattering (SEC-MALS), dynamic light scattering, and UV/vis spectroscopy. Assembled, 120-subunit nanostructures were purified from the in vitro assembly reactions using size exclusion chromatography (an example chromatogram obtained using the 100% valency nanostructures is presented in FIG. 4). The purified nanostructures were characterized by negative stain electron microscopy, which revealed fields of monodisperse particles in which DS-Cav1 was clearly visible as spikes projecting outward from the core icosahedral I53-50 assembly (an example micrograph obtained using the 100% valency particles is presented in FIG. 5). ELISA assays using monoclonal antibodies specific to the prefusion conformation confirmed that the DS-Cav1 thus displayed on the nanostructure exteriors was well-folded and antigenically intact (FIG. 6). Surface plasmon resonance experiments evaluating the kinetics of monoclonal antibody binding revealed that antibody dissociation from the 100% valency DS-Cav1-foldon-I53-50 nanostructures was slower than from DS-Cav1-foldon trimers, likely due to avidity effects deriving from the multivalent presentation of DS-Cav1 on the nanostructure exterior (FIG. 6). Together, these experiments confirmed that the DS-Cav1-foldon-I53-50 nanostructures formed monodisperse, icosahedral nanostructures that display well-folded, antigenically intact DS-Cav1 trimers on their exteriors. These findings motivated experiments to evaluate the utility of the DS-Cav1-foldon-I53-50 nanostructures as immunogens for inducing humoral immune responses against DS-Cav1 in animals.

Immunogenicity of DS-Cav1-Foldon-I53-50 Nanostructures

Figure 7:
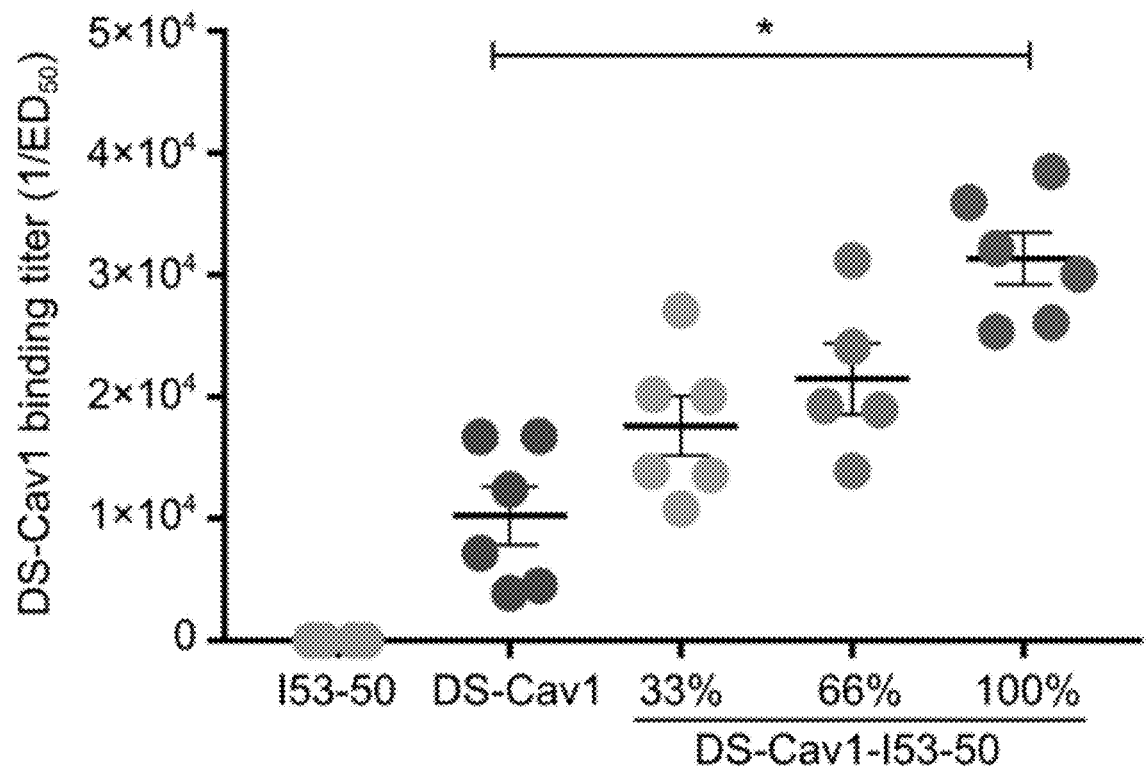
FIG. 7 is a graph depicting DS-Cav1-specific serum antibody titers from mice immunized with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. DS-Cav1-specific serum antibody titers were measured by ELISA on plates coated with DS-Cav1. Serum antibody titers for each mouse are plotted as circles, with the geometric mean within each group plotted as a horizontal line.

The DS-Cav1-foldon-I53-50 nanostructures displaying DS-Cav1 at 33%, 66%, and 100% valency were injected into mice using a prime-boost strategy as described above. Additional groups of mice were injected with trimeric DS-Cav1-foldon as a benchmark for the humoral immune response induced against DS-Cav1 by the nanostructures or I53-50 nanostructures lacking displayed DS-Cav1 as negative controls for a DS-Cav1 specific response. ELISA assays of serum extracted from the mice at defined time points after the injections were used to measure DS-Cav1 specific antibody titers present in the sera of the injected animals (FIG. 7). As expected, sera from animals injected with the I53-50 nanostructures lacking displayed DS-Cav1 did not contain antibodies specific to DS-Cav1. Trimeric DS-Cav1-foldon induced DS-Cav1-specific antibodies, in accordance with previous results (McClellan et al.). The 33%, 66%, and 100% valency DS-Cav1 nanostructures all induced higher DS-Cav1-specific antibody titers than trimeric DS-Cav1-foldon, with the antibody titers increasing with increasing DS-Cav1 valency. DS-Cav1-specific titers were roughly 2.5-fold higher on average in mice injected with 100% valency DS-Cav1-foldon-I53-50 nanostructures compared to DS-Cav1. These results demonstrate that immunogens in which paramyxovirus F proteins are multivalently displayed on self-assembling protein nanostructures can induce higher humoral immune responses when injected into animals.

Figure 8:
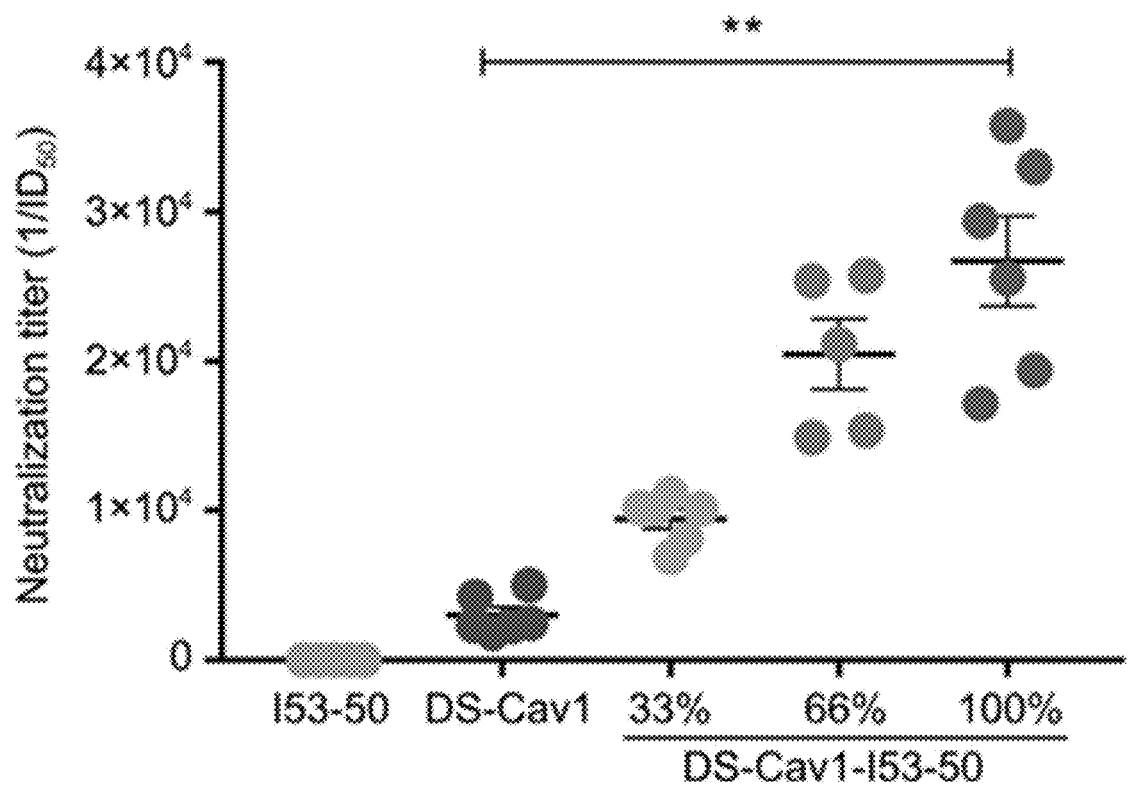
FIG. 8 is a graph depicting serum neutralization activity elicited by immunization with DS-Cav1-I53-50 nanostructures. Groups of mice were immunized with I53-50 nanostructures lacking additional antigen, trimeric DS-Cav1, or I53-50 nanostructures bearing DS-Cav1 antigen at 33%, 66%, or 100% valency. Neutralization titers for each mouse are plotted as circles, with the geometric mean within each group plotted as a horizontal line.

The sera from the mice injected with the series of immunogens described above was also evaluated for the presence of neutralizing antibody titers using the standard neutralization assay in HEp-2 cells (FIG. 8). The trend in serum neutralizing antibody titers correlated highly with the trend observed in DS-Cav1-specific binding antibody titers. Sera from animals injected with the I53-50 nanostructures lacking displayed DS-Cav1 did not neutralize virus, consistent with the lack of DS-Cav1-specific antibodies in these sera. The sera from animals injected with trimeric DS-Cav-1-foldon neutralized virus with an average titer ($1/ID_{50}$) of 3,030. The 33%, 66%, and 100% valency DS-Cav1-I53-50 nanostructures induced higher neutralizing antibody titers than trimeric DS-Cav1-foldon, with average titers of 9,400, 20,000, and 30,500, respectively. These results demonstrate that the higher humoral response induced by immunogens in which paramyxovirus F proteins are multivalently displayed on self-assembling protein nanostructures result in more effective virus neutralization.

Figure 9A:
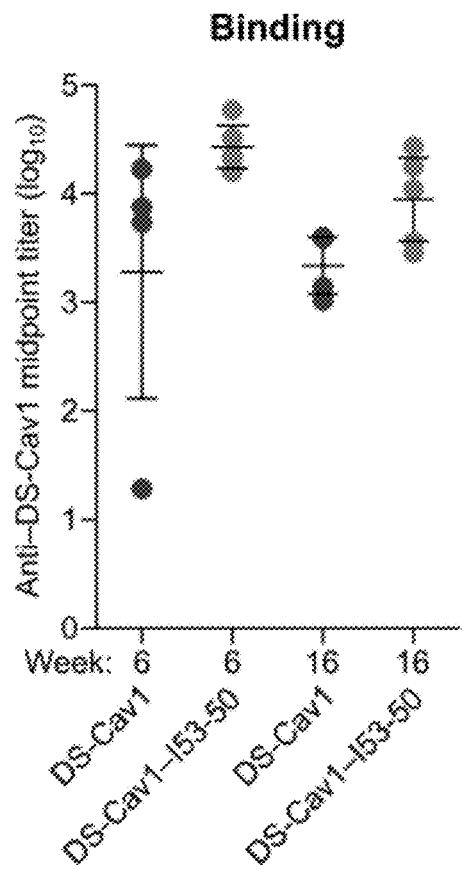
FIG. 9A-9B are graphs depicting immunogenicity in a primate immune system elicited by immunization with DS-Cav1-foldon I53-50 nanostructures. Rhesus macaques were injected at weeks 0 and 4 with either free DS-Cav1 trimer or DS-Cav1-foldon-I53-50 nanostructures displaying DS-Cav1 at 100% valency. In both cases, the dose of DS-Cav1 antigen was 50 μg, and the immunogens were formulated with the MF59-like, squalene-based oil-in-water emulsion adjuvant SWE. Sera obtained from the animals at weeks 6 and 16 were evaluated for anti-DS-Cav1 antibody titers (FIG. 9A) and RSV-neutralizing antibody titers (FIG. 9B).
Figure 9B:
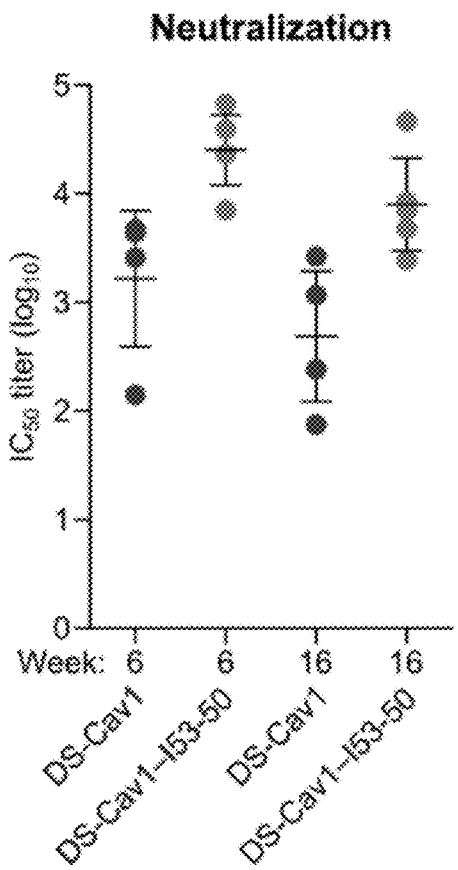

The DS-Cav1-foldon-I53-50 nanostructures were also injected into Rhesus macaques to evaluate their immunogenicity in a primate immune system. The animals were injected intramuscularly at weeks 0 and 4 with either free DS-Cav1 trimer or DS-Cav1-foldon-I53-50 nanostructures displaying DS-Cav1 at 100% valency. In both cases, the dose of DS-Cav1 antigen was 50 μg, and the immunogens were formulated with the MF59-like, squalene-based oil-in-water emulsion adjuvant SWE. Sera obtained from the animals at weeks 6 and 16 were evaluated for anti-DS-Cav1 antibody titers and RSV-neutralizing antibody titers (FIG. 9). The results mirrored those obtained in mice. At week 16, the mean anti-DS-Cav1 antibody titer was 4-fold higher in animals injected with the DS-Cav1-foldon-I53-50 nanostructure compared to animals injected with trimeric DS-Cav1. The mean RSV-neutralizing antibody titer at week 16 was 16-fold higher in animals injected with the DS-Cav1-foldon-I53-50 nanostructure compared to animals injected with trimeric DS-Cav1. These results demonstrate, in a primate immune system, that immunogens in which paramyxovirus F proteins are multivalently displayed on self-assembling protein nanostructures induce more robust humoral immune responses, including high levels of virus-neutralizing antibodies, than the trimeric paramyxovirus F proteins alone.

Physical Stabilization of DS-Cav1 by Fusion to I53-50A

Figure 10:
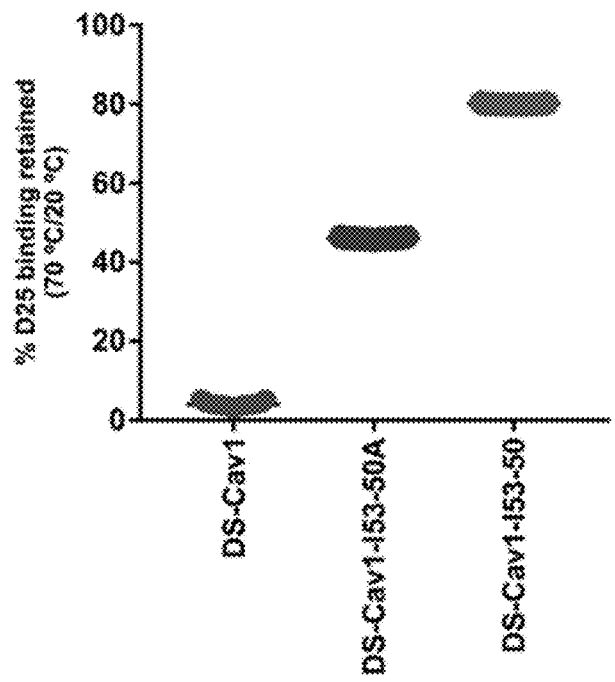
FIG. 10 is a graph depicting the physical stability of DS-Cav1 when fused to I53-50A and/or when further assembled into the icosahedral nanostructure. Samples of trimeric DS-Cav1, trimeric DS-Cav1-foldon-I53-50A, and DS-Cav1-foldon-I53-50 nanostructures containing equivalent concentrations of DS-Cav1 were split into four aliquots and incubated at 20, 50, 70 or 80° C. for 1 hour. After cooling to room temperature, D25 binding was assayed by surface plasmon resonance (SPR).
Figure 11A:
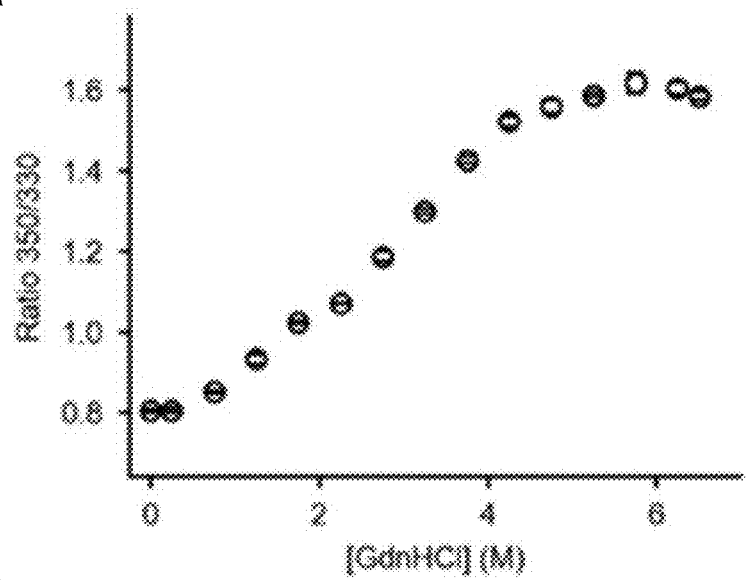
FIG. 11A-11J are graphs depicting physical stability of the nanostructures. Chemical denaturation in guanidine hydrochloride (GdnHCl), monitored by intrinsic tryptophan fluorescence, was used as a second, antibody-independent technique to evaluate physical stability of trimeric DS-Cav1 (FIG. 11A-11B), DS-Cav1-foldon-I53-50A (FIG. 11C-11D), DS-Cav1-foldon-I53-50 (FIG. 11E-11F), I53-50 (FIG. 11G-11H), and I53-50A (FIG. 11I-11J). The data indicate superior physical stability of the DS-Cav1 antigen when genetically fused to the I53-50A nanostructure component.
Figure 11B:
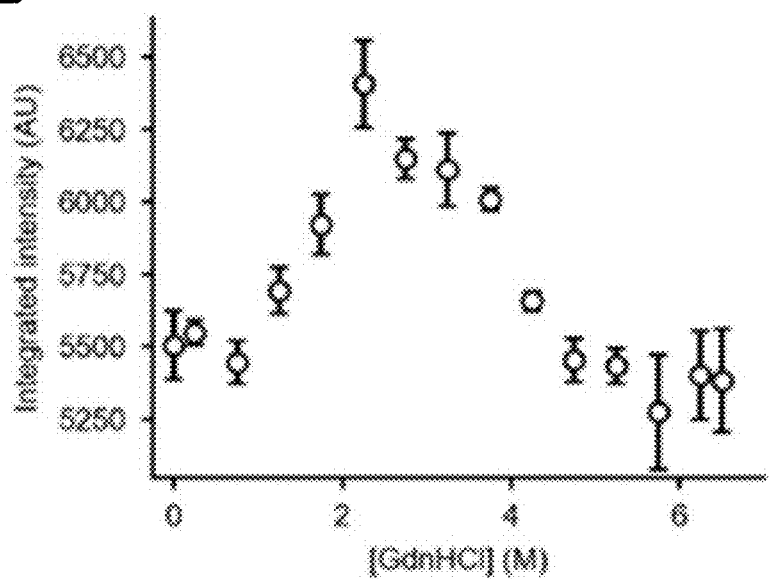
Figure 11C:
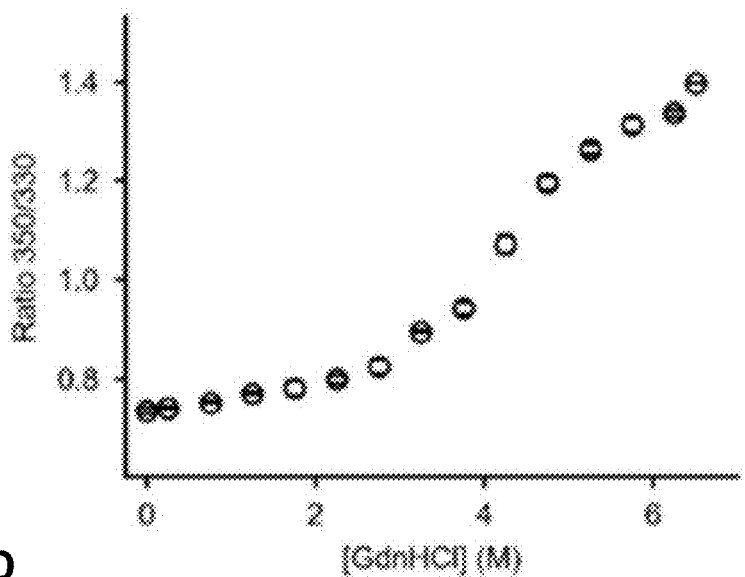
Figure 11D:
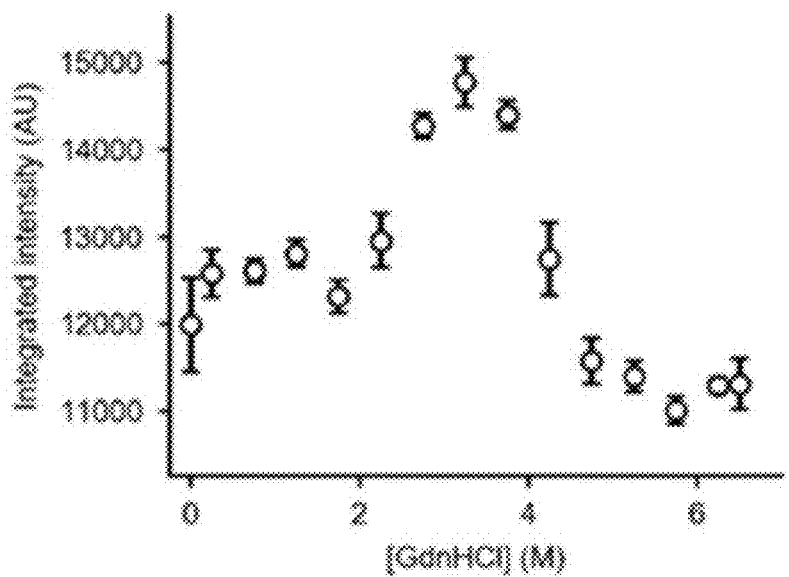
Figure 11E:
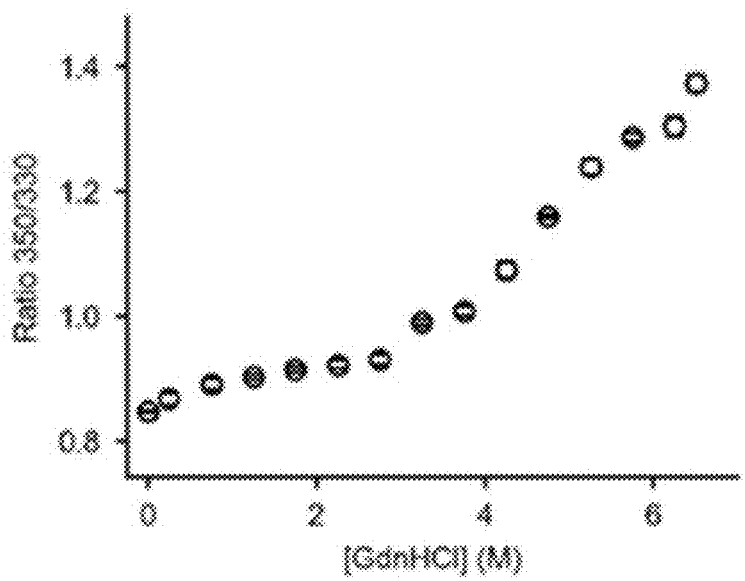
Figure 11F:
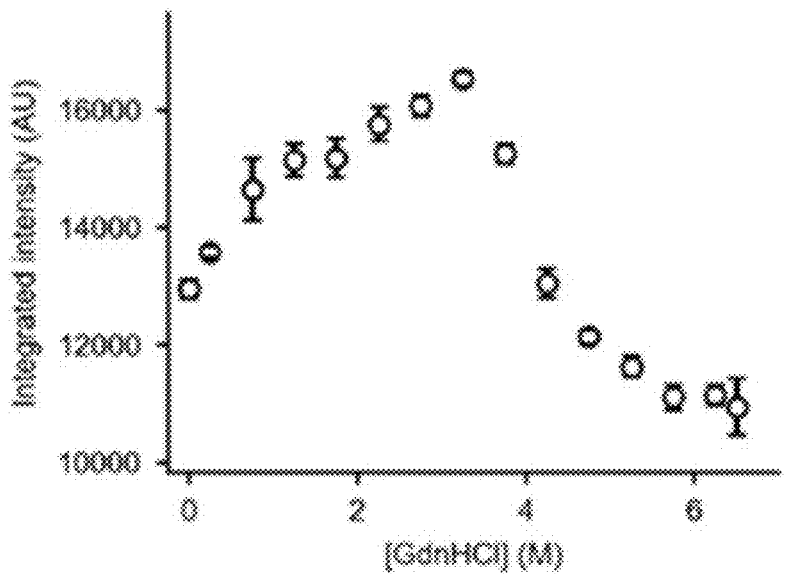
Figure 11G:
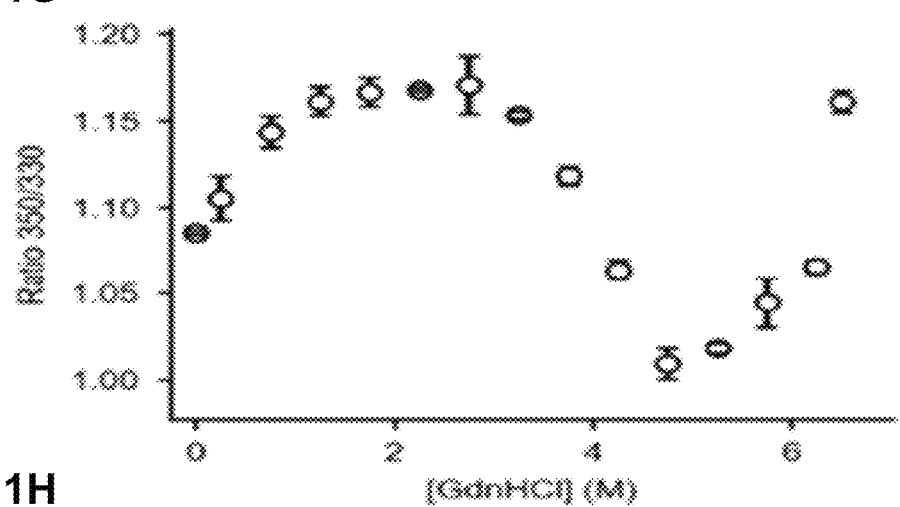
Figure 11H:
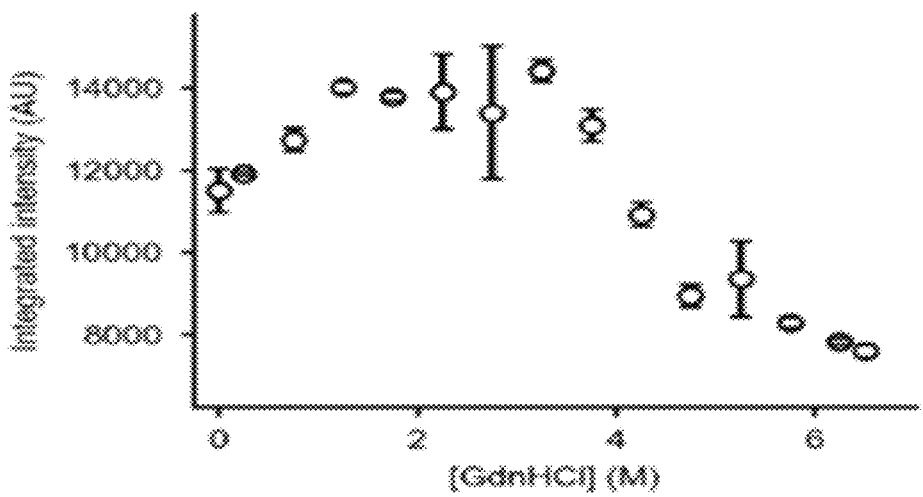
Figure 11I:
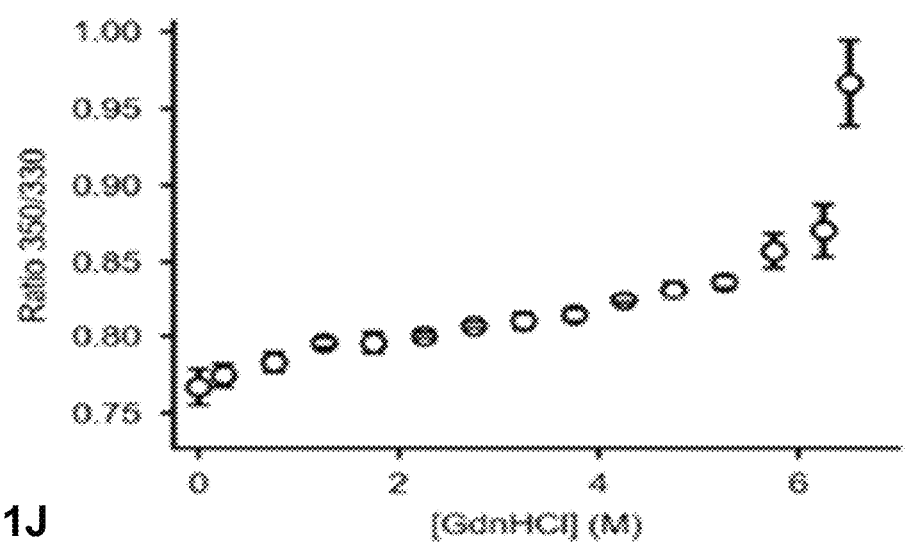
Figure 11J:
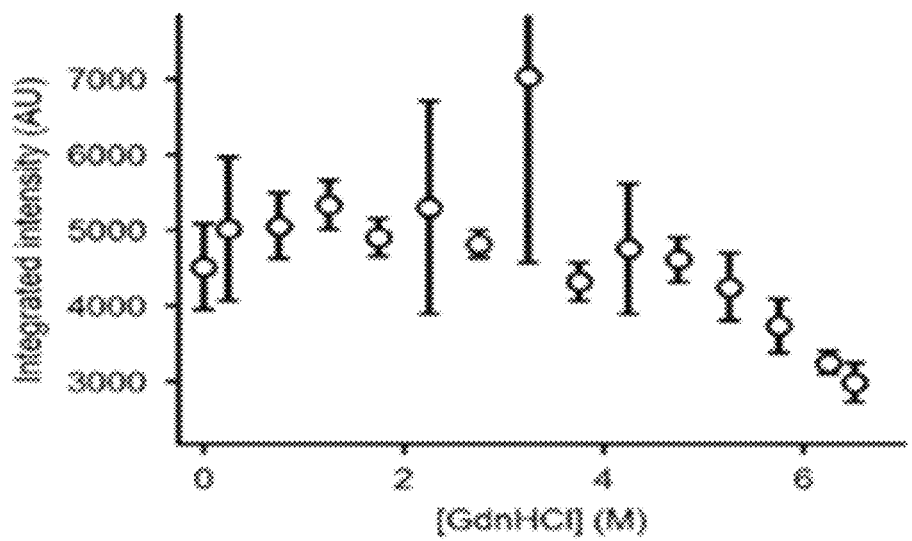

Given the key antigenic properties of prefusion F, we used two orthogonal approaches to measure the physical stability of DS-Cav1 when fused to I53-50A and/or when further assembled into the icosahedral nanostructure. The first assay measured the retention of binding by a prefusion-specific mAb (D25) after thermal stress, an approach that has been used previously to characterize prefusion F stability (McLellan et al. 2013; Joyce et al. 2016; Krarup et al. 2015). Samples of trimeric DS-Cav1, trimeric DS-Cav1-I53-50A, and DS-Cav1-I53-50 nanostructures containing equivalent concentrations (50 nM) of DS-Cav1 were split into four aliquots and incubated at 20, 50, 70 or 80° C. for 1 hour. After cooling to room temperature, D25 binding was assayed by surface plasmon resonance (SPR). We found that all samples bound D25 equivalently at 20 and 50° C., but lost most of their reactivity to D25 after 1 hour at 80° C. as previously reported for DS-Cav1 (McLellan et al. 2013; Joyce et al. 2016) (FIG. 10). Interestingly, while D25 was also unable to bind trimeric DS-Cav1 incubated at 70° C. for 1 hour, trimeric DS-Cav1-I53-50A and the DS-Cav1-I53-50 nanostructures retained 50 and 80% of their respective binding signals (FIG. 10). While the multivalent nature of the DS-Cav1-I53-50 nanostructures complicates direct quantitative comparisons to trimeric DS-Cav1, these results indicate that genetic fusion to the I53-50A trimer further stabilizes the prefusion conformation of DS-Cav1, and suggest that this increased stability is maintained in the context of the assembled nanostructure immunogen.

We used chemical denaturation in guanidine hydrochloride (GdnHCl), monitored by intrinsic tryptophan fluorescence, as a second, antibody-independent technique to evaluate physical stability. Analyzing fluorescence emission from DS-Cav1 incubated in 0-6.5 M GdnHCl revealed that the protein undergoes two subtly distinct transitions, one between 0.25 and 2.25 M GdnHCl and another between 2.25 and 5.75 M (FIG. 11). In contrast, only a single transition is apparent for trimeric DS-Cav1-I53-50A, occurring between 2.25 and 6.25 M GdnHCl (FIG. 11). It is unclear at present whether the transition at lower [GdnHCl] observed for DS-Cav1 is absent from trimeric DS-Cav1-I53-50A or simply shifted to higher [GdnHCl]. However, it is clear that the native conformation of DS-Cav1 is stabilized by genetic fusion to trimeric I53-50A, mirroring the results obtained by measuring D25 binding after thermal stress. Comparing the data for the DS-Cav1-I53-50 nanostructure and the I53-50 nanostructure alone (lacking fused DS-Cav1) indicated that the stabilization is maintained upon assembly to the icosahedral nanostructure (FIG. 11). The source of this effect is likely the extreme stability of the I53-50A trimer. I53-50A is derived from the KDPG aldolase of the hyperthermophilic bacterium *T. maritima* and only began to exhibit changes in fluorescence at very high 5.75 M) GdnHCl concentrations (FIG. 11).

We made addition constructs to assess the number of GS repeats and the need for a stabilization domain such as the Foldon moiety.

| IPD Name | MS (Da) | Construct Information |
|---|---|---|
| RSV_F-10 | 74005.38 | DS-Cav1-8GS-HelExt-50A |
| RSV_F-11 | 74293.64 | DS-Cav1-12GS-HelExt-50A |
| RSV_F-12 | 74551.87 | DS-Cav1-16GS-HelExt-50A |
| RSV_F-13 | 77212.97 | DS-Cav1-foldon-10GS-HelExt-50A |
| RSV_F-14 | 77558.28 | DS-Cav1-foldon-15GS-HelExt-50A |
| RSV_F-15 | 77933.62 | DS-Cav1-foldon-20GS-HelExt-50A |

Studies were based on expression yield in a small-scale transient transfection. Plasmids capable of expressing the relevant constructs were transformed into NEB 5α E. coli cells and selected on LB+carbenicillin agar plates. 1 mL cultures were prepared by inoculating TB media with a bacterial colony and again selecting with 50 ug/mL carbenicillin. A Qiagen Mini Prep kit was used to purify plasmid from the E. coli cultures in accordance with their protocol. Expi293F™ Cells (ThermoFisher) were cultured in Expi293™ Expression Medium (ThermoFisher) supplemented with penicillin (100 u/mL) and streptomycin (100 µg/mL) at 8% $CO_2$, 37° C., and 125 rpm shaking.

On the day prior to transfection, cells were seeded at a concentration of 2E6 cells/mL. On the day of transfection, cells were counted by a Countess II (ThermoFisher) with trypan blue to determine cell viability. Cell concentration was adjusted to 2.5E6 cells/mL, and cells where plated into untreated 12-well plates (Corning) in 1 mL volumes. 1 µg of DNA plasmid were transfected per each well using Expifectamine™ (ThermoFisher), following the manufacturer's directions. Enhancers, components of ThermoFisher's Expifectamine™ Transfection Kit, were added 18 hours after transfection. The 1 mL cultures were harvested 5 days post-transfection, and the cells were pelleted from the supernatant by centrifugation at 1,500×g for 5 minutes at 4° C. Supernatants were filtered through a 0.45 µM filter with a PVDF membrane.

Filtered supernatants containing DS-Cav1-I53-50A constructs were denatured and boiled for 10 minutes at 95° C. for 10 minutes in 2× Laemmli buffer with 2-mercaptoethanol. SDS-PAGE separated the sample fractions, which were then transferred to a nitrocellulose membrane and probed with palivizumab, followed with a secondary antibody, anti-human conjugated to HRP. Blot was imaged using Clarity Western ECL Blotting Substrate (Bio-Rad).

Filtered supernatants containing DS-Cav1-I53-50A constructs were bound to Nunc MaxiSorp™ 96-well plates in a two-fold dilution series. The pre-fusion conformation-specific antibody D25 was used to detect DS-Cav1-I53-50A, followed by a secondary anti-human antibody conjugated to HRP. Protein yield was determined colorimetrically via the substrate TMB and absorbances were collected at 450 nm.

The expression yields and binding of the prefusion-specific mAb D25 (data not shown) indicate that all constructs express well and are in the prefusion conformation. Those of skill in the art would have expected that a heterologous trimerization domain (such as the foldon) would be required for proper expression and folding of prefusion F constructs. Our results indicate that the I53-50A nanostructure component can support the expression and proper folding of DS-Cav1 without the use of a trimerization domain like the foldon. Binding of D25 to these constructs suggests that they are antigenically intact and would be expected to induce potent immune responses, including neutralizing antibodies, similarly to nanostructures comprising the DS-Cav1-foldon-I53-50 fusion polypeptide.

We claim:

1. A nanostructure, comprising:

(a) a plurality of first assemblies, each first assembly comprising a plurality of identical first polypeptides;

(b) a plurality of second assemblies, each second assembly comprising a plurality of identical second polypeptides, wherein the second polypeptide differs from the first polypeptide;

wherein the plurality of first assemblies non-covalently interact with the plurality of second assemblies to form a nanostructure; and wherein the nanostructure displays multiple copies of one or more paramyxovirus and/or pneumovirus F proteins, or antigenic fragments thereof, on an exterior of the nanostructure.

2. The nanostructure of claim 1, wherein:

(a) the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of SEQ ID NOS: 1-51; and (b) the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of a polypeptide selected from the group consisting of SEQ ID NOS: 1-51.

3. The nanostructure of claim 1, wherein the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to a polypeptide selected from the group consisting of SEQ ID NOS: 53, 61-68, and 101.

4. The nanostructure of claim 1, wherein the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to an RSV F protein or mutant thereof selected from the group consisting of SEQ ID NO:53 and 61-64, wherein the polypeptide includes one or more of the following residues: 67I, 149C, 458C, 46G, 465Q, 215P, 92D, and 487Q.

5. The nanostructure of claim 1, wherein the one or more paramyxovirus and/or pneumovirus F proteins, or antigenic fragments thereof, comprise a polypeptide having at least 75%, 80%, 85%, 90%, 91%, 92%, 93%, 94%, 95%, 96%, 97%, 98%, 99%, or 100% identity along its full length to an MPV F protein or mutant thereof selected from the group consisting of SEQ ID NO:65-68 and 101, wherein the polypeptide includes one or more of the following residues: 113C, 120C, 339C, 160F, 177L, 185P, and 426C.

6. The nanostructure of claim 1, wherein the first polypeptides and the second polypeptides comprise polypeptides having at least 75%, 80%, 85%, 90%, 91%, 92%, 93%, 94%, 95%, 96%, 97%, 98%, 99%, or 100% identity along their full length to the amino acid sequences selected from the following pairs:

SEQ ID NO:1 and SEQ ID NO:2 (153-34A and I53-34B);
SEQ ID NO:3 and SEQ ID NO:4 (153-40A and I53-40B);
SEQ ID NO:3 and SEQ ID NO:24 (153-40A and I53-40B.1);
SEQ ID NO:23 and SEQ ID NO:4 (153-40A.1 and 153-40B);
SEQ ID NO:35 and SEQ ID NO:36 (153-40A genus and I53-40B genus);
SEQ ID NO:5 and SEQ ID NO:6 (153-47A and I53-47B);
SEQ ID NO:5 and SEQ ID NO:27 (153-47A and I53-47B.1);
SEQ ID NO:5 and SEQ ID NO:28 (153-47A and I53-47B.1NegT2);
SEQ ID NO:25 and SEQ ID NO:6 (153-47A.1 and 153-47B);
SEQ ID NO:25 and SEQ ID NO:27 (153-47A.1 and 153-47B.1);
SEQ ID NO:25 and SEQ ID NO:28 (153-47A.1 and 153-47B.1NegT2);
SEQ ID NO:26 and SEQ ID NO:6 (153-47A.1NegT2 and 153-47B);
SEQ ID NO:26 and SEQ ID NO:27 (153-47A.1NegT2 and 153-47B.1);
SEQ ID NO:26 and SEQ ID NO:28 (153-47A.1NegT2 and I53-47B.1NegT2);
SEQ ID NO:37 and SEQ ID NO:38 (153-47A genus and 153-47B genus);
SEQ ID NO:7 and SEQ ID NO:8 (153-50A and I53-50B);
SEQ ID NO:7 and SEQ ID NO:32 (153-50A and I53-50B.1);
SEQ ID NO:7 and SEQ ID NO:33 (153-50A and I53-50B.1NegT2);
SEQ ID NO:7 and SEQ ID NO:34 (153-50A and 153-50B.4PosT1);
SEQ ID NO:29 and SEQ ID NO:8 (153-50A.1 and 153-50B);
SEQ ID NO:29 and SEQ ID NO:32 (153-50A.1 and 153-50B.1);
SEQ ID NO:29 and SEQ ID NO:33 (153-50A.1 and 153-50B.1NegT2);
SEQ ID NO:29 and SEQ ID NO:34 (153-50A.1 and 153-50B.4PosT1);
SEQ ID NO:30 and SEQ ID NO:8 (153-50A.1NegT2 and I53-50B);
SEQ ID NO:30 and SEQ ID NO:32 (153-50A.1NegT2 and I53-50B.1);
SEQ ID NO:30 and SEQ ID NO:33 (153-50A.1NegT2 and I53-50B.1NegT2);
SEQ ID NO:30 and SEQ ID NO:34 (153-50A.1NegT2 and I53-50B.4PosT1);
SEQ ID NO:31 and SEQ ID NO:8 (153-50A.1PosT1 and 153-50B);
SEQ ID NO:31 and SEQ ID NO:32 (153-50A.1PosT1 and 153-50B.1);
SEQ ID NO:31 and SEQ ID NO:33 (153-50A.1PosT1 and 153-50B.1NegT2);
SEQ ID NO:31 and SEQ ID NO:34 (153-50A.1PosT1 and 153-50B.4PosT1);
SEQ ID NO:39 and SEQ ID NO:40 (153-50A genus and I53-50B genus);
SEQ ID NO:9 and SEQ ID NO:10 (153-51A and 153-51B);
SEQ ID NO:11 and SEQ ID NO:12 (152-03A and I52-03B);
SEQ ID NO:13 and SEQ ID NO:14 (152-32A and I52-32B);
SEQ ID NO:15 and SEQ ID NO: 16 (152-33A and I52-33B);
SEQ ID NO:17 and SEQ ID NO:18 (132-06A and I32-06B);
SEQ ID NO:19 and SEQ ID NO:20 (132-19A and I32-19B);
SEQ ID NO:21 and SEQ ID NO:22 (132-28A and I32-28B);
SEQ ID NO:23 and SEQ ID NO:24 (153-40A.1 and 153-40B.1);
SEQ ID NO:41 and SEQ ID NO:42 (T32-28A and T32-28B);
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and
SEQ ID NO:51 and SEQ ID NO:44 (T33-31B and T33-09B (also referred to as T33-31B)).

7. The nanostructure of claim 1, wherein the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-31A (SEQ ID NO: 51) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-09B/T33-31B (SEQ ID NO:44).

8. The nanostructure of claim 1, wherein the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15B (SEQ ID NO: 46) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of T33-15A (SEQ ID NO:45).

9. The nanostructure of claim 1, wherein the first polypeptides comprise polypeptides having at least 75%, 80%, 85%, 90%, 91%, 92%, 93%, 94%, 95%, 96%, 97%, 98%, 99%, or 100% identity along their full length to the amino acid sequence selected from the group consisting of 153-50A (SEQ ID NO:7), 153-50A.1 (SEQ ID NO:29), 153-50A.1NegT2 (SEQ ID NO: 30), and I53-50A.1PosT1 (SEQ ID NO:31), and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence selected from the group consisting of 153-50B (SEQ ID NO:8), 153-50B.1 (SEQ ID NO:32), 153-50B.1NegT2 (SEQ ID NO: 33), and I53-50B.4PosT1 (SEQ ID NO:34).

10. The nanostructure of claim 1, wherein the first polypeptides comprise polypeptides having at least 75%, 80%, 85%, 90%, 91%, 92%, 93%, 94%, 95%, 96%, 97%, 98%, 99%, or 100% identity along their full length to the amino acid sequence of 132-28A (SEQ ID NO: 21) and the second polypeptides comprise polypeptides having at least 75%, 80%, 85%, 90%, 91%, 92%, 93%, 94%, 95%, 96%, 97%, 98%, 99%, or 100% identity along their full length to the amino acid sequence of 132-28B (SEQ ID NO:22).

11. The nanostructure of claim 1, wherein the one or more paramyxovirus and/or pneumovirus F proteins, or antigenic fragments thereof, are expressed as a fusion protein with the first polypeptides.

12. The nanostructure of claim 11, wherein the plurality of first assemblies each comprise identical fusion proteins.

13. The nanostructure of claim 11, wherein the plurality of first assemblies in total comprise two or more paramyxovirus and/or pneumovirus F proteins, or antigenic fragments thereof.

14. The nanostructure of claim 11, wherein only a subset of the first polypeptides comprises a fusion protein with an F protein or antigenic fragment thereof.

15. The nanostructure of claim 1, wherein each first assembly comprises a homotrimer of the first polypeptide.

16. The nanostructure of claim 1, wherein the one or more paramyxovirus and/or pneumovirus F proteins, or antigenic fragments thereof comprises polypeptides having at least 75%, 80%, 85%, 90%, 91%, 92%, 93%, 94%, 95%, 96%, 97%, 98%, 99%, or 100% identity along their full length to the amino acid sequence the amino acid sequence of DS-Cav1 (SEQ ID NO: 53).

17. The nanostructure of claim 11, wherein each fusion protein comprises an amino acid linker positioned between the first polypeptide and the one or more paramyxovirus and/or pneumovirus F proteins, or antigenic fragment thereof.

18. The nanostructure of claim 17, wherein the amino acid linker sequence comprises one or more trimerization domain.

19. The nanostructure of claim 17, wherein the amino acid linker sequence comprises the amino acid sequence GYIPEAPRDGQAYVRKDGEWVLLSTFL (SEQ ID NO: 54).

20. The nanostructure of claim 17, wherein the amino acid linker sequence comprises a Gly-Ser linker.

21. The nanostructure of claim 11, wherein the fusion protein comprises polypeptides having at least 75%, 80%, 85%, 90%, 91%, 92%, 93%, 94%, 95%, 96%, 97%, 98%, 99%, or 100% identity along their full length to the amino acid sequence selected from the group consisting of SEQ ID NOS: 69-100.

22. The nanostructure of claim 21, wherein:
(a) when each fusion protein is DS-Cav1-foldon-T33-31A (SEQ ID NO:69) or DS-Cav1-T33-31A (SEQ ID NO:70), each second polypeptide is T33-31B (SEQ ID NO:44);
(b) when each fusion protein is DS-Cav1-foldon-T33-15B (SEQ ID NO:71) or DS-Cav1-T33-15B (SEQ ID NO:72), each second polypeptide is T33-15A (SEQ ID NO:45);
(c) when each fusion protein is DS-Cav1-foldon-153-50A (SEQ ID NO:73) or DS-Cav1-153-50A (SEQ ID NO:74), each second polypeptide is 153-50B (SEQ ID NO:8), 153-50B.1 (SEQ ID NO: 32), 153-50B.1NegT2 (SEQ ID NO:33), or 153-50B.4PosT1 (SEQ ID NO:34); or
(d) when each fusion protein is DS-Cav1-132-28A (SEQ ID NO:75), each second polypeptide is I32-28B (SEQ ID NO:22).

23. The nanostructure of claim 16, wherein each first polypeptide comprises a fusion protein of DS-Cav1 (SEQ ID NO:53) linked to SEQ ID NO:7 (153-50A) via an amino acid linker.

24. The nanostructure of claim 23, wherein the amino acid linker comprises a Gly-Ser linker and/or a helical extension domain.

25. The nanostructure of claim 11, wherein each fusion protein comprises the amino acid sequence selected from the group consisting of SEQ ID NOS: 69-77 and 81-90.

26. The nanostructure of claim 23, wherein each fusion protein comprises the amino acid sequence of SEQ ID NO:76 (F10).

27. The nanostructure of claim 23, wherein each second polypeptide comprises the amino acid sequence selected from the group consisting of 153-50B (SEQ ID NO:8), 153-50B.1 (SEQ ID NO:32), 153-50B.1NegT2 (SEQ ID NO:33), or 153-50B.4PosT1 (SEQ ID NO: 34).

28. The nanostructure of claim 23, wherein each second polypeptide comprises the amino acid sequence of 153-50B.4PosT1 (SEQ ID NO:34).

29. The nanostructure of claim 1, wherein the nanostructure:
(a) binds prefusion F-specific antibodies including but not limited to monoclonal antibody D25;
(b) forms a symmetrical structure, including but not limited to an icosahedral structure;
(c) is stable at 50° C.; and/or
(d) is stable in 2.25M guanidine hydrochloride.

30. A recombinant nucleic acid encoding the first polypeptide fusion protein as recited in claim 11.

31. A recombinant expression vector comprising the recombinant nucleic acid of claim 30 operatively linked to a promoter.

32. A recombinant host cell, comprising the recombinant expression vector of claim 31.

33. A recombinant host cell, comprising one or more recombinant expression vectors capable of expressing the first polypeptides and the second polypeptides of claim 1.

34. An immunogenic composition comprising the nanostructure of claim 1, and a pharmaceutically acceptable carrier.

35. The immunogenic composition of claim 34, further comprising an adjuvant.

36. A method for generating an immune response to paramyxovirus and/or pneumovirus F protein in a subject, comprising administering to the subject in need thereof an effective amount of the nanostructure of claim 1 to generate the immune response.

37. A method for treating or limiting a paramyxovirus and/or pneumovirus infection in a subject, comprising administering to the subject in need thereof an effective amount of the nanostructure of claim 1, thereby treating or preventing paramyxovirus and/or pneumovirus infection in the subject.

38. The method of claim 36, wherein the administering results in production of paramyxovirus and/or pneumovirus neutralizing antibodies in the subject.

39. The method of claim 38, wherein the neutralizing antibodies are present in sera of the subject at a titer ($1/ID_{50}$) of at least 9,400.

40. A process for assembling the nanostructures of claim 1 in vitro, comprising mixing two or more nanostructure components in aqueous conditions to drive spontaneous assembly of the desired nanostructure.

41. The process of claim 40, wherein the mixing comprises mixing first assemblies comprising first polypeptides each comprising an F protein or antigenic fragment thereof with second assemblies comprising second polypeptides in an approximately 1:1 molar first polypeptide: second polypeptide ratio under conditions and for a time suitable to permit interaction of the first assemblies and the second assemblies to form the nanostructure.

42. The process of claim 40, wherein the mixing comprises mixing first assemblies comprising first polypeptides, wherein fewer than all first polypeptides comprise an F protein with second assemblies comprising second polypeptides in an approximately 1:1 first polypeptide: second polypeptide molar ratio under conditions and for a time suitable to permit interaction of the first assemblies and the second assemblies to form the nanostructure.

43. The process of claim 40, wherein the mixing comprises mixing first assemblies comprising first polypeptides each comprising an F protein, wherein in total the first polypeptides comprise multiple different F proteins with second assemblies comprising second polypeptides in an approximately 1:1 molar first polypeptide: second polypeptide ratio under conditions and for a time suitable to permit interaction of the first assemblies and the second assemblies to form the nanostructure comprising multiple F proteins, or antigenic fragments thereof.

44. A method for generating an immune response to paramyxovirus and/or pneumovirus F protein in a subject, comprising administering to the subject in need thereof an effective amount of the immunogenic composition of claim 34 to generate the immune response.

45. A method for treating or limiting a paramyxovirus and/or pneumovirus infection in a subject, comprising administering to the subject in need thereof an effective amount of the immunogenic composition of claim 34, thereby treating or preventing paramyxovirus and/or pneumovirus infection in the subject.

46. The process of claim 41, wherein the first polypeptides are trimeric first polypeptides.

47. The process of claim 42, wherein the first polypeptides are trimeric first polypeptides.

48. The process of claim 42, wherein fewer than 75% of the first polypeptides comprise an F protein.

49. The process of claim 43, wherein the first polypeptides are trimeric first polypeptides.

50. The process of claim 43, wherein the multiple different F proteins comprises 3, 4, or more different F proteins.

* * * * *